US009561311B2

(12) United States Patent
Becker et al.

(10) Patent No.: US 9,561,311 B2
(45) Date of Patent: Feb. 7, 2017

(54) MEDICAL DEVICES

(71) Applicant: CoDa Therapeutics, Inc., San Diego, CA (US)

(72) Inventors: David Lawrence Becker, Hertfordshire (GB); Colin Richard Green, Epson (NZ); Bradford James Duft, Rancho Santa Fe, CA (US)

(73) Assignee: CoDA Therapeutics, Inc., San Diego, CA (US)

(*) Notice: Subject to any disclaimer, the term of this patent is extended or adjusted under 35 U.S.C. 154(b) by 0 days.

(21) Appl. No.: 14/715,282

(22) Filed: May 18, 2015

(65) Prior Publication Data

US 2015/0297804 A1    Oct. 22, 2015

Related U.S. Application Data

(62) Division of application No. 12/809,941, filed as application No. PCT/US2008/014023 on Dec. 22, 2008, now Pat. No. 9,035,037.

(60) Provisional application No. 61/008,738, filed on Dec. 21, 2007.

(51) Int. Cl.
| | |
|---|---|
| C07H 21/04 | (2006.01) |
| C07H 21/02 | (2006.01) |
| A61K 39/395 | (2006.01) |
| A61K 48/00 | (2006.01) |
| A61L 31/16 | (2006.01) |
| A61L 17/00 | (2006.01) |
| A61L 27/54 | (2006.01) |
| A61L 31/08 | (2006.01) |
| A61L 31/10 | (2006.01) |

(52) U.S. Cl.
CPC ............ *A61L 31/16* (2013.01); *A61L 17/005* (2013.01); *A61L 27/54* (2013.01); *A61L 31/08* (2013.01); *A61L 31/10* (2013.01); *A61L 2300/25* (2013.01); *A61L 2300/252* (2013.01); *A61L 2300/258* (2013.01); *A61L 2300/432* (2013.01); *A61L 2300/602* (2013.01); *A61L 2300/606* (2013.01); *A61L 2300/608* (2013.01)

(58) Field of Classification Search
CPC .... A61K 48/00; C12N 2310/11; C12N 15/113
See application file for complete search history.

(56) References Cited

U.S. PATENT DOCUMENTS

| | | | |
|---|---|---|---|
| 4,861,757 A | 8/1989 | Antoniades et al. |
| 4,916,193 A | 4/1990 | Tang et al. |
| 4,994,071 A | 2/1991 | MacGregor |
| 5,004,810 A | 4/1991 | Draper |
| 5,092,877 A | 3/1992 | Pinchuk |
| 5,163,952 A | 11/1992 | Froix |
| 5,166,195 A | 11/1992 | Ecker |
| 5,304,121 A | 4/1994 | Sahatjian |
| 5,464,650 A | 11/1995 | Berg et al. |
| 5,591,227 A | 1/1997 | Dinh et al. |
| 5,599,352 A | 2/1997 | Dinh et al. |
| 5,697,967 A | 12/1997 | Dinh et al. |
| 6,251,136 B1 | 6/2001 | Guruwaiya et al. |
| 6,319,907 B1 | 11/2001 | Ferguson |
| 6,331,298 B1 | 12/2001 | Ferguson et al. |
| 6,344,028 B1 | 2/2002 | Barry |
| 6,358,556 B1 | 3/2002 | Ding et al. |
| 6,387,364 B1 | 5/2002 | Ferguson |
| 6,455,569 B1 | 9/2002 | Ferguson |
| 6,566,339 B1 | 5/2003 | Ferguson et al. |
| 6,585,764 B2 | 7/2003 | Wright et al. |
| 6,696,433 B2 | 2/2004 | Ferguson et al. |
| 6,702,850 B1 | 3/2004 | Byun et al. |
| 6,855,505 B2 | 2/2005 | Ferguson et al. |
| 6,900,181 B2 | 5/2005 | Ferguson et al. |
| 6,903,078 B1 | 6/2005 | Williams |
| 7,052,684 B2 | 5/2006 | Ferguson |
| 7,098,190 B1 | 8/2006 | Becker et al. |
| 7,153,822 B2 | 12/2006 | Jensen et al. |
| 7,250,397 B2 | 7/2007 | Larsen et al. |

FOREIGN PATENT DOCUMENTS

| | | |
|---|---|---|
| AU | 2008335718 A1 | 6/2009 |
| EP | 1100529 B1 | 5/2001 |
| WO | WO-00/06190 A1 | 2/2000 |
| WO | WO-00/44409 A1 | 8/2000 |
| WO | WO-03-032964 A2 | 4/2003 |
| WO | WO-2005-053600 A2 | 6/2005 |
| WO | WO-2006-069181 A2 | 6/2006 |
| WO | WO-2006/134494 A2 | 12/2006 |
| WO | WO-2009/075882 A9 | 6/2009 |

OTHER PUBLICATIONS

Altschul et al., "Basic Local Alignment Search Tool," *J. Mol. Biol.*, 1990, 215:403-410.
Altschul, "A Protein Alignment Scoring System at All Evolutionary Distances," *J. Mol. Evol.*, 1993, 36:290-300.
Benesch et al., "Preparation and properties of hemoglobin modified with derivatives of pyridoxal," *Methods Enzymol.*, 1981, 76:147-159.
Berthoud et al., "Peptide inhibitors of intercellular communication," *Am. J. Physiol. Lung Cell Mol. Physiol.*, 2000, 279:L619-L622.
Boitano et al., "Connexin mimetic peptides reversibly inhibit $Ca^{2+}$ signaling through gap junctions in airway cells," *Am. J. Physiol. Lung Cell Mol. Physiol.*, 2000, 279:L623-L630.
Brandner et al., "Connexins 26, 30, and 43: Differences Among Spontaneous, Chronic, and Accelerated Human Wound Healing," *J. Invest. Dermatol.*, May 5, 2004, 122:1310-1320.
Carvalho et al., "Conduction Defects and Arrhythmias in Chagas' Disease: Possible Role of Gap Junctions and Humoral Mechanisms," *J. Cardiovasc. Electrophysiol.* 1994, 5:686-698.
Chou et al., "Quantitative Analysis of Dose-Effect Relationships: The Combined Effects of Multiple Drugs or Enzyme Inhibitors," *Ad. Enzyme Reg.*, 1984, 22:27-55.

(Continued)

*Primary Examiner* — Amy Bowman
(74) *Attorney, Agent, or Firm* — Duane Morris LLP

(57) ABSTRACT

Medical devices comprising an anti-connexin agent suitable for introduction into a subject.

30 Claims, No Drawings

(56) References Cited

OTHER PUBLICATIONS

Clowes et al., "Kinetics of Cellular Proliferation after Arterial Injury," *Lab. Invest.*, 1983, 49(3):327-333.
Dahl et al., "Attempts to Define Functional Domains of Gap Junction Proteins with Synthetic Peptides," *Biophys. J.*, Nov. 1994, 67:1816-1822.
Darrow et al., "Expression of Multiple Connexins in Cultured Neonatal Rat Ventricular Myocytes," *Circ. Res.*, 1995, 76:381-387.
De Vriese et al., "Effects of connexin-mimetic peptides on nitric oxide synthase- and cyclooxygenase-independent renal vasodilation," *Kidney Int.*, 2002, 61:177-185.
Devereux et al., "A comprehensive set of sequence analysis programs for the VAX," *Nucleic Acids Research*, 1984, 12(1):387-395.
Evans et al., "Connexin mimetic peptides: specific inhibitors of gap-junctional intercellular communication," *Biochem. Soc. Trans.*, 2001, 29(4):606-612.
Furchgott et al., "The obligatory role of endothelial cells in the relaxation of arterial smooth muscle by acetylcholine," *Nature*, Nov. 27, 1980, 288:373-376.
Giepmans et al., "Interaction of c-Src with Gap Junction Protein Connexin-43," *J. Biol. Chem.*, Mar. 16, 2001, 276(11):8544-8549.
Goodenough et al., "Topological Distribution of Two Connexin32 Antigenic Sites in Intact and Split Rodent Hepatocyte Gap Junctions," *J. Cell Biol.*, Nov. 1988, 107:1817-1824.
Harlow et al., *Antibodies: A Laboratory Manual*, 1988, Cold Spring Harbor Publications, New York.
Henikoff et al., "Amino acid substitution matrices from protein blocks," *Proc. Natl. Acad. Sci. USA*, Nov. 1992, 89:10915-10919.
Jyung et al., "Increased wound-breaking strength induced by insulin-like growth factor I in combination with insulin-like growth factor binding protein-1," *Surgery*, Feb. 1994, 115(2):233-239.
Karlin et al., "Applications and statistics for multiple high-scoring segments in molecular sequences," *Proc. Natl. Acad. Sci. USA*, Jun. 1993, 90:5873-5877.
Kubes et al., "Nitric Oxide: An endogenous modulator of leukocyte adhesion," *Proc. Natl. Acad. Sci. USA*, Jun. 1991, 88:4651-4655.
Lepistö et al., "Platelet-derived growth factor isoforms PDGF-AA, -AB and -BB exert specific effects on collagen gene expression and mitotic activity of cultured human wound fibroblasts," *Biochem. Biophys. Res. Comm.*, Apr. 17, 1995, 209(2):393-399.
Leybeart et al., "Connexin Channels, Connexin Mimetic Peptides and ATP Release," *Cell Commun. Adhes.*, 2003, 10:251-257.
Lin et al., "v-Src phosphorylation of connexin 43 on Tyr247 and Tyr265 disrupts gap junctional communication," *J. Cell Biol.*, Aug. 20, 2001, 154(4):815-827.
Marcus et al., "Thromboregulation: multicellular modulation of platelet reactivity in hemostasis and thrombosis," *FASEB. J.*, Apr. 1993, 7:516-522.
McNamara et al., "L-Arginine Inhibits Balloon Catheter-Induced Intimal Hyperplasia," *Biochem. Biophys. Res. Commun.*, May 28, 1993, 193(1):291-296.
Meyer et al., "Inhibition of Gap Junction and Adherens Junction Assembly by Connexin and A-CAM Antibodies," *J. Cell Biol.*, Oct. 1992, 119(1):179-189.
Neckers et al. "Nonantisense Effects of Antisense Oligonucleotides," Ch. 7 from *Applied Antisense Oligonucleotide Technology*, Stein et al., eds., 1998 (Wiley-Liss).
Penne et al., "Coronary Artery Stents," *JACC*, Sep. 1996, 28(3):782-794.
Qiu et al., "Targeting Connexin43 Expression Accelerates the Rate of Wound Repair," *Current Biology*, Sep. 30, 2003, 13:1697-1703.
Rees et al., "Role of endothelium-derived nitric oxide in the regulation of blood pressure," *Proc. Natl. Acad. Sci. USA*, May 1989, 86:3375-3378.
Scatchard, "The Attractions of Proteins for Small Molecules and Ions," *Ann. N.Y. Acad. Sci.*, May 31, 1949, 51(4):660-672.
Sotozono et al., "Keratinocyte Growth Factor Accelerates Corneal Epithelial Wound Healing in Vivo," *Invest. Opthal. Vis. Science*, Jul. 1995, 36(8):1524-1529.
Steele et al., "Balloon angioplasty: Natural history of the pathophysiological response to injury in a pig model," *Circ. Res.*, Jul. 1985, 57(1):105-112.
Stoeckel, "A survey of stent designs," *Min. Invas. Ther. & Allied Technol.* 2002, 11(4): 137- 147.
Uchida et al., "Angioscopic observation of the coronary luminal changes induced by percutaneous transluminal coronary angioplasty," *Am. Heart. J.*, Apr. 1989, 117(4):769-776.
Yang et al., "Synthesis and biological activities of potent peptidomimetics selective for somatostatin receptor subtype 2," *Proc. Natl. Acad. Sci. USA*, Sep. 1998, 95:10836-10841.
Examination Report dated Apr. 12, 2013 from corresponding Australian Patent Application No. 2008343843, 3 pages.
Notice of Reasons for Rejection dated Aug. 12, 2013 from corresponding Japanese Patent Application No. 2010-539515, 7 pages.
Office Action dated May 7, 2014 from corresponding European Patent Application No. 08,867, 503.8, 5 pages.
Final Office Action dated May 13, 2014 from corresponding Japanese Patent Application No. 2010-539515, 4 total pages.

MEDICAL DEVICES

This application is a divisional of U.S. patent application Ser. No. 12/809,941, which was filed on Feb. 14, 2011, which is a National Stage Application under 35 U.S.C. §371 of International Application No. PCT/US2008/014023, filed Dec. 22, 2008 which claims the benefit of priority to U.S. Provisional Application No. 61/008,738 filed on Dec. 21, 2007. The disclosures of each of which are incorporated herein by reference.

FIELD

The subject matter pertains to medical devices, including devices having a composition, surface, or feature that exposes and/or delivers one or more anti-connexin agents, with or without one or more other therapeutic agents and/or wound healing agents to tissue and/or fluid with which they come into contact on use or application.

BACKGROUND

The following description includes information that may be useful in understanding the present invention. It is not an admission that any of the information provided herein is prior art, or relevant, to the presently described or claimed invention, or that any publication or document that is specifically or implicitly identified is prior art or a reference that may be used in evaluating patentability. All documents and other information referred to in this patent are incorporated herein by reference in their entirety.

Over the past two decades, much research effort has been directed towards the development of medical devices and machines that are used in a wide variety of clinical settings to repair, maintain, or enhance vital physiological functions of a subject mammal. For example, devices such as catheters, prosthetic heart valves, pacemakers, pulse generators, cardiac defibrillators, arteriovenous shunts, and stents are used extensively in the treatment of cardiac and other diseases. Other examples of medical devices, including screws, anchors, plates, staples, tacks, joints and similar devices, for example, are used in orthopedic surgery. These implantable medical devices are made from a wide variety of materials, including, for example, metals, plastics, and various polymeric materials. Other orthopedic devices include implants, such as implants for hip, shoulder, elbow and knee replacements and surgeries, or craniomaxillofacial reconstruction, and implant coatings, as well devices used in arthroscopic and laproscopic procedures, including burrs, suture-passing instruments, arthroscopic shavers. Other examples of medical devices include ocular devices, such as implants, including intraocular lenses and glaucoma shunts. Still other devices include gastrointestinal implants. Other examples of medical devices include devices for endoscopy, hysteroscopy, cytoscopy, bronchoscopy, etc.

When medical devices, for example, implantable medical devices, are brought into contact with a subject, natural bodily processes can result in inflammation, swelling, hypercellularity or other aberrant cellular disposition, growth and/or proliferation, and/or tissue damage. For example, platelets may attach to the medical device which can result in further complications at the site of use or implantation such as, for example, thrombosis, leukocyte attachment, and/or neutrophil and/or macrophage migration that lead to inflammation and/or aberrant cellular growth. An example of such a process resulting from the contacting of a medical device with a subject is provided by the use of a catheter or stent, which can result in tissue damage and/or restenosis. Restenosis, the reclosure of a peripheral or coronary artery following trauma to that artery generally caused by efforts to open a stenosed or occluded portion of the artery, and resulting trauma may be caused by, for example, balloon dilation, ablation, atherectomy or laser treatment of the artery. For example, balloon arterial injury reportedly results in endothelial denudation and subsequent regrowth of dysfunctional endothelium that may contribute to the local smooth muscle cell proliferation and extracellular matrix production that result in reocclusion of the arterial lumen. Restenosis has been reported to occur in as many as 50% of patients undergoing such angioplasty procedures. Restenosis is believed to be a natural healing process in reaction to the injury of the arterior wall caused by such angioplasty procedures. The healing process begins with the thrombotic mechanism at the site of the injury. The final steps of the healing process can be intimal hyperplasia, the uncontrolled migration and proliferation of medial smooth muscle cells, combined with their extracellular matrix production, until the artery is again stenosed or occluded.

In humans and other mammals wound injury triggers an organized complex cascade of cellular and biochemical events that will in most cases result in a healed wound. An ideally healed wound is one that restores normal anatomical structure, function, and appearance at the cellular, tissue, organ, and organism levels. Wound healing, whether initiated by trauma, microbes or foreign materials, proceeds via a complex process encompassing a number of overlapping phases, including inflammation, epithelialization, angiogenesis and matrix deposition. Normally, these processes lead to a mature wound and a certain degree of scar formation. Although inflammation and repair mostly occur along a prescribed course, the sensitivity of the process is dependent on the balance of a variety of wound healing modulating factors, including for example, a network of regulatory cytokines and growth factors.

Despite advances in the understanding of the principles underlying the wound healing process, there remains a significant unmet need in suitable therapeutic options for wound care, including delayed or compromised wound healing of wounds such as chronic wounds, as well as swelling, inflammation, epithelialization rates and scarring associated with these and other wounds, including acute and subacute wounds.

Gap junctions are cell membrane structures that facilitate direct cell-cell communication. A gap junction channel is formed of two connexons (hemichannels), each composed of six connexin subunits. Each hexameric connexon docks with a connexon in the opposing membrane to form a single gap junction. Gap junction channels are reported to be found throughout the body. Tissue such as the corneal epithelium, for example, has six to eight cell layers, yet is reported to expresses different gap junction channels in different layers with connexin 43 in the basal layer and connexin 26 from the basal to middle wing cell layers. In general, connexins are a family of proteins, commonly named according to their molecular weight or classified on a phylogenetic basis into alpha, beta, and gamma subclasses. At least 20 human and 19 murine isoforms have been identified. Different tissues and cell types are reported to have characteristic patterns of connexin protein expression and tissues such as cornea have been shown to alter connexin protein expression pattern following injury or transplantation (Qui, C. et al., (2003) Current Biology, 13:1967-1703; Brander et al., (2004), J. Invest Dermatol. 122:1310-20).

It has been reported that abnormal connexin function may be linked to certain disease states (e.g. heart diseases) (A. C. de Carvalho, et al., *J Cardiovasc Electrophysiol* 1994, 5 686). In certain connexin proteins, alterations in the turnover and trafficking properties may be induced by the addition exogenous agents which may affect the level of gap junctional intercellular communication (Darrow, B. J., et al. (1995). *Circ Res* 76: 381; Lin R, et al. (2001) *J Cell Biol* 154(4):815). Antisense technology has been reported for the modulation of the expression for genes implicated in viral, fungal and metabolic diseases. See, e.g., U.S. Pat. No. 5,166,195, (oligonucleotide inhibitors of HIV), U.S. Pat. No. 5,004,810 (oligomers for hybridizing to herpes simplex virus Vmw65 mRNA and inhibiting replication). See also U.S. Pat. No. 7,098,190 to Becker et al. (formulations comprising antisense nucleotides to connexins). See also Becker and Green PCT/US06/04131 ("Anti-connexin compounds and uses thereof").

There is a need for medical devices that will aid in ameliorating tissue damage and/or enhancing tissue repair and/or limiting or inhibiting complications associated with using or implanting medical devices in a subject, such as for example, inflammation, restenosis and so on. It would be desirable to provide a medical device that aids in prevention, amelioration or treatment of damaged tissue and/or inflammation, and/or the enhancement of tissue repair, as well as swelling, hypercellularity or other aberrant cellular disposition, growth and/or proliferation, and/or tissue damage. Such devices, methods of manufacture, and uses thereof, are provided herein.

SUMMARY

The inventions described and claimed herein have many attributes and embodiments including, but not limited to, those set forth or described or referenced in this Summary. The inventions described and claimed herein are not limited to or by the features or embodiments identified in this Summary, which is included for purposes of illustration only and not restriction.

The present invention is in part directed to new medical devices which may be used, for example, in the treatment and prevention of various diseases, disorders and/or conditions, including diseases, disorders, and/or conditions relating to tissue damage and/or inflammation, whether or not in excess, in a mammal including, but not limited to, the kind referenced herein, and/or enhancing tissue repair processes and/or ameliorating tissue damage and/or inflammation.

In one aspect, the invention also relates to a medical device for use or implantation in a subject, wherein said medical device comprises one or more anti-connexin agents in combination with one or more therapeutic agents, one or more gap junction modulating agents, and/or one or more wound healing agents.

In another aspect, the invention relates a medical device for use or implantation in a subject, wherein said medical device comprises an anti-connexin agent. In one embodiment, the anti-connexin agent is an anti-connexin 43 agent.

In another aspect, the invention relates a medical device for use or implantation in a subject, wherein said medical device comprises one or more anti-connexin polynucleotides.

In another aspect, the invention relates a medical device for use or implantation in a subject, wherein said medical device comprises one or more anti-connexin polypeptides.

In another aspect, the invention relates a medical device for use or implantation in a subject, wherein said medical device comprises one or more gap junction modulating agents.

In another aspect, the invention relates a medical device for use or implantation in a subject, wherein said medical device comprises an anti-connexin polypeptide and an anti-connexin polynucleotide.

In another aspect, the invention relates a medical device for use or implantation in a subject, wherein said medical device comprises a first coating containing one or more anti-connexin polynucleotides and a second coating containing one or more anti-connexin polypeptides whereby upon implantation or application of said device in a subject the anti-connexin polypeptide and the anti-connexin polynucleotide are sequentially administered. Preferably the anti-connexin polypeptide is administered first. In one embodiment, the medical device contains a controlled release formulation whereby the anti-connexin polypeptide and the anti-connexin polynucleotide are sequentially released.

In another aspect, the invention relates a medical device for use or implantation in a subject, wherein said medical device comprises one or more anti-connexin polynucleotides, one or more anti-connexin polypeptides, one or more therapeutic agents, one or more gap junction modifying agents, and/or one or more agents useful for wound healing. In further embodiments, the medical device contains layers for administration, portions of the medical device coated with different substances released at different rates, a controlled release formulation or mechanics to facilitate administration of said combination in any order, or means for mechanical administration in any desired order.

In one aspect, the invention relates to an implantable medical device comprising an anti-connexin agent releasable upon insertion of the medical device to or within a subject.

In one aspect, a medical device for use or implantation in a mammal, comprising an anti-connexin 43 compound releasable upon insertion of the medical device to or within a subject, is provided. In one embodiment, the anti-connexin 43 compound decreases connexin 43 protein expression. In another embodiment, the anti-connexin 43 compound is an antisense oligonucleotide. In another embodiment, the anti-connexin 43 compound is a siRNA oligonucleotide. In another embodiment, the anti-connexin 43 compound is an RNAi oligonucleotide. In another embodiment, the anti-connexin 43 compound is a peptide compound, e.g., a peptide that blocks or inhibits hemichannel opening. In another embodiment, the anti-connexin 43 compound is a peptidomimetic, e.g., a peptidomimetic that blocks or inhibits hemichannel opening. In another embodiment, the anti-connexin 43 compound is an anti-connexin 43 antibody or antigen binding fragment thereof. In another embodiment, the anti-connexin 43 compound is a monoclonal antibody. In another embodiment, the anti-connexin 43 compound is an F(v), Fab, Fab' or F(ab')$_2$ anti-connexin 43 antibody fragment. In another embodiment, the anti-connexin 43 compound is a chimeric or humanized antibody. In a further embodiment, the antibody fragment is a chimeric or humanized antibody fragment. In another embodiment, the anti-connexin 43 compound binds to connexin 43 mRNA. In another embodiment, the anti-connexin 43 compound binds to a connexin 43 hemichannel. In another embodiment, the anti-connexin 43 compound binds to a hemichannel extracellular loop. In another embodiment, the anti-connexin 43 compound blocks or inhibits a connexin 43 hemichannel. In another one embodiment, the anti-connexin 43 compound blocks or inhibits connexin 43 hemichannel opening. In another embodiment, the anti-connexin 43 compound is in a polynucleotide having a sequence selected for SEQ.ID.NOS.1 or 2 or a pharmaceutically acceptable salt thereof. In another embodiment, the anti-connexin 43 compound is a peptide having a sequence selected from SEQ.ID.NOS. 15 to 38 or a pharmaceutically acceptable salt thereof. In another embodiment, the anti-connexin 43 compound is selected from the group consisting of an antisense oligonucleotides, siRNA, and RNAi. In another embodiment, the anti-connexin 43 compound is a peptide of SEQ.ID.NOS. 18 or 19. In another embodiment, the anti-connexin 43 compound is a peptide of SEQ.ID.NO.19. In another embodiment, the anti-connexin 43 compound is a polynucleotide having a sequence selected from the group consisting of: SEQ.ID.NOS. 1 to 12. In another embodiment, the surface of the medical device comprises an anti-connexin or anti-connexin 43 agent. In another embodiment, the anti-connexin or anti-connexin 43 agent is present at a weight percentage of about 0.0001% to about 30%.

In another embodiment, the surface of the medical device contacts a target tissue within the subject upon use. In another embodiment, the target tissue is heart tissue or vascular tissue, or other tissue exposed to a device during or after a surgical procedure. In another embodiment, the release rate of the anti-connexin agent is controlled. In another embodiment, the medical device provides for surface contact release of the anti-connexin agent. In another embodiment, the medical device provides for the sustained release of the anti-connexin agent. In another embodiment, the medical device provides for the slow release of the anti-connexin agent. In another embodiment, the device comprises a coating containing an anti-connexin agent. In a further embodiment, the coating comprises a polymer. In another embodiment, the coating comprises a plurality of layers of a polymer/anti-connexin agent mixture. In another embodiment, the medical device is for implantation in a human. In another embodiment, the medical device comprises a stent. In another embodiment, the stent is a drug-eluting stent. In another embodiment, the medical device comprises a balloon, a prosthetic heart valve, an annuloplasty ring, a pulse generator, a cardiac defibrillator, an arteriovenous shunt, an anastomosis device, a hemostatic barrier or a pacemaker. In another embodiment, the medical device comprises an orbital implant, a lens, a lens implant, a corneal implant, or a glaucoma shunt. In another embodiment, the medical device comprises an orthopedic plate, a bone pin, a bone substitute, an anchor, a joint, a screw, or a vertebral disk. In another embodiment, the medical device comprises a device for knee, elbow, shoulder, or hip replacement, in whole or in part. In another embodiment, the medical device comprises a gastrointestinal implant. In another embodiment, the medical device is an endoscopy device. In another embodiment, the medical device comprises a graft, a shunt, a vascular implant, a tissue scaffold, an intraluminal device or a vascular support. In other embodiments, the medical device is for implantation in a non-human animal or bird. In another embodiment, the medical device comprises at least one channel formed in an outer surface thereof, and wherein the anti-connexin agent is included on and/or within at least one channel. In another embodiment, at least a portion of the medical device is formed, in whole or in part, of a substance that includes the anti-connexin agent. In another embodiment, the device further comprises one or more therapeutic agents. In another embodiment, the medical device is for use in a human or non-human animal or bird.

In another aspect, a method of preventing and/or treating damage associated with the use or implantation of a medical device in a subject comprising introducing into the subject a medical device of which at least a portion comprises an anti-connexin agent, wherein the damage is prevented, ameliorated and/or delayed, is provided. In one embodiment, the subject is a mammal. In one embodiment, the mammal is a human. In one embodiment, the mammal is selected from the group consisting of domestic and pet animals, sports animals, farm animals, zoo animals, and birds. In one embodiment, the mammal is a horse, a dog, or a cat.

In yet another aspect, a method of preventing and/or treating damage associated with the use or implantation of a medical device in a subject comprising use or implantation of a medical device which comprises an anti-connexin agent that is releasable at its point of contact, wherein the damage is prevented, ameliorated and/or reduced, is provided.

DETAILED DESCRIPTION

Definitions

Before further describing the inventions in general and in terms of various nonlimiting specific embodiments, certain terms used in the context of the describing the invention are set forth. Unless indicated otherwise, the following terms have the following meanings when used herein and in the appended claims. Those terms that are not defined below or elsewhere in the specification shall have their art-recognized meaning.

As used herein, "subject" refers to any animal classified as a mammal, including humans, domestic and farm animals, and zoo, sports, or pet animals, such as dogs, horses, cats, sheep, pigs, cows, etc. The preferred subject is a human.

As used herein, "mammal" refers to any animal classified as a mammal, including humans, domestic and farm animals, and zoo, sports, or pet animals, such as dogs, horses, cats, sheep, pigs, cows, etc. The preferred mammal herein is a human, including adults, children, and the elderly.

As used herein, a "disorder" is any disorder, disease, or condition that would benefit from an agent that reduces damage associated with the use or implantation of a medical device. Disorders include, but are not limited to, damage to tissue (including, e.g., heart, liver, kidney, CNS (including brain), joint, gastrointestinal tissue) and vascular damage.

As used herein, "pharmaceutically acceptable salts" refers to salts prepared from pharmaceutically acceptable non-toxic bases or acids including inorganic or organic bases and inorganic or organic acids the like. When the anti-connexin agent compound is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like As used herein, "preventing" or "prevention" means preventing in whole or in part, ameliorating or controlling in whole or in part, or reducing, decreasing, lessening or retarding in whole or in part.

The term "therapeutically effective amount" or "effective amount" means the amount of the subject compound that will elicit a desired response, for example, a biological or medical result or response of a tissue, system, animal or human that is sought, for example, by a researcher, veterinarian, medical doctor, or other clinician. That result can be alleviation of the signs, symptoms, or causes of a disease or disorder or condition, or any other desired alteration of a biological system. In the present invention, the result will typically involve, for example, the prevention, decrease, or reversal of tissue injury or damage, including inflammation, in whole or in part, associated with the use or implantation (temporary or permanent) of a medical device. The result will also typically involve the prevention, decrease, or reversal of inflammation.

As used herein, the term "treatment" or "treating" refers to both therapeutic treatment and prophylactic or preventative measures. Prevention or prophylaxis may be in whole or in part.

The term "damage associated with the use or implantation of a medical device" refers to damage or injury to tissue resulting from the insertion, presence, manipulation or removal of a medical device. "Damage associated with the use or implantation of a medical device" may be evidenced by one or more conditions, including an inflammatory response, a proliferative response including neointimal proliferation, cellular proliferation, removal of endothelium and damage to smooth muscle cells, stenosis or restenosis following angioplasty or insertion and removal of a medical device, neointimal hyperplasia leading to stenosis or restenosis, platelet adhesion restenosis, and other inflammatory processes which are associated with implantation, use and removal of a medical device, including swelling.

The terms "peptidomimetic" and "mimetic" include naturally occurring and synthetic chemical compounds that may have substantially the same structural and functional characteristics of protein regions which they mimic. In the case of connexins, these may mimic, for example, the extracellular loops of opposing connexins involved in connexon-connexon docking and cell-cell channel formation, and/or the extracellular loops of hemichannel connexins.

As used herein, the term "peptide analogs" refer to the compounds with properties analogous to those of the template peptide and can be non-peptide drugs. "Peptidomimetics" (also known as peptide mimetics) which include peptide-based compounds, also include such non-peptide based compounds such as peptide analogs. Peptidomimetics that are structurally similar to therapeutically useful peptides can be used to produce an equivalent or enhanced therapeutic or prophylactic effect. Generally, peptidomimetics are structural or functional mimics (e.g. identical or similar) to a paradigm polypeptide (i.e., a polypeptide that has a biological or pharmacological function or activity), but can also have one or more peptide linkages optionally replaced by a linkage selected from the group consisting of, for example, —CH$_2$NH—, —CH$_2$S—, —CH$_2$—CH$_2$—, —CH=CH— (cis and trans), —COCH$_2$—, —CH(OH)CH$_2$—, and —CH$_2$SO—. The mimetic can be either entirely composed of natural amino acids, synthetic chemical compounds, non-natural analogues of amino acids, or, is a chimeric molecule of partly natural peptide amino acids and partly non-natural analogs of amino acids. The mimetic can also comprise any amount of natural amino acid conservative substitutions as long as such substitutions also do not substantially alter mimetic activity. In the case of connexins, these can mimic, for example, the extracellular loops of opposing connexins involved in connexon-connexon docking and cell-cell channel formation. For example, a mimetic composition can be useful as a gap junction modulating agent if it is capable of downregulating biological actions or activities of connexons, such as, for example, preventing the docking of connexons to form gap-junction-mediated cell-cell communications, or preventing the opening of connexons to expose the cell cytoplasm to the extracellular millieu. Peptidomimetics encompass those described herein, as well as those as may be known in the art, whether now known or later developed.

The term "composition" is intended to encompass a product comprising one or more ingredients.

In general, the terms "modulator" and "modulation" of gap junction activity, as used herein in its various forms, refers to inhibition in whole or in part of the action or activity of a gap junction or a hemichannel and may function as gap junction modulating agents.

In general, the term "protein" refers to any polymer of two or more individual amino acids (whether or not naturally occurring) linked via peptide bonds, as occur when the carboxyl carbon atom of the carboxylic acid group bonded to the alpha-carbon of one amino acid (or amino acid residue) becomes covalently bound to the amino nitrogen atom of the amino group bonded to the alpha-carbon of an adjacent amino acid. These peptide bond linkages, and the atoms comprising them (i.e., alpha-carbon atoms, carboxyl carbon atoms (and their substituent oxygen atoms), and amino nitrogen atoms (and their substituent hydrogen atoms)) form the "polypeptide backbone" of the protein. In addition, as used herein, the term "protein" is understood to include the terms "polypeptide" and "peptide" (which, at times, may be used interchangeably herein). Similarly, protein fragments, analogs, derivatives, and variants are may be referred to herein as "proteins," and shall be deemed to be a "protein" unless otherwise indicated. The term "fragment" of a protein refers to a polypeptide comprising fewer than all of the amino acid residues of the protein. A "domain" of a protein is also a fragment, and comprises the amino acid residues of the protein often required to confer activity or function.

As used herein, it is to be understood that reference to a particular connexin is a reference to all species variants thereof, even if their molecular weights are different. Thus, for example, a reference to "connexin 43" means not only human connexin 43 but to the analogous connexin in each other species, no matter whether they are also 43 Kd. Similarly, reference to a non-human "connexin 43" is a reference to the connexin 43 analog or variant in that species. Thus, for example, reference to "horse connexin 43" is a reference to the relevant analog or variant of human connexin 43 in horse even if it does not have a 43 Kd molecular weight.

Anti-Connexin Agents

Anti-connexin agents of the invention described herein are capable of modulating or affecting the transport of molecules into and out of cells (e.g., blocking or inhibiting or downregulating). Thus certain anti-connexin agents described herein modulate cellular communication (e.g., cell to cell). Certain anti-connexin agents modulate or effect transmission of molecules between the cell cytoplasm and the periplasmic or extracellular space. Such anti-connexin agents are generally targeted to connexins and/or connexin hemichannels (connexons). Hemichannels and resulting gap junctions that comprise connexins are independently involved in the release or exchange of small molecules between the cell cytoplasm and an extracellular space or tissue in the case of open hemichannels, and between the cytoplasm of adjoining cell in the case of open gap junctions. Thus, an anti-connexin agents provided herein may directly or indirectly reduce coupling and communication between cells or reduce or block communication (or the transmission of molecules) between a cell and extracellular space or tissue, and the modulation of transport of molecules from a cell into an extracellular space or tissue (or from an extracellular space or tissue into a cell) or between adjoining cells is within the scope of anti-connexin agents and embodiments of the invention.

Any anti-connexin agent that is capable of eliciting a desired inhibition of the passage (e.g. transport) of molecules through a gap junction or connexin hemichannel may be used in embodiments of the invention. Any anti-connexin agents that modulates the passage of molecules through a gap junction or connexin hemichannel are also provided in particular embodiments (e.g., those that modulate, block or lessen the passage of molecules from the cytoplasm of a cell into an extracellular space or adjoining cell cytoplasm). Such anti-connexin agents may modulate the passage of molecules through a gap junction or connexin hemichannel with or without gap junction uncoupling (blocking the transport of molecules through gap junctions). Such compounds include, for example, proteins and polypeptides, polynucleotides, and other organic compounds, and they may, for example block the function or expression of a gap junction or a hemichannel in whole or in part, or downregulate the production of a connexin in whole or in part. Certain gap junction inhibitors are listed in Evans, W. H. and Boitano, S. *Biochem. Soc. Trans.* 29: 606-612 (2001).

Certain anti-connexin agents provide downregulation or inhibition of connexin expression (for example, by downregulation of mRNA transcription or translation) or otherwise decrease or inhibit the activity of a connexin protein, a connexin hemichannel or a gap junction. In the case of downregulation, this will have the effect of reducing direct cell-cell communication by gap junctions, or exposure of cell cytoplasm to the extracellular space by hemichannels, at the site at which connexin expression is downregulated.

Examples of anti-connexin agents include agents that decrease or inhibit expression or function of connexin mRNA and/or protein or that decrease activity, expression or formation of a connexin, a connexin hemichannel or a gap junction. Anti-connexin agents include anti-connexin polynucleotides, such as antisense polynucleotides and other polynucleotides (such as polynucleotides having siRNA or ribozyme functionalities), as well as antibodies and binding fragments thereof, and peptides and polypeptides, including peptidomimetics and peptide analogs that modulate hemichannel or gap junction activity or function.

Anti-Connexin Polynucleotides

Anti-connexin polynucleotides include connexin antisense polynucleotides as well as polynucleotides which have functionalities which enable them to downregulate connexin expression. Other suitable anti-connexin polynucleotides include RNAi polynucleotides and siRNA polynucleotides.

Synthesis of antisense polynucleotides and other anti-connexin polynucleotides such as RNAi, siRNA, and ribozyme polynucleotides as well as polynucleotides having modified and mixed backbones is known to those of skill in the art. See e.g. Stein C. A. and Krieg A. M. (eds), Applied Antisense Oligonucleotide Technology, 1998 (Wiley-Liss). Methods of synthesizing antibodies and binding fragments as well as peptides and polypeptides, including peptidomimetics and peptide analogs are known to those of skill in the art. See e.g. Lihu Yang et al., *Proc. Natl. Acad. Sci. U.S.A.*, 1; 95(18): 10836-10841 (Sep. 1, 1998); Harlow and Lane (1988) "Antibodies: A Laboratory Manuel" Cold Spring Harbor Publications, New York; Harlow and Lane (1999) "Using Antibodies" A Laboratory Manuel, Cold Spring Harbor Publications, New York.

According to one aspect, the downregulation of connexin expression may be based generally upon the antisense approach using antisense polynucleotides (such as DNA or RNA polynucleotides), and more particularly upon the use of antisense oligodeoxynucleotides (ODN). These polynucleotides (e.g., ODN) target the connexin protein (s) to be downregulated. Typically the polynucleotides are single stranded, but may be double stranded.

The antisense polynucleotide may inhibit transcription and/or translation of a connexin. Preferably the polynucleotide is a specific inhibitor of transcription and/or translation from the connexin gene or mRNA, and does not inhibit transcription and/or translation from other genes or mRNAs. The product may bind to the connexin gene or mRNA either (i) 5' to the coding sequence, and/or (ii) to the coding sequence, and/or (iii) 3' to the coding sequence.

The antisense polynucleotide is generally antisense to a connexin mRNA. Such a polynucleotide may be capable of hybridizing to the connexin mRNA and may thus inhibit the expression of connexin by interfering with one or more aspects of connexin mRNA metabolism including transcription, mRNA processing, mRNA transport from the nucleus, translation or mRNA degradation. The antisense polynucleotide typically hybridizes to the connexin mRNA to form a duplex which can cause direct inhibition of translation and/or destabilization of the mRNA. Such a duplex may be susceptible to degradation by nucleases.

The antisense polynucleotide may hybridize to all or part of the connexin mRNA. Typically the antisense polynucleotide hybridizes to the ribosome binding region or the coding region of the connexin mRNA. The polynucleotide may be complementary to all of or a region of the connexin mRNA. For example, the polynucleotide may be the exact complement of all or a part of connexin mRNA. However, absolute complementarity is not required and polynucleotides which have sufficient complementarity to form a duplex having a melting temperature of greater than about $20°$ C., $30°$ C. or $40°$ C. under physiological conditions are particularly suitable for use in the present invention.

Thus the polynucleotide is typically a homologue of a sequence complementary to the mRNA. The polynucleotide may be a polynucleotide which hybridizes to the connexin mRNA under conditions of medium to high stringency such as 0.03M sodium chloride and 0.03M sodium citrate at from about $50°$ C. to about $60°$ C.

For certain aspects, suitable polynucleotides are typically from about 6 to 40 nucleotides in length. Preferably a polynucleotide may be from about 12 to about 35 nucleotides in length, or alternatively from about 12 to about 20 nucleotides in length or more preferably from about 18 to about 32 nucleotides in length. According to an alternative aspect, the polynucleotide may be at least about 40, for example at least about 60 or at least about 80, nucleotides in length and up to about 100, about 200, about 300, about 400, about 500, about 1000, about 2000 or about 3000 or more nucleotides in length.

The connexin protein or proteins targeted by the polynucleotide will be dependent upon the site at which downregulation is to be effected. This reflects the non-uniform make-up of gap junction(s) at different sites throughout the body in terms of connexin sub-unit composition. The connexin is a connexin that naturally occurs in a human or animal in one aspect or naturally occurs in the tissue in which connexin expression or activity is to be decreased. The connexin gene (including coding sequence) generally has homology with the coding sequence of one or more of the specific connexins mentioned herein, such as homology with the connexin 43 coding sequence shown in Table 8. The connexin is typically an α or β connexin. Preferably the connexin is an α connexin and is expressed in the tissue to be treated.

Some connexin proteins are however more ubiquitous than others in terms of distribution in tissue. One of the most widespread is connexin 43. Polynucleotides targeted to connexin 43 are particularly suitable for use in the present invention. In other aspects other connexins are targeted.

Anti-connexin polynucleotides include connexin antisense polynucleotides as well as polynucleotides which have functionalities which enable them to downregulate connexin expression. Other suitable anti-connexin polynucleotides include RNAi polynucleotides and SiRNA polynucleotides.

In one preferred aspect, the antisense polynucleotides are targeted to the mRNA of one connexin protein only. Most preferably, this connexin protein is connexin 43. In another aspect, connexin protein is connexin 26, 30, 31.1, 32, 36, 37, 40, or 45. In other aspects, the connexin protein is connexin 30.3, 31, 40.1, or 46.6.

It is also contemplated that polynucleotides targeted to separate connexin proteins be used in combination (for example 1, 2, 3, 4 or more different connexins may be targeted). For example, polynucleotides targeted to connexin 43, and one or more other members of the connexin family (such as connexin 26, 30, 30.3, 31.1, 32, 36, 37, 40, 40.1, 45, and 46.6) can be used in combination.

Alternatively, the antisense polynucleotides may be part of compositions which may comprise polynucleotides to more than one connexin protein. Preferably, one of the connexin proteins to which polynucleotides are directed is connexin 43. Other connexin proteins to which oligodeoxynucleotides are directed may include, for example, connexins 26, 30, 30.3, 31.1, 32, 36, 37, 40, 40.1, 45, and 46.6.

The polynucleotides for use in the invention may suitably be unmodified phosphodiester oligomers. Such oligodeoxynucleotides may vary in length. A 30 mer polynucleotide has been found to be particularly suitable.

Many aspects of the invention are described with reference to oligodeoxynucleotides. However it is understood that other suitable polynucleotides (such as RNA polynucleotides) may be used in these aspects.

The antisense polynucleotides may be chemically modified. This may enhance their resistance to nucleases and may enhance their ability to enter cells. For example, phosphorothioate oligonucleotides may be used. Other deoxynucleotide analogs include methylphosphonates, phosphoramidates, phosphorodithioates, N3'P5'-phosphoramidates and oligoribonucleotide phosphorothioates and their 2'-O-alkyl analogs and 2'-O-methylribonucleotide methylphosphonates. Alternatively mixed backbone oligonucleotides ("MBOs") may be used. MBOs contain segments of phosphothioate oligodeoxynucleotides and appropriately placed segments of modified oligodeoxy- or oligoribonucleotides. MBOs have segments of phosphorothioate linkages and other segments of other modified oligonucleotides, such as methylphosphonate, which is non-ionic, and very resistant to nucleases or 2'-O-alkyloligoribonucleotides. Methods of preparing modified backbone and mixed backbone oligonucleotides are known in the art.

The precise sequence of the antisense polynucleotide used in the invention will depend upon the target connexin protein. In one embodiment, suitable connexin antisense polynucleotides can include polynucleotides such as oligodeoxynucleotides selected from the following sequences set forth in Table 1:

TABLE 1

| Sequence | Target | SEQ ID NO |
|---|---|---|
| 5' GTA ATT GCG GCA AGA AGA ATT GTT TCT GTC 3' | (connexin 43) | (SEQ.ID.NO: 1) |
| 5' GTA ATT GCG GCA GGA GGA ATT GTT TCT GTC 3' | (connexin 43) | (SEQ.ID.NO: 2) |
| 5' GGC AAG AGA CAC CAA AGA CAC TAC CAG CAT 3' | (connexin 43) | (SEQ.ID.NO: 3) |
| 5' TCC TGA GCA ATA CCT AAC GAA CAA ATA 3' | (connexin 26) | (SEQ.ID.NO: 4) |
| 5' CAT CTC CTT GGT GCT CAA CC 3' | (connexin 37) | (SEQ.ID.NO: 5) |
| 5' CTG AAG TCG ACT TGG CTT GG 3' | (connexin 37) | (SEQ.ID.NO: 6) |
| 5' CTC AGA TAG TGG CCA GAA TGC 3' | (connexin 30) | (SEQ.ID.NO: 7) |
| 5' TTG TCC AGG TGA CTC CAA GG 3' | (connexin 30) | (SEQ.ID.NO: 8) |
| 5' CGT CCG AGC CCA GAA AGA TGA GGT C 3' | (connexin 31.1) | (SEQ.ID.NO: 9) |
| 5' AGA GGC GCA CGT GAG ACA C 3' | (connexin 31.1) | (SEQ.ID.NO: 10) |
| 5' TGA AGA CAA TGA AGA TGT T 3' | (connexin 31.1) | (SEQ.ID.NO: 11) |
| 5' TTT CTT TTC TAT GTG CTG TTG GTG A 3' | (connexin 32) | (SEQ.ID.NO: 12) |

Suitable exemplary polynucleotides (and ODNs) directed to various connexins are set forth in Table 1.

Individual antisense polynucleotides may be specific to a particular connexin, or may target 1, 2, 3 or more different connexins. Specific polynucleotides will generally target sequences in the connexin gene or mRNA which are not conserved between connexins, whereas non-specific polynucleotides will target conserved sequences for various connexins.

Suitable polynucleotides for the preparation of the combined polynucleotide compositions described herein include for example, polynucleotides to Connexin Cx43 and polynucleotides for connexins 26, 30, 31.1, 32 and 37 as described in Table 1 above.

Although the precise sequence of the antisense polynucleotide used in the invention will depend upon the target connexin protein, for connexin 43, antisense polynucleotides having the following sequences have been found to be particularly suitable:

```
                                            (SEQ.ID.NO: 1)
    GTA ATT GCG GCA AGA AGA ATT GTT TCT GTC;

(SEQ.ID.NO: 2)
    GTA ATT GCG GCA GGA GGA ATT GTT TCT GTC;
    and (SEQ.ID.NO: 3)
    GGC AAG AGA CAC CAA AGA CAC TAC CAG CAT.
```

For example, suitable antisense polynucleotides for connexins 26, 31.1 and 32 have the following sequences:

```
                                            (SEQ.ID.NO: 4)
    5' TCC TGA GCA ATA CCT AAC GAA CAA ATA (connexin 26);

(SEQ.ID.NO: 9)
    5' CGT CCG AGC CCA GAA AGA TGA GGT C (connexin 31.1);
    and (SEQ.ID.NO: 12)
    5' TTT CTT TTC TAT GTG CTG TTG GTG A (connexin 32).
```

Other connexin antisense polynucleotide sequences useful according to the methods of the present invention include:

```
                                            (SEQ.ID.NO: 5)
    5' CAT CTC CTT GGT GCT CAA CC 3' (connexin 37);

(SEQ.ID.NO: 6)
    5' CTG AAG TCG ACT TGG CTT GG 3' (connexin 37);

(SEQ.ID.NO: 7)
    5' CTC AGA TAG TGG CCA GAA TGC 3' (connexin 30);

(SEQ.ID.NO: 8)
    5' TTG TCC AGG TGA CTC CAA GG 3' (connexin 30);

(SEQ.ID.NO: 10)
    5' AGA GGC GCA CGT GAG ACA C 3' (connexin 31.1);
    and (SEQ.ID.NO: 11)
    5' TGA AGA CAA TGA AGA TGT T 3' (connexin 31.1).
```

Polynucleotides, including ODN's, directed to connexin proteins can be selected in terms of their nucleotide sequence by any convenient, and conventional, approach. For example, the computer programs MacVector and OligoTech (from Oligos etc. Eugene, Oreg., USA) can be used. Once selected, the ODN's can be synthesized using a DNA synthesizer.

Polynucleotide Homologues

Homology and homologues are discussed herein (for example, the polynucleotide may be a homologue of a complement to a sequence in connexin mRNA). Such a polynucleotide typically has at least about 70% homology, preferably at least about 80%, at least about 90%, at least about 95%, at least about 97% or at least about 99% homology with the relevant sequence, for example over a region of at least about 15, at least about 20, at least about 40, at least about 100 more contiguous nucleotides (of the homologous sequence).

Homology may be calculated based on any method in the art. For example the UWGCG Package provides the BESTFIT program which can be used to calculate homology (for example used on its default settings) (Devereux et al (1984) Nucleic Acids Research 12, p 387-395). The PILEUP and BLAST algorithms can be used to calculate homology or line up sequences (typically on their default settings), for example as described in Altschul S. F. (1993) J Mol Evol 36: 290-300; Altschul, S, F et al (1990) J Mol Biol 215: 403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached.

The BLAST algorithm parameters W, T and X determine the sensitivity and speed of the alignment. The BLAST program uses as defaults a word length (W), the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to a second sequence is less than about 1, preferably less than about 0.1, more preferably less than about 0.01, and most preferably less than about 0.001.

The homologous sequence typically differs from the relevant sequence by at least about (or by no more than about) 2, 5, 10, 15, 20 more mutations (which may be substitutions, deletions or insertions). These mutations may be measured across any of the regions mentioned above in relation to calculating homology.

The homologous sequence typically hybridizes selectively to the original sequence at a level significantly above background. Selective hybridization is typically achieved using conditions of medium to high stringency (for example 0.03M sodium chloride and 0.03M sodium citrate at from about 50° C. to about 60° C.). However, such hybridization may be carried out under any suitable conditions known in the art (see Sambrook et al. (1989), Molecular Cloning: A Laboratory Manual). For example, if high stringency is required, suitable conditions include 0.2×SSC at 60° C. If lower stringency is required, suitable conditions include 2×SSC at 60° C.

Peptide and Polypeptide Anti-Connexin Agents

Binding proteins, including peptides, peptidomimetics, antibodies, antibody fragments, and the like, are also suitable modulators of gap junctions and hemichannels.

Binding proteins include, for example, monoclonal antibodies, polyclonal antibodies, antibody fragments (including, for example, Fab, F(ab')$_2$ and Fv fragments; single chain antibodies; single chain Fvs; and single chain binding molecules such as those comprising, for example, a binding domain, hinge, CH2 and CH3 domains, recombinant antibodies and antibody fragments which are capable of binding an antigenic determinant (i.e., that portion of a molecule, generally referred to as an epitope) that makes contact with a particular antibody or other binding molecule. These binding proteins, including antibodies, antibody fragments, and so on, may be chimeric or humanized or otherwise made to be less immunogenic in the subject to whom they are to be administered, and may be synthesized, produced recombinantly, or produced in expression libraries. Any binding molecule known in the art or later discovered is envisioned, such as those referenced herein and/or described in greater detail in the art. For example, binding proteins include not only antibodies, and the like, but also ligands, receptors, peptidomimetics, or other binding fragments or molecules (for example, produced by phage display) that bind to a target (e.g. connexin, hemichannel, or associated molecules).

Binding molecules will generally have a desired specificity, including but not limited to binding specificity, and desired affinity. Affinity, for example, may be a $K_a$ of greater than or equal to about $10^4$ $M^{-1}$, greater than or equal to about $10^6$ $M^{-1}$, greater than or equal to about $10^7$ $M^{-1}$, greater than or equal to about $10^8$ $M^{-1}$. Affinities of even greater than about $10^8$ $M^{-1}$ are suitable, such as affinities equal to or greater than about $10^9$ $M^{-1}$, about $10^{10}$ $M^{-1}$, about $10^{11}$ $M^{-1}$, and about $10^{12}$ $M^{-1}$. Affinities of binding proteins according to the present invention can be readily determined using conventional techniques, for example those described by Scatchard et al., 1949 *Ann. N.Y. Acad. Sci.* 51: 660.

By using data obtained from hydropathy plots, it has been proposed that a connexin contains four-transmembrane-spanning regions and two short extra-cellular loops. The positioning of the first and second extracellular regions of connexin was further characterized by the reported production of anti-peptide antibodies used for immunolocalization of the corresponding epitopes on split gap junctions. Goodenough D. A. *J Cell Biol* 107: 1817-1824 (1988); Meyer R. A., *J Cell Biol* 119: 179-189 (1992).

The extracellular domains of a hemichannel contributed by two adjacent cells "dock" with each other to form complete gap junction channels. Reagents that interfere with the interactions of these extracellular domains can impair cell-to-cell communication. Peptide inhibitors of gap junctions and hemichannels have been reported. See for example Berthoud, V. M. et al., *Am J. Physiol. Lung Cell Mol. Physiol.* 279: L619-L622 (2000); Evans, W. H. and Boitano, S. *Biochem. Soc. Trans.* 29: 606-612, and De Vriese A. S., et al. *Kidney Int.* 61: 177-185 (2001). Short peptides corresponding to sequences within the extracellular loops of connexins were said to inhibit intercellular communication. Boitano S. and Evans W. *Am J Physiol Lung Cell Mol Physiol* 279: L623-L630 (2000). The use of peptides as inhibitors of cell-cell channel formation produced by connexin (Cx) 32 expressed in paired *Xenopus* oocytes has also been reported. Dahl G, et al., *Biophys J* 67: 1816-1822 (1994). Berthoud, V. M. and Seul, K. H., summarized some of these results. *Am J., Physiol. Lung Cell Mol. Physiol.* 279: L619-L622 (2000).

Anti-connexin agents include peptides comprising an amino acid sequence corresponding to a transmembrane region (e.g. 1$^{st}$ to 4$^{th}$) of a connexin (e.g. connexin 45, 43, 26, 30, 31.1, and 37). Anti-connexin agents may comprise a peptide comprising an amino acid sequence corresponding to a portion of a transmembrane region of a connexin 45. Anti-connexin agents include a peptide having an amino acid sequence that comprises about 5 to 20 contiguous amino acids of SEQ.ID.NO:13, a peptide having an amino acid sequence that comprises about 8 to 15 contiguous amino acids of SEQ.ID.NO:13, or a peptide having an amino acid sequence that comprises about 11 to 13 contiguous amino acids of SEQ.ID.NO:13. Other embodiments are directed to an anti-connexin agent that is a peptide having an amino acid sequence that comprises at least about 5, at least about 6, at least about 7, at least about 8, at least about 9, at least about 10, at least about 11, at least about 12, at least about 13, at least about 14, at least about 15, at least about 20, at least about 25, or at least about 30 contiguous amino acids of SEQ.ID.NO:13. In certain anti-connexin agents provided herein, the extracellular domains of connexin 45 corresponding to the amino acids at positions 46-75 and 199-228 of SEQ ID NO: 13 may be used to develop the particular peptide sequences. Certain peptides described herein have an amino acid sequence corresponding to the regions at positions 46-75 and 199-228 of SEQ.ID.NO: 13. The peptides need not have an amino acid sequence identical to those portions of SEQ.ID.NO: 13, and conservative amino acid changes may be made such that the peptides retain binding activity or functional activity. Alternatively, the peptide may target regions of the connexin protein other than the extracellular domains (e.g. the portions of SEQ.ID.NO:13 not corresponding to positions 46-75 and 199-228).

Also, suitable anti-connexin agents comprise a peptide comprising an amino acid sequence corresponding to a portion of a transmembrane region of a connexin 43. Anti-connexin agents include peptides having an amino acid sequence that comprises about 5 to 20 contiguous amino acids of SEQ.ID.NO:14, peptides having an amino acid sequence that comprises about 8 to 15 contiguous amino acids of SEQ.ID.NO:14, or peptides having an amino acid sequence that comprises about 11 to 13 contiguous amino acids of SEQ.ID.NO:14. Other anti-connexin agents include a peptide having an amino acid sequence that comprises at least about 5, at least about 6, at least about 7, at least about 8, at least about 9, at least about 10, at least about 11, at least about 12, at least about 13, at least about 14, at least about 15, at least about 20, at least about 25, or at least about 30 contiguous amino acids of SEQ.ID.NO:14. Other anti-connexin agents comprise the extracellular domains of connexin 43 corresponding to the amino acids at positions 37-76 and 178-208 of SEQ.ID.NO: 14. Anti-connexin agents include peptides described herein which have an amino acid sequence corresponding to the regions at positions 37-76 and 178-208 of SEQ.ID.NO: 14. The peptides need not have an amino acid sequence identical to those portions of SEQ.ID.NO: 14, and conservative amino acid changes may be made such that the peptides retain binding activity or functional activity. Alternatively, peptides may target regions of the connexin protein other than the extracellular domains (e.g. the portions of SEQ.ID.NO:14 not corresponding to positions 37-76 and 178-208).

Connexin 45

(SEQ ID NO. 13)

```
Met Ser Trp Ser Phe Leu Thr Arg Leu Leu Glu Glu Ile His Asn His
1               5                   10                  15

Ser Thr Phe Val Gly Lys Ile Trp Leu Thr Val Leu Ile Val Phe Arg
                20                  25                  30

Ile Val Leu Thr Ala Val Gly Gly Glu Ser Ile Tyr Tyr Asp Glu Gln
                35                  40                  45

Ser Lys Phe Val Cys Asn Thr Glu Gln Pro Gly Cys Glu Asn Val Cys
50                          55                  60

Tyr Asp Ala Phe Ala Pro Leu Ser His Val Arg Phe Trp Val Phe Gln
65                  70                  75                  80

Ile Ile Leu Val Ala Thr Pro Ser Val Met Tyr Leu Gly Tyr Ala Ile
                85                  90                  95

His Lys Ile Ala Lys Met Glu His Gly Glu Ala Asp Lys Lys Ala Ala
                100                 105                 110

Arg Ser Lys Pro Tyr Ala Met Arg Trp Lys Gln His Arg Ala Leu Glu
                115                 120                 125

Glu Thr Glu Glu Asp Asn Glu Glu Asp Pro Met Met Tyr Pro Glu Met
130                         135                 140

Glu Leu Glu Ser Asp Lys Glu Asn Lys Glu Gln Ser Gln Pro Lys Pro
145                 150                 155                 160

Lys His Asp Gly Arg Arg Ile Arg Glu Asp Gly Leu Met Lys Ile
                165                 170                 175

Tyr Val Leu Gln Leu Leu Ala Arg Thr Val Phe Glu Val Gly Phe Leu
                180                 185                 190

Ile Gly Gln Tyr Phe Leu Tyr Gly Phe Gln Val His Pro Phe Tyr Val
                195                 200                 205

Cys Ser Arg Leu Pro Cys Pro His Lys Ile Asp Cys Phe Ile Ser Arg
                210                 215                 220

Pro Thr Glu Lys Thr Ile Phe Leu Leu Ile Met Tyr Gly Val Thr Gly
225                 230                 235                 240

Leu Cys Leu Leu Leu Asn Ile Trp Glu Met Leu His Leu Gly Phe Gly
                245                 250                 255

Thr Ile Arg Asp Ser Leu Asn Ser Lys Arg Arg Glu Leu Glu Asp Pro
                260                 265                 270

Gly Ala Tyr Asn Tyr Pro Phe Thr Trp Asn Thr Pro Ser Ala Pro Pro
                275                 280                 285

Gly Tyr Asn Ile Ala Val Lys Pro Asp Gln Ile Gln Tyr Thr Glu Leu
                290                 295                 300

Ser Asn Ala Lys Ile Ala Tyr Lys Gln Asn Lys Ala Asn Thr Ala Gln
305                 310                 315                 320

Glu Gln Gln Tyr Gly Ser His Glu Glu Asn Leu Pro Ala Asp Leu Glu
                325                 330                 335

Ala Leu Gln Arg Glu Ile Arg Met Ala Gln Glu Arg Leu Asp Leu Ala
                340                 345                 350

Val Gln Ala Tyr Ser His Gln Asn Asn Pro His Gly Pro Arg Glu Lys
                355                 360                 365

Lys Ala Lys Val Gly Ser Lys Ala Gly Ser Asn Lys Ser Thr Ala Ser
                370                 375                 380

Ser Lys Ser Gly Asp Gly Lys Asn Ser Val Trp Ile
385                 390                 395
```

```
Connexin 43
                                                         (SEQ ID NO. 14)
Met Gly Asp Trp Ser Ala Leu Gly Lys Leu Leu Asp Lys Val Gln Ala
1               5                   10                  15

Tyr Ser Thr Ala Gly Gly Lys Val Trp Leu Ser Val Leu Phe Ile Phe
                20                  25                  30

Arg Ile Leu Leu Gly Thr Ala Val Glu Ser Ala Trp Gly Asp Glu
            35                  40                  45

Gln Ser Ala Phe Arg Cys Asn Thr Gln Gln Pro Gly Cys Glu Asn Val
    50                  55                  60

Cys Tyr Asp Lys Ser Phe Pro Ile Ser His Val Arg Phe Trp Val Leu
65                  70                  75                  80

Gln Ile Ile Phe Val Ser Val Pro Thr Leu Leu Tyr Leu Ala His Val
                85                  90                  95

Phe Tyr Val Met Arg Lys Glu Glu Lys Leu Asn Lys Lys Glu Glu Glu
                100                 105                 110

Leu Lys Val Ala Gln Thr Asp Gly Val Asn Val Asp Met His Leu Lys
            115                 120                 125

Gln Ile Glu Ile Lys Lys Phe Lys Tyr Gly Ile Glu Glu His Gly Lys
    130                 135                 140

Val Lys Met Arg Gly Gly Leu Leu Arg Thr Tyr Ile Ile Ser Ile Leu
145                 150                 155                 160

Phe Lys Ser Ile Phe Glu Val Ala Phe Leu Leu Ile Gln Trp Tyr Ile
                165                 170                 175

Tyr Gly Phe Ser Leu Ser Ala Val Tyr Thr Cys Lys Arg Asp Pro Cys
            180                 185                 190

Pro His Gln Val Asp Cys Phe Leu Ser Arg Pro Thr Glu Lys Thr Ile
    195                 200                 205

Phe Ile Ile Phe Met Leu Val Val Ser Leu Val Ser Leu Ala Leu Asn
                210                 215                 220

Ile Ile Glu Leu Phe Tyr Val Phe Phe Lys Gly Val Lys Asp Arg Val
225                 230                 235                 240

Lys Gly Lys Ser Asp Pro Tyr His Ala Thr Ser Gly Ala Leu Ser Pro
                245                 250                 255

Ala Lys Asp Cys Gly Ser Gln Lys Tyr Ala Tyr Phe Asn Gly Cys Ser
            260                 265                 270

Ser Pro Thr Ala Pro Leu Ser Pro Met Ser Pro Pro Gly Tyr Lys Leu
    275                 280                 285

Val Thr Gly Asp Arg Asn Asn Ser Ser Cys Arg Asn Tyr Asn Lys Gln
    290                 295                 300

Ala Ser Glu Gln Asn Trp Ala Asn Tyr Ser Ala Glu Gln Asn Arg Met
305                 310                 315                 320

Gly Gln Ala Gly Ser Thr Ile Ser Asn Ser His Ala Gln Pro Phe Asp
            325                 330                 335

Phe Pro Asp Asp Asn Gln Asn Ser Lys Lys Leu Ala Ala Gly His Glu
            340                 345                 350

Leu Gln Pro Leu Ala Ile Val Asp Gln Arg Pro Ser Ser Arg Ala Ser
    355                 360                 365

Ser Arg Ala Ser Ser Arg Pro Arg Pro Asp Asp Leu Glu Ile
    370                 375                 380
```

The anti-connexin peptides may comprise sequences corresponding to a portion of the connexin extracellular domains with conservative amino acid substitutions such that peptides are functionally active anti-connexin agents. Exemplary conservative amino acid substitutions include for example the substitution of a nonpolar amino acid with another nonpolar amino acid, the substitution of an aromatic amino acid with another aromatic amino acid, the substitution of an aliphatic amino acid with another aliphatic amino acid, the substitution of a polar amino acid with another polar amino acid, the substitution of an acidic amino acid with another acidic amino acid, the substitution of a basic amino acid with another basic amino acid, and the substitution of an ionizable amino acid with another ionizable amino acid.

Exemplary peptides targeted to connexin 43 are shown below in Table 2. M1, 2, 3 and 4 refer to the 1$^{st}$ to 4$^{th}$ transmembrane regions of the connexin 43 protein respectively. E1 and E2 refer to the first and second extracellular loops respectively.

TABLE 2

Peptidic Inhibitors of Intercellular Communication (cx43)

| | | |
|---|---|---|
| FEVAFLLIQWI | M3 & E2 | (SEQ.ID.NO: 15) |
| LLIQWYIGFSL | E2 | (SEQ.ID.NO: 16) |
| SLSAVYTCKRDPCPHQ | E2 | (SEQ.ID.NO: 17) |
| VDCFLSRPTEKT | E2 | (SEQ.ID.NO: 18) |
| SRPTEKTIFII | E2 & M4 | (SEQ.ID.NO: 19) |
| LGTAVESAWGDEQ | M1 & E1 | (SEQ.ID.NO: 20) |
| QSAFRCNTQQPG | E1 | (SEQ.ID.NO: 21) |
| QQPGCENVCYDK | E1 | (SEQ.ID.NO: 22) |
| VCYDKSFPISHVR | E1 | (SEQ.ID.NO: 23) |

Table 3 provides additional exemplary connexin peptides used in inhibiting hemichannel or gap junction function. In other embodiments, conservative amino acid changes are made to the peptides or fragments thereof.

TABLE 3

Additional Peptidic Inhibitors of Intercellular Communication (cx32, cx43)

| Connexin | Location | | AA's and Sequence | |
|---|---|---|---|---|
| Cx32 | E1 | 39-77 | AAESVWGDEIKSSFICNTLQPGCNSVCYDHFFPISHVR | (SEQ.ID.NO: 24) |
| Cx32 | E1 | 41-52 | ESVWGDEKSSFI | (SEQ.ID.NO: 25) |
| Cx32 | E1 | 52-63 | ICNTLQPGCNSV | (SEQ.ID.NO: 26) |
| Cx32 | E1 | 62-73 | SVCYDHFFPISH | (SEQ.ID.NO: 27) |
| Cx32 | E2 | 64-188 | RLVKCEAFPCPNTVDCFVSRPTEKT | (SEQ.ID.NO: 28) |
| Cx32 | E2 | 166-177 | VKCEAFPCPNTV | (SEQ.ID.NO: 29) |
| Cx32 | E2 | 177-188 | VDCFVSRPTEKT | (SEQ.ID.NO: 30) |
| Cx32 | E1 | 63-75 | VCYDHFFPISHVR | (SEQ.ID.NO: 31) |
| Cx32 | E1 | 45-59 | VWGDEKSSFICNTLQPGY | (SEQ.ID.NO: 32) |
| Cx32 | E1 | 46-59 | DEKSSFICNTLQPGY | (SEQ.ID.NO: 33) |
| Cx32 | E2 | 182-192 | SRPTEKTVFTV | (SEQ.ID.NO: 34) |
| Cx32/Cx43 | E2 | 182-188/ 201-207 | SRPTEKT | (SEQ.ID.NO: 35) |
| Cx32 | E1 | 52-63 | ICNTLQPGCNSV | (SEQ.ID.NO: 36) |
| Cx40 | E2 | 177-192 | FLDTLHVCRRSPCPHP | (SEQ.ID.NO: 37) |
| Cx43 | E2 | 188-205 | KRDPCHQVDCFLSRPTEK | (SEQ.ID.NO: 38) |

Table 4 provides the extracellular loops for connexin family members which are used to develop peptide inhibitors for use as described herein. The peptides and provided in Table 4, and fragments thereof, are used as peptide inhibitors in certain non-limiting embodiments. In other non-limiting embodiments, peptides comprising from about 8 to about 15, or from about 11 to about 13 amino contiguous amino acids of the peptides in this Table 4 are peptide inhibitors. Conservative amino acid changes may be made to the peptides or fragments thereof.

TABLE 4

| Extracellular loops for various connexin family members | | |
|---|---|---|
| E1 | | |
| huCx26 | KEVWGDEQADFVCNTLQPGCKNVCYDHYFPISHIR | (SEQ.ID.NO: 39) |
| huCx30 | QEVWGDEQEDFVCNTLQPGCKNVCYDHFFPVSHIR | (SEQ.ID.NO: 40) |
| huCx30.3 | EEVWDDEQKDFVCNTKQPGCPNVCYDEFFPVSHVR | (SEQ.ID.NO: 41) |
| huCx31 | ERVWGDEQKDFDCNTKQPGCTNVCYDNYFPISNIR | (SEQ.ID.NO: 42) |
| huCx31.1 | ERVWSDDHKDFDCNTRQPGCSNVCFDEFFPVSHVR | (SEQ.ID.NO: 43) |
| huCx32 | ESVWGDEKSSFICNTLQPGCNSVCYDQFFPISHVR | (SEQ.ID.NO: 44) |
| huCx36 | ESVWGDEQSDFECNTAQPGCTNVCYDQAFPISHIR | (SEQ.ID.NO: 45) |
| huCx37 | ESVWGDEQSDFECNTAQPGCTNVCYDQAFPISHIR | (SEQ.ID.NO: 46) |
| huCx40.1 | RPVYQDEQERFVCNTLQPGCANVCYDVFSPVSHLR | (SEQ.ID.NO: 47) |
| huCx43 | ESAWGDEQSAFRCNTQQPGCENVCYDKSFPISHVR | (SEQ.ID.NO: 48) |
| huCx46 | EDVWGDEQSDFTCNTQQPGCBNVCYBRAFPISHIR | (SEQ.ID.NO: 49) |
| huCx46.6 | EAIYSDEQAKFTCNTRQPGCDNVCYDAFAPLSHVR | (SEQ.ID.NO: 50) |
| huCx40 | ESSWGDEQADFRCDTIQPGCQNVCTDQAFPISHIR | (SEQ.ID.NO: 51) |
| huCx45 | GESIYYDEQSKFVCNTEQPGCENVCYDAFAPLSHVR | (SEQ.ID.NO: 52) |
| E2 | | |
| huCx26 | MYVFYVMYDGFSMQRLVKCNAWPCPNTVDCFVSRPTEKT | (SEQ.ID.NO: 53) |
| huCx30 | MYVFYFLYNGYHLPWVLKCGIDPCPNLVDCFISRPTEKT | (SEQ.ID.NO: 54) |
| huCx30.3 | LYIFHRLYKDYDMPRVVACSVEPCPHTVDCYISRPTEKK | (SEQ.ID.NO: 55) |
| huCx31 | LYLLHTLWHGFNMPRLVQCANVAPCPNIVDCYIARPTEKK | (SEQ.ID.NO: 56) |
| huCx31.1 | LYVFHSFYPKYILPPVVKCHADPCPNIVDCFISKPSEKN | (SEQ.ID.NO: 57) |
| huCx32 | MYVFYLLYPGYAMVRLVKCDVYPCPNTVDCFVSRPTEKT | SEQ.ID.NO: 58) |
| huCx36 | LYGWTMEPVFVCQRAPCPYLVDCFVSRPTEKT | (SEQ.ID.NO: 59) |
| huCx37 | LYGWTMEPVFVCQRAPCPYLVDCFVSRPTEKT | (SEQ.ID.NO: 60) |
| huCx40.1 | GALHYFLFGFLAPKKFPCTRPPCTGVVDCYVSRPTSKS | (SEQ.ID.NO: 61) |
| huCx43 | LLIQWYIYGFSLSAVYTCKRDPCPHQVDCFLSRPTEKT | (SEQ.ID.NO: 62) |
| huCx46 | IAGQYFLYGFELKPLYRCDRWPCPNTVDCFISRPTEKT | (SEQ.ID.NO: 63) |
| huCx46.6 | LVGQYLLYGFEVRPFFPCSRQPCPHVVDCFVSRPTEKT | (SEQ.ID.NO: 64) |
| huCx40 | IVGQYFIYGIFLTTLHVCRRSPCPHPVNCYVSRPTEKN | (SEQ.ID.NO: 65) |
| huCx45 | LIGQYFLYGFQVHPFYVCSRLPCHPKIDCFISRPTEKT | (SEQ.ID.NO: 66) |

Table 5 provides the extracellular domain for connexin family members which may be used to develop peptide anti-connexin agents. The peptides and provided in Table 5, and fragments thereof, may also be used as peptide anti-connexin agents. Such peptides may comprise from about 8 to about 15, or from about 11 to about 13 amino contiguous amino acids of the peptide sequence in this Table 5. Conservative amino acid changes may be made to the peptides or fragments thereof.

TABLE 5

| Extracellular domains | | |
|---|---|---|
| Peptide | VDCFLSRPTEKT | (SEQ.ID.NO: 18) |
| Peptide | SRPTEKTIFII | (SEQ.ID.NO: 19) |
| huCx43 | LLIQWYIYGFSLSAVYTCKRDPCPHQVDCFLSRPTEKTIFII | (SEQ.ID.NO: 67) |
| huCx26 | MYVFYVMYDGFSMQRLVKCNAWPCPNTVDCFVSRPTEKTVFTV | (SEQ.ID.NO: 68) |
| huCx30 | YVFYFLYNGYHLPWVLKCGIDPCPNLVDCFISRPTEKTVFTI | (SEQ.ID.NO: 69) |
| huCx30.3 | LYIFHRLYKDYDMPRVVACSVEPCPHTVDCYISRPTEKKVFTY | (SEQ.ID.NO: 70) |
| huCx31 | LYLLHTLWHGFNMPRLVQCANVAPCPNIVDCYIARPTEKKTY | (SEQ.ID.NO: 71) |
| huCx31.1 | LYVFHSFYPKYILPPVVKCHADPCPNIVDCFISKPSEKNIFTL | (SEQ.ID.NO: 72) |
| huCx32 | MYVFYLLYPGYAMVRLVKCDVYPCPNTVDCFVSRPTEKTVFTV | (SEQ.ID.NO: 73) |
| huCx36 | LYGWTMEPVFVCQRAPCPYLVDCFVSRPTEKTIFII | (SEQ.ID.NO: 74) |
| huCx37 | LYGWTMEPVFVCQRAPCPYLVDCFVSRPTEKTIFII | (SEQ.ID.NO: 75) |
| huCx40.1 | GALHYFLFGFLAPKKFPCTRPPCTGVVDCYVSRPTEKSLLML | (SEQ.ID.NO: 76) |
| huCx46 | IAGQYFLYGFELKPLYRCDRWPCPNTVDCFISRPTEKTIFII | (SEQ.ID.NO: 77) |
| huCx46.6 | LVGQYLLYGFEVRPFFPCSRQPCPHVVDCFVSRPTEKTVFLL | (SEQ.ID.NO: 78) |
| huCx40 | IVGQYFIYGIFLTTLHVCRRSPCPHPVNCYSRPTEKNVFIV | (SEQ.ID.NO: 79) |
| huCx45 | LIGQYFLYGFQVHPFYVCSRLPCHPKIDCFISRPTEKTIFLL | (SEQ.ID.NO: 80) |

Table 6 provides peptides inhibitors of connexin 40 shown with reference to the extracellular loops (E1 and E2) of connexin 40. The bold amino acids are directed to the transmembrane regions of connexin 40.

TABLE 6

| Cx40 peptide inhibitors | | |
|---|---|---|
| E2 | LGTAAESSWGDEQADFRCDTIQPGCQNVCTDQAFPISHIRFWVLQ | (SEQ.ID.NO: 81) |
| | LGTAAESSWGDEQA | (SEQ.ID.NO: 82) |
| | DEQADFRCDTIQP | (SEQ.ID.NO: 83) |
| | TIQPGCQNVCTDQ | (SEQ.ID.NO: 84) |
| | VCTDQAFPISHIR | (SEQ.ID.NO: 85) |
| | AFPISHIRFWVLQ | (SEQ.ID.NO: 86) |
| E2 | MEVGFIVGQYFIYGIFLTTLHVCRRSPCPHPVNCYVSRPTEKNVFIV | (SEQ.ID.NO: 87) |
| | MEVGFIVGQYF | (SEQ.ID.NO: 88) |
| | IVGQYFIYGIFL | (SEQ.ID.NO: 89) |
| | GIFLTTLHVCRRSP | (SEQ.ID.NO: 90) |
| | RRSPCPHPVNCY | (SEQ.ID.NO: 91) |
| | VNCYVSRPTEKN | (SEQ.ID.NO: 92) |
| | SRPTEKNVFIV | (SEQ.ID.NO: 93) |

Table 7 provides peptides inhibitors of connexin 45 shown with reference to the extracellular loops (E1 and E2) of connexin 45. The bold amino acids are directed to the transmembrane regions of connexin 45

TABLE 7

Cx45 peptide inhibitors

| | | |
|---|---|---|
| E1 | LTAVGGESIYYDEQSKFVCNTEQPGCENVCYDAFAPLSHVRFWVFQ | (SEQ.ID.NO: 94) |
| | LTAVGGESIYYDEQS | (SEQ.ID.NO: 95) |
| | DEQSKFVCNTEQP | (SEQ.ID.NO: 96) |
| | TEQPGCENVCYDA | (SEQ.ID.NO: 97) |
| | VCYDAFAPLSHVR | (SEQ.ID.NO: 98) |
| | APLSHVRFWVFQ | (SEQ.ID.NO: 99) |
| E2 | FEVGFLIGQYFLYGFQVHPFYVCSRLPCHPKIDCFISRPTEKTIFLL | (SEQ.ID.NO: 100) |
| | FEVGFLIGQYF | (SEQ.ID.NO: 101) |
| | LIGQYFLYGFQV | (SEQ.ID.NO: 102) |
| | GFQVHPFYVCSRLP | (SEQ.ID.NO: 103) |
| | SRLPCHPKIDCF | (SEQ.ID.NO: 104) |
| | IDCFISRPTEKT | (SEQ.ID.NO: 105) |
| | SRPTEKTIFLL | (SEQ.ID.NO: 106) |

In certain embodiments, it is preferred that certain peptide inhibitors block hemichannels without disrupting existing gap junctions. While not wishing to be bound to any particular theory or mechanism, it is also believed that certain peptidomimetics (e.g. VCYDKSFPISHVR, (SEQ.ID.NO: 23) block hemichannels without causing uncoupling of gap junctions (See Leybeart et al., *Cell Commun. Adhes.* 10: 251-257 (2003)), or do so in lower dose amounts. The peptide SRPTEKTIFII (SEQ.ID.NO: 19) may also be used, for example to block hemichannels without uncoupling of gap junctions. The peptide SRGGEKNVFIV (SEQ.ID.NO: 107) may be used that as a control sequence (DeVriese et al., *Kidney Internat.* 61: 177-185 (2002)). Examples of peptide inhibitors for connexin 45 YVCSRLPCHP (SEQ.ID.NO:108), QVHPFYVCSRL (SEQ.ID.NO: 109), FEVGFLIGQYFLY (SEQ.ID.NO:110), GQYFLYGFQVHP (SEQ.ID.NO:111), GFQVHPFYVCSR (SEQ.ID.NO:112), AVGGESIYYDEQ (SEQ.ID.NO:113), YDEQSKFVCNTE (SEQ.ID.NO:114), NTEQPGCENVCY (SEQ.ID.NO:115), CYDAFAPLSHVR (SEQ.ID.NO:116), FAPLSHVRFWVF (SEQ.ID.NO:117) and LIGQY (SEQ.ID.NO:118), QVHPF (SEQ.ID.NO:119), YVCSR (SEQ.ID.NO:120), SRLPC (SEQ.ID.NO:121), LPCHP (SEQ.ID.NO:122) and GESIY (SEQ.ID.NO:123), YDEQSK (SEQ.ID.NO:124), SKFVCN (SEQ.ID.NO:125), TEQPGCEN (SEQ.ID.NO:126), VCYDAFAP (SEQ.ID.NO:127), LSHVRFWVFQ (SEQ.ID.NO:128) The peptides may only be 3 amino acids in length, including SRL, PCH, LCP, CHP, IYY, SKF, QPC, VCY, APL, HVR, or longer, for example: LIQYFLYGFQVHPF (SEQ.ID.NO: 129), VHPFYCSRLPCHP (SEQ.ID.NO:130), VGGESIYYDEQSKFVCNTEQPG (SEQ.ID.NO:131), TEQPGCENVCYDAFAPLSHVRF (SEQ.ID.NO:132), AFAPLSHVRFWVFQ (SEQ.ID.NO: 133).

Table 8

TABLE 8A

Human Connexin 43 from GenBank Accession No. M65188 (SEQ.ID.NO: 134)

| | | | | |
|---|---|---|---|---|
| 1 | ggcttttagc | gtgaggaaag | taccaaacag | cagcggagtt ttaaacttta aatagacagg |
| 61 | tctgagtgcc | tgaacttgcc | ttttcattt | acttcatcct ccaaggagtt caatcacttg |
| 121 | gcgtgacttc | actactttta | agcaaaagag | tggtgcccag gcaacatggg tgactggagc |
| 181 | gccttaggca | aactccttga | caaggttcaa | gcctactcaa ctgctggagg gaaggtgtgg |
| 241 | ctgtcagtac | ttttcatttt | ccgaatcctg | ctgctgggga cagcggttga gtcagcctgg |
| 301 | ggagatgagc | agtctgcctt | tcgttgtaac | actcagcaac ctggttgtga aaatgtctgc |
| 361 | tatgacaagt | ctttcccaat | ctctcatgtg | cgcttctggg tcctgcagat catatttgtg |
| 421 | tctgtaccca | cactcttgta | cctggctcat | gtgttctatg tgatgcgaaa ggaagagaaa |
| 481 | ctgaacaaga | aagaggaaga | actcaaggtt | gcccaaactg atggtgtcaa tgtggacatg |

TABLE 8A-continued

Human Connexin 43 from GenBank Accession No. M65188 (SEQ.ID.NO: 134)

```
 541 cacttgaagc agattgagat aaagaagttc aagtacggta ttgaagagca tggtaaggtg
 601 aaaatgcgag gggggttgct gcgaacctac atcatcagta tcctcttcaa gtctatcttt
 661 gaggtggcct tcttgctgat ccagtggtac atctatggat tcagcttgag tgctgtttac
 721 acttgcaaaa gagatccctg cccacatcag gtggactgtt tcctctctcg ccccacggag
 781 aaaccatct tcatcatctt catgctggtg gtgtccttgg tgtccctggc cttgaatatc
 841 attgaactct tctatgtttt cttcaagggc gttaaggatc gggttaaggg aaagagcgac
 901 ccttaccatg cgaccagtgg tgcgctgagc cctgccaaag actgtgggtc tcaaaaatat
 961 gcttatttca atgctgctc ctcaccaacc gctcccctct cgcctatgtc tcctcctggg
1021 tacaagctgg ttactggcga cagaaacaat tcttcttgcc gcaattacaa caagcaagca
1081 agtgagcaaa actgggctaa ttacagtgca gaacaaaatc gaatggggca ggcgggaagc
1141 accatctcta actcccatgc acagccttt gatttccccg atgataacca gaattctaaa
1201 aaactagctg ctggacatga attacagcca ctagccattg tggaccagcg accttcaagc
1261 agagccagca gtcgtgccag cagcagacct cggcctgatg acctggagat ctag
```

TABLE 8B

Human Connexin 43 (SEQ.ID.NO: 135)

```
   1 atgggtgact ggagcgcctt aggcaaactc cttgacaagg ttcaagccta ctcaactgct
  61 ggagggaagg tgtggctgtc agtacttttc attttccgaa tcctgctgct ggggacagcg
 121 gttgagtcag cctggggaga tgagcagtct gcctttcgtt gtaacactca gcaacctggt
 181 tgtgaaaatg tctgctatga caagtctttc ccaatctctc atgtgcgctt ctgggtcctg
 241 cagatcatat ttgtgtctgt acccacactc ttgtacctgg ctcatgtgtt ctatgtgatg
 301 cgaaaggaag agaaactgaa caagaaagag gaagaactca aggttgccca aactgatggt
 361 gtcaatgtgg acatgcactt gaagcagatt gagataaaga agttcaagta cggtattgaa
 421 gagcatggta aggtgaaaat gcgagggggg ttgctgcgaa cctacatcat cagtatcctc
 481 ttcaagccta tctttgaggt ggccttcttg ctgatccagt ggtacatcta tggattcagc
 541 ttgagtgctg tttacacttg caaaagagat ccctgcccac atcaggtgga ctgtttcctc
 601 tctcgcccca cggagaaaac catcttcatc atcttcatgc tggtggtgtc cttggtgtcc
 661 ctggccttga atatcattga actcttctat gttttcttca agggcgttaa ggatcgggtt
 721 aagggaaaga gcgaccctta ccatgcgacc agtggtgcgc tgagccctgc aaagactgt
 781 gggtctcaaa aatatgctta tttcaatggc tgctcctcac caaccgctcc cctctcgcct
 841 atgtctcctc ctgggtacaa gctggttact ggcgacagaa acaattcttc ttgccgcaat
 901 tacaacaagc aagcaagtga gcaaaactgg gctaattaca gtgcagaaca aaatcgaatg
 961 gggcaggcgg gaagcaccat ctctaactcc catgcacagc cttttgattt ccccgatgat
1021 aaccagaatt ctaaaaaact agctgctgga catgaattac agccactagc cattgtggac
1081 cagcgacctt caagcagagc cagcagtcgt gccagcagca gacctcggcc tgatgacctg
1141 gagatctag
```

Therapeutic Agents

Therapeutic agents include pharmaceutically acceptable agents useful in the treatment of wounds or the promotion of wound-healing, whether currently existing and known or later developed. Therapeutic agents include, for example, anti-infectives, anesthetics, analgesics, antibiotics, narcotics, and steroidal and non-steroidal anti-inflammatory agents. Preferred therapeutic agents include topical steroid anti-inflammatory agents, antimicrobial agents, local and topical anesthetics, and topical opioids.

Therapeutic agents may include, for example, anti-thrombogenic agents, anticoagulants, antiplatelet agents, thrombolytics, antiproliferatives, anti-inflammatory agents, statins, α-adrenergic receptor antagonists, $β_1$-selective adrenergic antagonists, ACE inhibitors, calcium channel blockers, angiotensin II receptor antagonists, vasodilators, anti-proliferative/antimitotic agents, immunosuppressive agent, agents that inhibit hyperplasia and in particular restenosis, smooth muscle cell inhibitors, antibiotics, cytokines, growth factors, growth factor inhibitors, cell adhesion inhibitors, cell adhesion promoters and drugs that may enhance the formation of healthy tissue, including endothelial and epithelial cell regeneration, etc.

Anti-thrombogenic agents, may include, for example, heparin, warfarin, hirudin and its analogs, aspirin, indomethacin, dipyridamole, prostacyclin, prostaglandin E, sulfinpyrazone, abciximab, eptifabatide, phenothiazines (such as chlorpromazine or trifluperazine) RGD (arginine-glycine-aspartic acid) peptide or RGD peptide mimetics, agents that block platelet glycoprotein IIb-IIIa receptors (such as C-7E3), ticlopidine or the thienopyridine known as clopidogrel. Statins, may include, for example, simvastatin, atorvastatin, lovastatin, pravastatin, and fluvastatin. α-adrenergic receptor antagonists may include, for example, prazosin, terazosin, doxazosin, ketanserin, indoramin, urapidil, clonideine, guanabenz, guanfacine, guanadrel, reserpine, and metyrosine. $β_1$-selective adrenergic antagonists may include, for example, metoprolol, atenolol, esmolol, acebutolol, bopindolol, carteolol, oxprenolol, penbutolol, medroxalol, bucindolol, levobunolol, metipranolol, bisoprolol, nebivolol, betaxolol, celiprolol, sotalol, propafenone, propranolol, timolol maleate, and nadolol. ACE inhibitors may include, for example, captopriol, fentiapril, pivalopril, zofenopril, alacepril, enalapril, enalaprilat, enalaprilo, lisinopril, benazepril, quinapril, moexipril. Calcium channel blockers may include, for example, nisoldipine, verapamil, diltiazem, nifedipine, nimodipine, felodipine, nicardipine, isradipine, amlodipine, and bepridil. Angiotensin II receptor antagonists may include, for example, losartan, candesartan, irbesartan, valsartan, telmisartan, eprosartan, and olmesartan medoxomil. Vasodilators may include, for example, hydralazine, minoxidil, sodium nitroprusside, diazoxide, bosentan, eporprostenol, treprostinil, and iloprost. Anti-inflammatory agents may include, for example, steroids (including, for example, cortisol, cortisone, fludrocortisone, prednisone, prednisolone, 6-α-methylprednisolone, triamcinolone, betamethasone, corticosterone, budesonide, estrogen, sulfasalazine, mesalamine and dexamethasone), non-steroidal agents (including, for example, salicylic acid derivatives i.e. aspirin; para-aminophenol derivatives e.g. acetaminophen; indole and indene acetic acids, e.g. indomethacin, sulindac, and etodalac; heteroaryl acetic acids e.g. tolmetin, diclofenac, and ketorolac; arylpropionic acids e.g. ibuprofen and derivatives; anthranilic acids e.g. mefenamic acid, and meclofenamic acid; enolic acids e.g. piroxicam, tenoxicam, phenylbutazone, and oxyphenthatrazone); and nabumetone. Imunnosuppresant agents may include, for example, sirolimus, cyclosporine, tacrolimus, azathioprine, and mycophenolate mofetil. Anti-proliferative/antimitotic agents may also be used as therapeutic agents, including, for example, such as *vinca* alkaloids (e.g. vinblastine, vincristine, and vinorelbine), paclitaxel, epidipodophyllotoxins (e.g. etoposide, teniposide), antibiotics (dactinomycin (actinomycin D), daunorubicin, doxorubicin and idarubicin), anthracyclines, mitoxantrone, bleomycins, plicamycin (mithramycin) and mitomycin. Antiplatelet agents including, for example, acetylsalicylic acid, dipyridamole, clopidogrel, ticlopidine, abciximab, eptifbatide, tirofiban, reversable COX-1 inhibitors, BPIIIb/IIIa blockers, TP antagonists, and P2Y12 antagonists.

Anti-inflammatory agents may include, for example, steroids (including, for example, cortisol, cortisone, fludrocortisone, prednisone, prednisolone, 6-α-methylprednisolone, triamcinolone, betamethasone, corticosterone, budesonide, estrogen, sulfasalazine, mesalarnine and dexamethasone), non-steroidal agents (including, for example, salicylic acid derivatives i.e. aspirin; para-aminophenol derivatives e.g acetaminophen; indole and indene acetic acids, e.g. indomethacin, sulindac, and etodalac; heteroaryl acetic acids e.g. tolmetin, diclofenac, and ketorolac; arylpropionic acids e.g ibuprofen and derivatives; anthranilic acids e.g mefenamic acid, and meclofenamic acid; enolic acids e.g piroxicam, tenoxicam, phenylbutazone, and oxyphenthatrazone); and nabumetone.

Imunnosuppresant agents may include, for example, sirolimus, cyclosporine, tacrolimus, azathioprine, and mycophenolate mofetil.

Appropriate dose levels for such therapeutic agents are known to those in the pharmaceutical arts. Such therapeutic agents may be prepared and formulated for inclusion in the medical devices of the present invention using techniques known to those in the art.

In certain embodiments, one, two three, four, five or six therapeutic agents may be used in combination.

Agents Useful for Wound Healing

As used herein, agents useful for wound healing include stimulators, enhancers or positive mediators of the wound healing cascade which 1) promote or accelerate the natural wound healing process or 2) reduce effects associated with improper or delayed wound healing, which effects include, for example, adverse inflammation, epithelialization, angiogenesis and matrix deposition, and scarring and fibrosis.

Positive mediators, enhancers and stimulators include for example, an agent which may stimulate, enhance, facilitate, or accelerate (i.e., agonize) the quantity, quality or efficacy of wound healing or the active wound healing process, or a wound healing-associated growth factor or cytokine at a wound site, or the activation of a wound healing-associated growth factor or cytokine receptor. Such agents may include a wound healing-associated growth factor or cytokine or a partially modified form of a wound healing-associated growth factor or cytokine, for example. A partially modified form of wound healing-associated growth factor or cytokine may, for example, have a longer half-life than the natural wound healing-associated growth factor or cytokine. Alternatively, it may be an inhibitor of wound healing-associated growth factor or cytokine metabolism.

Partial modification of such an agent may be by way of addition, deletion or substitution of amino acid residues. A substitution may for example be a conserved substitution. Hence a partially modified molecule may be a homologue of the molecule from which it was derived. It may have at least about 40%, for example about 50, 60, 70, 80, 90 or 95%, homology with the molecule from which it is derived.

As used herein, agents useful for wound healing may include for example, wound-healing-promoting or scar-reducing agents for wound treatment modalities now known in the art or later-developed; exemplary factors, agents or modalities including natural or synthetic growth factors, cytokines, or modulators thereof to promote wound healing, wound healing promoting bioengineered matrix, dressings bandages, and the like. Suitable examples may include, but not limited to 1) topical or dressing and related therapies and debriding agents (such as, for example, Santyl® collagenase) and Iodosorb® (cadexomer iodine); 2) antimicrobial agents, including systemic or topical creams or gels, including, for example, silver-containing agents such as SAGs (silver antimicrobial gels), (CollaGUARD™, Innocoll, Inc) (purified type-I collagen protein based dressing), CollaGUARD Ag (a collagen-based bioactive dressing impregnated with silver for infected wounds or wounds at risk of infection), DermaSIL™ (a collagen-synthetic foam composite dressing for deep and heavily exuding wounds); 3) cell therapy or bioengineered skin, skin substitutes, and skin equivalents, including, for example, Dermograft (3-dimensional matrix cultivation of human fibroblasts that secrete cytokines and growth factors), Apligraf® (human keratinocytes and fibroblasts), Graftskin® (bilayer of epidermal cells and fibroblasts that is histologically similar to normal skin and produces growth factors similar to those produced by normal skin), TransCyte (a Human Fibroblast Derived Temporary Skin Substitute) and Oasis® (an active biomaterial that comprises both growth factors and extracellular matrix components such as collagen, proteoglycans, and glycosaminoglycans); 4) cytokines, growth factors or hormones (both natural and synthetic) introduced to the wound to promote wound healing, including, for example, NGF, NT3, BDGF, integrins, plasmin, semaphoring, blood-derived growth factor, keratinocyte growth factor, tissue growth factor, TGF-alpha, TGF-beta, PDGF (one or more of the three subtypes may be used: AA, AB, and B), PDGF-BB, TGF-beta 3, factors that modulate the relative levels of TGFβ3, TGFβ1, and TGFβ2 (e.g., Mannose-6-phosphate), sex steroids, including for example, estrogen, estradiol, or an oestrogen receptor agonist selected from the group consisting of ethinyloestradiol, dienoestrol, mestranol, oestradiol, oestriol, a conjugated oestrogen, piperazine oestrone sulphate, stilboestrol, fosfesterol tetrasodium, polyestradiol phosphate, tibolone, a phytoestrogen, 17-beta-estradiol; thymic hormones such as Thymosin-beta-4, EGF, HB-EGF, fibroblast growth factors (e.g., FGF1, FGF2, FGF7), keratinocyte growth factor, TNF, interleukins family of inflammatory response modulators such as, for example, IL-10, IL-1, IL-2, IL-6, IL-8, and IL-10 and modulators thereof; INFs (INF-alpha, -beta, and -delta); stimulators of activin or inhibin, and inhibitors of interferon gamma prostaglandin E2 (PGE2) and of mediators of the adenosine 3',5'-cyclic monophosphate (cAMP) pathway; adenosine A1 agonist, adenosine A2 agonist or 5) other agents useful for wound healing, including, for example, both natural or synthetic homologues, agonist and antagonist of VEGF, VEGFA, IGF; IGF-1, proinflammatory cytokines, GM-CSF, and leptins and 6) IGF-1 and KGF cDNA, autologous platelet gel, hypochlorous acid (Sterilox®) lipoic acid, nitric oxide synthase3, matrix metalloproteinase 9 (MMP-9), CCT-ETA, alphavbeta6 integrin, growth factor-primed fibroblasts and Decorin, silver containing wound dressings, Xenaderm™, papain wound debriding agents, lactoferrin, substance P, collagen, and silver-ORC, placental alkaline phosphatase or placental growth factor, modulators of hedgehog signaling, modulators of cholesterol synthesis pathway, and APC (Activated Protein C), keratinocyte growth factor, TNF, Thromboxane A2, NGF, BMP bone morphogenetic protein, CTGF (connective tissue growth factor), wound healing chemokines, decorin, modulators of lactate induced neovascularization, cod liver oil, placental alkaline phosphatase or placental growth factor, and thymosin beta 4. In certain embodiments, one, two three, four, five or six agents useful for wound healing may be used in combination.

It is to be understood that the agents useful for wound healing (including for example, growth factors and cytokines) above encompass all naturally occurring polymorphs (for example, polymorphs of the growth factors or cytokines). Also, functional fragments, chimeric proteins comprising one of said agents useful for wound healing or a functional fragment thereof, homologues obtained by analogous substitution of one or more amino acids of the wound healing agent, and species homologues are encompassed. It is contemplated that one or more agents useful for wound healing may be a product of recombinant DNA technology, and one or more agents useful for wound healing may be a product of transgenic technology. For example, platelet derived growth factor may be provided in the form of a recombinant PDGF or a gene therapy vector comprising a coding sequence for PDGF.

A fragment or partially modified form thereof refers to a fragment or partially modified form of the wound healing agent which retains the biological or wound healing functionality of the factor, although it may of course have additional functionality. Partial modification may, for example, be by way of addition, deletion or substitution of amino acid residues. For example, a substitution may be a conserved substitution. Hence the partially modified molecules may be homologues of the wound healing agent. They may, for example, have at least about 40% homology with said factor. They may for example have at least about 50, 60, 70, 80, 90 or 95% homology with said factor. For example, in certain embodiments, IL-10 or a fragment or a partially modified form thereof may be administered at a concentration of between about 1 μM and about 10 μM. It may be administered at a concentration of between about 2.5 μM and about 5 μM. In certain other embodiments, IL-10 or a fragment or a partially modified form thereof may be administered immediately prior to wound healing, but may be effective if administered within about 7 days of wounding. It could be administered on at least two occasions.

Gap Junction Modifying Agents

Gap junction modifying agents, include agents that close or block gap junctions or otherwise prevent or decrease cell to cell communication via gap junctions.

As used herein, "gap junction modifying agent" may broadly include those agents or compounds that prevent, decrease or modulate, in whole or in part, the activity, function, or formation of a hemichannel or a gap junction.

In other embodiments, a gap junction modifying agent prevents or decreases, in whole or in part, the formation or activity of a hemichannel or a gap junction.

In certain embodiments, a gap junction modifying agent induces closure, in whole or in part, of a hemichannel or a gap junction. In other embodiments, a gap junction modifying agent blocks, in whole or in part, a hemichannel or a gap junction. In certain embodiments, a gap junction modifying agent decreases or prevents, in whole or in part, the opening of a hemichannel or gap junction.

In certain embodiments, said blocking or closure of a gap junction or hemichannel by a gap junction modifying agent can reduce or inhibit extracellular hemichannel communication by preventing or decreasing the flow of small molecules through an open channel to and from an extracellular or periplamic space.

Gap junction modifying agents used for closing gap junctions (e.g. phosphorylating connexin 43 tyrosine residue) have been reported in U.S. Pat. No. 7,153,822 to Jensen et al., U.S. Pat. No. 7,250,397, and assorted patent publications. Exemplary gap junction modifying agents, also include peptides and peptidomimetics are reported in Green et al., WO2006134494. See also Gourdie et al., see WO2006069181, and Tudor et al., see WO2003032964.

As used herein, "gap junction phosphorylating agent" may include those agents or compounds capable of inducing phosphorylation on connexin amino acid residues in order to induce gap junction or hemichannel closure. Exemplary sites of phosphorylation include one or more of a tyrosine, serine or threonine residues on the connexin protein. In certain embodiments, modulation of phosphorylation may occur on one or more residues on one or more connexin proteins. Exemplary gap junction phosphorylating agents are well known in the art and may include, for example, c-Src tyrosine kinase or other G protein-coupled receptor agonists. See Giepmans B, J. Biol. Chem., Vol. 276, Issue 11, 8544-8549, Mar. 16, 2001. In one embodiment, modulation of phosphorylation on one or more of these residues impacts hemichannel function, particularly by closing the hemichannel. In another embodiment, modulation of phosphorylation on one or more of these residues impacts gap junction function, particularly by closing the gap junction. Gap junction phosphorylating agents that target the closure of connexin 43 gap junctions and hemichannels are preferred. Still other anti-connexin agents include connexin carboxy-terminal polypeptides. See Gourdie et al., WO2006/069181.

In certain another aspect, gap junction modifying agent may include, for example, aliphatic alcohols; octanol; heptanol; anesthetics (e.g. halothane), ethrane, fluothane, propofol and thiopental; anandamide; arylaminobenzoate (FFA: flufenamic acid and similar derivatives that are lipophilic); carbenoxolone; Chalcone: (2',5'-dihydroxychalcone); CHFs (Chlorohydroxyfuranones); CMCF (3-chloro-4-(chloromethyl)-5-hydroxy-2(5H)-furanone); dexamethasone; doxorubicin (and other anthraquinone derivatives); eicosanoid thromboxane A(2) (TXA(2)) mimetics; NO (nitric oxide); Fatty acids (e.g. arachidonic acid, oleic acid and lipoxygenase metabolites; Fenamates (flufenamic (FFA), niflumic (NFA) and meclofenamic acids (MFA)); Genistein; glycyrrhetinic acid (GA):18a-glycyrrhetinic acid and 18-beta-glycyrrhetinic acid, and derivatives thereof; lindane; lysophosphatidic acid; mefloquine; menadione; 2-Methyl-1,4-naphthoquinone, vitamin K(3); nafenopin; okadaic acid; oleamide; oleic acid; PH, gating by intracellular acidification; e.g. acidifying agents; polyunsaturated fatty acids; fatty acid GJIC inhibitors (e.g. oleic and arachidonic acids); quinidine; quinine; all trans-retinoic acid; and tamoxifen.

Medical Devices

The term "medical device" refers to an instrument, apparatus, implement, machine, contrivance, implant, or other similar or related article, including a component part or accessory which is intended for use in the diagnosis of disease or other conditions or in the cure, mitigation, treatment or prevention of a disease, disorder or condition in humans or in other animals (particularly in mammals); is intended to affect the structure or any function of the body of a human or other animal; or is recognized in the official National Formulary or the United States Pharmacopoeia or any supplement to them. In particular, "medical device" includes a manufactured product which is used to cope with a disease, disorder or condition (particularly human diseases, disorders or conditions), such as by preventing, diagnosing, treating, alleviating and or monitoring disease, disorder or condition; care for injuries (particularly human injuries), such as by diagnosing, treating, alleviating, monitoring or compensating for injuries; meet anatomical needs (particularly human anatomical needs), such as by investigating, replacing, modifying or supporting anatomical structures; maintain physiological functions (particularly human physiological functions), such as by investigating, replacing, modifying or supporting physiological functions; supporting or sustaining life (particularly human life); and controling conception (particularly human conception).

The term "implantable medical device" refers to a medical device that is partly or totally inserted into the subject's body (such as the body of a human or other mammal) or a natural orifice thereof and is expected to stay there for an extended period of time (for example about 2, 5 7, 10, 14, or 30 days or more). Typically, surgical or medical procedures are used to insert or apply implantable medical devices, and surgical or medical procedures are used to remove them.

The anti-connexin agents, compositions, and methods provided herein can be used in a variety of procedures that utilize of implants, medical and surgical devices, and the like. In one aspect, implants, surgical devices or stents, are coated with or otherwise constructed to contain and/or release any of the anti-connexin agents provided herein. Medical devices comprising an anti-connexin agent, may include, for example, stents, balloons, prosthetic heart valves, annuloplasty rings, ventricular assist devices, including left ventricular assist devices, right ventricular assist devices, and biventricular assist devices, grafts, shunts, sewing rings (including those having silicone or polyurethane inserts), polyester fabric encasements, medical leads, orthopedic plates, bone pins, bone substitutes, anchors, joints, screws, ophthalmic implants (including, for example, orbital implants, lens implants, corneal implants (including intrasomal corneal ring segments (INTACS)), and microchips), catheters, cannulae, pulse generators, cardiac defibrillators, arteriovenous shunts, pacemakers, sutures, suture anchors, staples, anastomosis devices, vertebral disks, hemostatic barriers, clamps, clips, vascular implants, tissue adhesives and sealants, tissue scaffolds, intraluminal devices, vascular supports as well as any devices used in connection with general orthopedic, hip replacement, CNS, ocular, gastrointestinal, and endoscopy procedures.

Other examples include cardiovascular devices (e.g., implantable venous catheters, venous ports, tunneled venous catheters, chronic infusion lines or ports, including hepatic artery infusion catheters, pacemaker wires, implantable defibrillators); neurologic/neurosurgical devices (e.g., ventricular peritoneal shunts, ventricular atrial shunts, nerve stimulator devices, dural patches and implants to prevent epidural fibrosis post-laminectomy, devices for continuous subarachnoid infusions); gastrointestinal devices (e.g., chronic indwelling catheters, feeding tubes, and shunts), splints for failed dacrocystalrhinostomy, implants for diabetic retinopathy; otolaryngology devices (e.g., ossicular implants, Eustachian tube splints or stents for glue ear or chronic otitis as an alternative to transtempanic drains); plastic surgery implants (e.g., prevention of fibrous contracture in response to gel- or saline-containing breast implants in the subpectoral or subglandular approaches or post-mastectomy, or chin implants), and orthopedic implants (e.g., cemented orthopedic prostheses).

Examples of stents include intravascular and intraductal stents, and see also, for example, Pepine et al., "Coronary Artery Stents, *JACC* Vol. 28, No. 3, September 1996:782-94; D. Stoeckel, "A survey of stent designs," *Min Invas Ther & Allied Technol* 2002: 11(4) 137-147. Stents may also include, for example, balloon-expandable stents and self-expanding stents. Balloon-expandable stents include those of the sort available from a number of commercial suppliers, including Cordis Johnson & Johnson Interventional Systems, Medi-Tech, Cook, ACS, and Metronic. Self-expanding stents are typically composed, for example, from a shape memory alloy and are available from suppliers, such as Instent. In the case of stents, a balloon-expandable stent is typically composed of a stainless steel framework or, in the case of self-expanding stents, from nickel/titanium alloy. While typically stents are made of a metallic material for strength purposes, polymeric or plastic materials may also be utilized in the stent construction. While it is preferred that the stent be coated in an expanded position, coating the stent in an unexpanded position is also contemplated. Exemplary coated balloons include, for example, coated balloons and coated balloon catheters, including inflatable and self inflatable coated balloons and balloon catheters. The inflatable coated balloon may be a non-dispensable balloon, for example, typically composed of polyethyleneterephthalate, or it may be an elastic balloon, for example, typically being composed of latex or silicone rubber.

Preparation of Devices

Implants and other surgical and medical devices may be coated with (or otherwise adapted to release) agents of the invention (e.g., anti-connexin agents and compositions) in a variety of manners, including for example: (a) by directly affixing to the implant or device an anti-connexin agent or composition (e.g., by either spraying the implant or device with a polymer/drug film, or by dipping the implant or device into a polymer/drug solution, or by other covalent or noncovalent means); (b) by coating the implant or device with a substance such as a hydrogel which will in turn absorb the anti-connexin composition (or anti-connexin factor above); (c) by interweaving anti-connexin composition coated thread (or the polymer itself formed into a thread) into the implant or device; (d) by inserting the implant or device into a sleeve or mesh which is comprised of or coated with an anti-connexin composition; (e) constructing the implant or device itself with an anti-connexin agent or composition; or (f) by otherwise adapting the implant or device to release the anti-connexin agent, for example by providing multiple layers or other delivery vehicles, layers or other delivery vehicles with differing release characteristics, or by preparing a device with different parts or regions that include (by layers or otherwise) different compounds (with or without different release characteristics). Within preferred embodiments of the invention, the composition should firmly adhere to the implant or device during storage and at the time of insertion. The anti-connexin agent or composition should also preferably not degrade during storage, prior to insertion, or when warmed to body temperature after insertion inside the body (if this is required). In addition, it should preferably coat the implant or device smoothly and evenly, with a uniform distribution of anti-connexin agent, while not changing the stent contour. Within preferred embodiments of the invention, the anti-connexin agent or composition should provide a uniform, predictable, prolonged release of the anti-connexin factor into the tissue surrounding the implant or device once it has been deployed. For vascular stents, in addition to the above properties, the composition should not render the stent thrombogenic (causing blood clots to form), or cause significant turbulence in blood flow (more than the stent itself would be expected to cause if it was uncoated).

Delivery of anti-connexin agents utilizing a stent can be carried out in a number of ways, including, for example, from the struts of a stent, a stent graft, the catheter used to deliver the stent, the stent cover or sheath. Various methods of applying a therapeutic agent to a stent and administering the therapeutic agent via the stent are disclosed in U.S. Pat. Nos. 6,702,850; 6,585,764; 6,358,556; 6,344,028; 6,251,136; 5,697,967; 5,599,352; 5,591,227; 5,464,650; 5,304,121; 5,163,952; 5,092,877; 4,994,071; and 4,916,193, the disclosures of which are incorporated in their entirety herein by reference. Other devices may be coated or impregnated using these or other techniques in the art, including those now known or later developed.

Any one or more of the foregoing medical devices can include an overlayer of any type, including, for example, a fabric such as a sheath, an encasement, a layer, or a coating, such that the fabric overlayer is in contact with body tissue or fluids such as blood. Alternatively, instead of a fabric overlayer, the medical device may include any other type of layer such as, for example, a mesh, coil, wire, inflatable balloon, bead, sheet, or any other structure which is capable of being used or implanted at a target location, including, for example, intravascular target locations, intra-joint locations, intraluminal target locations, intra-orbital and intra-ocular target locations, target locations within solid tissue, joints, heart, intestine, eyes, etc.

Impregnated Dressings and Matrices

In one aspect, medical devices are provided in the form of a dressing or matrix comprising one or more anti-connexin agents, one or more therapeutic agents, agents useful for wound healing and/or gap junction modifying agents. In certain embodiments, the one or more agents of the invention are provided in the form of a liquid, semi solid or solid composition for application directly, or the composition is applied to the surface of, or incorporated into, a solid contacting layer such as a dressing gauze or matrix. The dressing composition may be provided for example, in the form of a fluid or a gel. The one or more anti-connexin agents and one or more therapeutic agents, agents useful for wound healing and/or gap junction modifying agents may be provided in combination with conventional pharmaceutical excipients for topical application. Suitable carriers include: Pluronic gels, Polaxamer gels, Hydrogels containing cellulose derivatives, including hydroxyethyl cellulose, hydroxymethyl cellulose, carboxymethyl cellulose, hydroxypropylmethyl cellulose and mixtures thereof; and hydrogels containing polyacrylic acid (Carbopols). Suitable carriers also include creams/ointments used for topical pharmaceutical preparations, e.g., creams based on cetomacrogol emulsifying ointment. The above carriers may include alginate (as a thickener or stimulant), preservatives such as benzyl alcohol, buffers to control pH such as disodium hydrogen phosphate/sodium dihydrogen phosphate, agents to adjust osmolarity such as sodium chloride, and stabilizers such as EDTA.

Suitable dressings or matrices may include, for example, the following with one or more anti-connexin agents with one or more therapeutic agents, agents useful for wound healing and/or gap junction modifying agents:

1) Absorptives: suitable absorptives may include, for example, absorptive dressings, which can provide, for example, a semi-adherent quality or a non-adherent layer, combined with highly absorptive layers of fibers, such as for example, cellulose, cotton or rayon. Alternatively, absorptives may be used as a primary or secondary dressing.

2) Alginates: suitable alginates include, for example, dressings that are non-woven, non-adhesive pads and ribbons composed of natural polysaccharide fibers or xerogel derived from seaweed. Suitable alginates dressings may, for example, form a moist gel through a process of ion exchange upon contact with exudate. In certain embodiments, alginate dressings are designed to be soft and conformable, easy to pack, tuck or apply over irregular-shaped areas. In certain embodiments, alginate dressings may be used with a second dressing.

3) Antimicrobial Dressings: suitable antimicrobial dressings may include, for example, dressings that can facilitate delivery of bioactive agents, such as, for example, silver and polyhexamethylene biguanide (PHMB), to maintain efficacy against infection, where this is needed or desirable. In certain embodiments, suitable antimicrobial dressings may be available as for example, as sponges, impregnated woven gauzes, film dressings, absorptive products, island dressings, nylon fabric, non-adherent barriers, or a combination of materials.

4) Biological & Biosynthetics: suitable biological dressings or biosynthetic dressings may include, for example, gels, solutions or semi-permeable sheets derived from a natural source. In certain embodiments, a gel or solution is applied to the treatment site and covered with a dressing for barrier protection. In another embodiment, a sheet is placed in situ which may act as membrane, remaining in place after a single application.

5) Collagens: suitable collagen dressings may include, for example, gels, pads, particles, pastes, powders, sheets or solutions derived from for example, bovine, porcine or avian sources or other natural sources or donors. In certain embodiments, the collagen dressing may interact with treatment site exudate to form a gel. In certain embodiments, collagen dressing may be used in combination with a secondary dressing.

6) Composites: suitable composite dressings may include, for example, dressings that combine physically distinct components into a single product to provide multiple functions, such as, for example, a bacterial barrier, absorption and adhesion. In certain embodiment, the composite dressings are comprised of, for example, multiple layers and incorporate a semi- or non-adherent pad. In certain embodiment, the composite may also include for example, an adhesive border of non-woven fabric tape or transparent film. In certain other embodiment, the composite dressing may function as for example, either a primary or a secondary dressing and in yet another embodiment, the dressing may be used in combination with topical pharmaceutical composition.

7) Contact Layers: suitable contact layer dressings may include, for example, thin, non-adherent sheets placed on an area to protect tissue from for example, direct contact with other agents or dressings applied to the treatment site. In certain embodiments, contact layers may be deployed to conform to the shape of the area of the treatment site and are porous to allow exudate to pass through for absorption by an overlying, secondary dressing. In yet another embodiment, the contact layer dressing may be used in combination with topical pharmaceutical composition. In another embodiment, internal dressing, contact sheets or films may be used to reduce or prevent abnormal wound healing in the muscle, connective, epithelial and nerve tissue.

8) Elastic Bandages: suitable elastic bandages may include, for example, dressings that stretch and conform to the body contours. In certain embodiment, the fabric composition may include for example, cotton, polyester, rayon or nylon. In certain other embodiments, the elastic bandage may for example, provide absorption as a second layer or dressing, to hold a cover in place, to apply pressure or to cushion a treatment site.

9) Foams: suitable foam dressings may include, for example, sheets and other shapes of foamed polymer solutions (including polyurethane) with small, open cells capable of holding fluids. Exemplary foams may be for example, impregnated or layered in combination with other materials. In certain embodiment, the absorption capability may be adjusted based on the thickness and composition of the foam. In certain other embodiments, the area in contact with the treatment site may be non-adhesive for easy removal. In yet another embodiment, the foam may be used in combination with an adhesive border and/or a transparent film coating that can serve as an anti-infective barrier.

10) Gauzes & Non-Woven dressings: suitable gauze dressings and woven dressings may include, for example, dry woven or non-woven sponges and wraps with varying degrees of absorbency. Exemplary fabric composition may include, for example, cotton, polyester or rayon. In certain embodiment, gauzes and non-woven dressing may be available sterile or non-sterile in bulk and with or without an adhesive border. Exemplary gauze dressings and woven dressings may be used for cleansing, packing and covering a variety of treatment sites.

11) Hydrocolloids: suitable hydrocolloid dressings may include, for example, wafers, powders or pastes composed of gelatin, pectin or carboxymethylcellulose. In certain embodiment, wafers are self-adhering and available with or without an adhesive border and in a wide variety of shapes and sizes. Exemplary hydrocolloids are useful on areas that require contouring. In certain embodiments, powders and pastes hydrocolloids may use used in combination with a secondary dressing.

12) Hydrogels (Amorphous): suitable amorphous hydrogel dressings may include, for example, formulations of water, polymers and other ingredients with no shape, designed to donate moisture and to maintain a moist healing environments and or to rehydrate the treatment site. In certain embodiment, hydrogels may be used in combination with a secondary dressing cover.

13) Hydrogels: Impregnated Dressings: suitable impregnated hydrogel dressings may include, for example, gauzes and non-woven sponges, ropes and strips saturated with an amorphous hydrogel. Amorphous hydrogels may include for example, formulations of water, polymers and other ingredients with no shape, designed to donate moisture to a dry treatment site and to maintain a moist healing environment.

14) Hydrogel Sheets: suitable hydrogel sheets may include for example, three-dimensional networks of cross-linked hydrophilic polymers that are insoluble in water and interact with aqueous solutions by swelling. Exemplary hydrogels are highly conformable and permeable and can absorb varying amounts of drainage, depending on their composition. In certain embodiment, the hydrogel is non-adhesive against the treatment site or treated for easy removal.

15) Impregnated Dressings: suitable impregnated dressings may include, for example, gauzes and non-woven sponges, ropes and strips saturated with a solution, an emulsion, oil, gel or some other pharmaceutically active compound or carrier agent, including for example, saline, oil, zinc salts, petrolatum, xeroform and scarlet red as well as the compounds described herein.

16) Silicone Gel Sheets: suitable silicone gel sheet dressings may include, for example, soft covers composed of cross-linked polymers reinforced with or bonded to mesh or fabric.

17) Solutions: suitable liquid dressings may include, for example, mixtures of multiprotein material and other elements found in the extracellular matrix. In certain embodiment, exemplary solutions may be applied to the treatment site after debridement and cleansing and then covered with an absorbent dressing or a nonadherent pad.

18) Transparent Films: suitable transparent film dressings may include polymer membranes of varying thickness coated on one side with an adhesive. In certain embodiments, transparent films are impermeable to liquid, water and bacteria but permeable to moisture vapor and atmospheric gases. In certain embodiments, the transparency allows visualization of the treatment site.

19) Fillers: suitable filler dressings may include, for example, beads, creams, foams, gels, ointments, pads, pastes, pillows, powders, strands or other formulations. In certain embodiment, fillers are non-adherent and may include a time-released antimicrobial. Exemplary fillers may be useful to maintain a moist environment, manage exudate, and for treatment of for example, partial- and full-thickness wounds, infected wounds, draining wounds and deep wounds that require packing.

Tissue can be damaged, and inflammation can occur, during the use of medical devices during medical procedures, and from the implantation of medical devices.

Mammals that may be treated using the described and claimed devices and methods include, for example, a human being having, or at risk for developing, for example, tissue damage and/or organ dysfunction, for example cardiovascular, ocular, gastrointestinal, CNS or internal organ tissue damage and/or dysfunction, and/or inflammation.

In one aspect of the invention, the medical device comprising an anti-connexin agent, e.g., an anti-connexin 43 agent, is a ventricular assist device. In another aspect of the invention, the medical device comprising an anti-connexin agent, e.g., an anti-connexin 43 agent, is a left ventricular assist device. In yet another aspect of the invention, the medical device comprising an anti-connexin agent, e.g., an anti-connexin 43 agent, is a right ventricular assist device.

In one aspect of the invention, the medical device comprising an anti-connexin agent, e.g., an anti-connexin 43 agent, comprises a stent. In another aspect, the stent comprising an anti-connexin agent, e.g., an anti-connexin 43 agent, is a drug-eluting stent.

In one aspect of the invention, the medical device comprising an anti-connexin agent, e.g., an anti-connexin 43 agent, comprises a suture. In another aspect, the suture comprising an anti-connexin agent, e.g., an anti-connexin 43 agent, is a coated or impregnated drug-eluting suture.

In another aspect of the invention, a medical device comprises an instrument, such as a catheter, for example, or an implant suitable for introduction into a subject of which at least a portion comprises an anti-connexin agent, e.g., an anti-connexin 43 agent, that is available to ameliorate gap junction formation and/or hemichannel opening in the subject when the device is used.

In one embodiment, the release rate of the anti-connexin agent is controlled. In one embodiment of the invention, the anti-connexin agent may be released slowly or over a sustained period. In one embodiment the anti-connexin agent is released, for example, over the period of the resorption or degradation of the body of the medical device, or a portion thereof.

In one embodiment of the invention, the surface of the medical device comprises an anti-connexin agent, e.g., an anti-connexin 43 agent. In one aspect of the invention an anti-connexin agent is bound, either directly or indirectly, to a medical device. In another aspect of the invention, an anti-connexin agent is bound, directly or indirectly, to a surface of a medical device. In another aspect of the invention, this surface contacts a tissue within a subject. In one embodiment, the target tissue is heart tissue, vascular tissue, muscle tissue, or connective tissue. In yet another embodiment, this surface contacts a site of injury or potential injury. In another embodiment, the medical device provides for surface contact release of the anti-connexin agent, e.g., an anti-connexin 43 agent.

In one embodiment, an anti-connexin agent, e.g., an anti-connexin 43 agent, is present in a coating on a surface of the medical device. Such coatings include, for example, synthetic or natural matrices, for example, fibrin or acetate-based polymers, mixtures of polymers or copolymers, which can also be bioresorbable or biodegradable matrices, and which matrices have or include or incorporate an anti-connexin agent. Such matrices can, for example, provide for surface contact or metered or sustained release of one or more anti-connexin agent.

In another embodiment, the device comprising an anti-connexin agent, e.g., an anti-connexin 43 agent, may be formed, at least in part, for example, from a biodegradable or bioresorbable polymer material. Polymer materials can include, for example, but are not limited to, nylon, polyethylene perthalate, polytetrafluoroethylene, etc. Other polymers may also include, for example, hexafluoropropylene (HFP), tetrafluoroethylene (TFE), vinylidenefluoride, 1-hydropentafluoropropylene, perfluoro(methyl vinyl ether), chlorotrifluoroethylene (CTFE), pentafluoropropene, trifluoroethylene, hexafluoroacetone and hexafluoroisobutylene.

In another aspect, the surface of a medical device comprising an anti-connexin agent, e.g., an anti-connexin 43 agent, may be composed of organic materials or a composite of organic and inorganic materials. Examples of such materials include, but are not limited to, for example, synthetic polymers or copolymers containing one or more anti-connexin agents, surfaces upon which a functionalized monolayer containing the anti-connexin agent is adsorbed or otherwise attached, or synthetic polymeric materials or proteins blended with one or more anti-connexin agents.

In another aspect, all or a portion of the medical device is coated with an anti-connexin agent, e.g., an anti-connexin 43 agent, either as the coating per se or in a coating matrix, for example; or all or a portion of the medical device may be produced from a material which includes an anti-connexin agent, for example, a polymer which has admixed therewith an anti-connexin agent or which includes a functionalized anti-connexin agent; or all or a portion of the tissue-contacting surfaces of the medical device may be derivatized with an anti-connexin agent.

The medical device can be coated using any one or more methods known in the art, for example, dip coating, spray coating, sponging or brushing. The coating may contain the anti-connexin agent, e.g., an anti-connexin 43 agent, in a weight percentage range of from about 0.0001% to about 30%, for example, although other amounts are contemplated and may be used. Thus, according to one option, the coating may contain anti-connexin agent in a weight percentage range of about 0.001% to about 25%, alternatively in a range of about 0.01% to about 20%, about 0.1% to about 15%, about 0.5% to about 12%, about 1% to about 10%, about 2% to about 10%, about 5% to about 10%, about 0.01% to about 5%, about 0.1% to about 5% or about 0.5% to about 5%. The weight percentage for the anti-connexin agent will be adjusted as appropriate, in view of considerations which include, but are not limited to, the following: the dose of anti-connexin agent to be delivered locally, the rate of release of anti-connexin agent from the coating and the time period for delivery of anti-connexin agent. Included within the coating may be further suitable excipients, for example, a polymer and/or those excipients that aid in the binding of the coating to the anti-connexin agent (or visa versa) and/or that aid in the release of the anti-connexin agent. Alternatively, excipients can be bound to the anti-connexin agent, for example, a polymer or other substance that entraps the anti-connexin agent on or within the surface of the medical device.

The medical device can also be coated using any one or more methods known in the art, to deliver amounts of an anti-connexin agent ranging from about 0.1 micrograms to about 1 milligram or more, in amounts ranging from about 1 micrograms to about 750 micrograms, in amounts ranging from about 5 micrograms to about 600 micrograms, in amounts ranging from about 10 micrograms to about 500 micrograms, in amounts ranging from about 20 micrograms to about 400 micrograms, in amounts ranging from about 30 micrograms to about 300 micrograms, in amounts ranging from about 50 micrograms to about 200 micrograms, and in amounts ranging from about 50 micrograms to about 100 micrograms, for example, although other amounts are contemplated and may be used, including ranges that include only the lower amounts (or the upper amounts) from the above ranges, for example, amounts ranging from about 1-10 micrograms, about 1-5 micrograms, about 10-50 micrograms, and so on (and amounts ranging from about 100-200 micrograms, about 500-600 micrograms, about 300-400 micrograms, and so on). The amounts of the anti-connexin agent will be adjusted as appropriate, in view of considerations that include, but are not limited to, the following: the dose of anti-connexin agent to be delivered locally, the rate of release of anti-connexin agent from the coating and the time period for delivery of anti-connexin agent, the size and nature of the injury, the extent of anticipated tissue damage, inflammation, and so on.

In certain embodiments, methods or coating and dosing/dosage information for the exemplary compounds useful in accordance with the present disclosure may be found in U.S. Pat. No. 7,153,822 to Jensen et al., U.S. Pat. No. 7,250,397, Green et al., WO2006134494; Gourdie et al., see WO2006069181, and Tudor et al., see WO2003032964.

In another aspect, all or a portion or portions of the medical device may be coated with the anti-connexin agent per se or with a pharmaceutically acceptable carrier or excipient comprising the anti-connexin agent which serves as a coat or coating matrix. This may be a solid, liquid, gel or semisolid consistency, for example.

The carrier or matrix can be made of or include agents which provide, for example, for metered or slow or sustained release of the anti-connexin agent and/or other therapeutic agent(s). The coating, for example, can include albumin that can be either, for example, human or bovine, including humanized bovine serum albumin.

A coating may be applied as a single coating or in multiple coatings or layers. The multiple coatings or layers can include varying ratios of anti-connexin agent-to-carrier to vary the release rate of the drug over time. The multiple coatings or layers can also include different medicaments in accordance with a desired treatment plan. In one embodiment, the coating comprises a plurality of coatings or layers of a polymer/anti-connexin agent mixture, e.g., an anti-connexin 43 agent mixture, applied to the medical device. In another embodiment, the anti-connexin agent-to-polymer ratio in the plurality of coatings or layers varies.

In another aspect, anti-connexin agents, e.g., an anti-connexin 43 agents, may be impregnated or otherwise incorporated into the body of all or a portion of the medical device.

Additionally, the anti-connexin agent, e.g., an anti-connexin 43 agent, may be provided in one or more reservoirs or channels formed in the medical device, optionally with a coating or membrane of biocompatible material applied over the medical device to control diffusion of the drug from the reservoirs/channels to the tissue. In one embodiment, the medical device comprises at least one channel formed in an outer surface thereof, and wherein the anti-connexin agent is included on and/or within at least one channel.

In another aspect, if a "burst effect" is desired, the anti-connexin agent, e.g., an anti-connexin 43 agent, may be applied at the outer layer of the medical device (and/or within the device, as well) so that an initial amount of the anti-connexin agent is promptly released when it comes into contact with tissue. Remaining amounts, if any, of anti-connexin agent included in the inner layers will be released over time as the anti-connexin agent diffuses through the material. The anti-connexin agent may be provided either in liquid or solid form.

In another aspect, the coating applied to the medical device can be "recharged", for example, by way of a catheter or other tubing capable of infusing an anti-connexin agent donor to a previously coated surface or impregnated or other device comprising an anti-connexin agent. For example, in one embodiment, the anti-connexin agent may be functionalized to form an anti-connexin agent-protein that will lose potency in vivo as the functionalized-anti-connexin agent-protein is metabolized, leaving un-derivatized protein. The surface coating can be "recharged" by infusing an anti-connexin agent or anti-connexin agent donor capable of binding the un-derivatized protein.

In another aspect of the invention, the derivatization of an artificial surface with an anti-connexin agent provides for the amelioration of tissue damage, and/or enhancement of tissue repair, as well as the prevention and/or amelioration of inflammation. The artificial surfaces may be composed of organic materials or a composite of organic and inorganic materials. Examples of such materials include synthetic polymers or copolymers containing one or more anti-connexin agents, surfaces upon which a functionalized monolayer containing the anti-connexin agent is absorbed, or synthetic polymeric materials or proteins which are blended with the anti-connexin agent.

In one embodiment of the invention, the localized and/or time-related presence of an anti-connexin agent, e.g., an anti-connexin 43 agent, administered in a physiologically effective form is efficacious in diminishing, deterring or preventing tissue damage, including inflammation, after or as a result of instrumental intervention, such as angioplasty, catheterization, or the introduction of a stent (e.g., a Palmaz-Schatz stent), shunt, mesh, joint replacement, or other surgical or indwelling medical device. Local administration of a stable anti-connexin agent inhibits neutrophil and/or macrophage migration following vascular arterial balloon injury, for example, as well as inflammation, swelling and hypeplasia. This strategy for the local delivery of an anti-connexin agent is useful, among other things, for the treatment of vascular injury following angioplasty, and other treatments that can result in vessel or tissue disturbance.

In a further embodiment, the invention provides for the localized use of a functionalized anti-connexin agent-polypeptide or polynucleotide, particularly those which do not elicit any significant or otherwise undesired immune response. Such functionalized anti-connexin agent-polypeptides or polynucleotides, such as, for example, functionalized anti-connexin agent-albumins, can be present as polymeric chains or three dimensional aggregates where the functionalized anti-connexin agent-polypeptide or polynucleotide is the monomeric unit. The polypeptide or polynucleotide of the monomeric unit can also be used to aid, for example, in localization. The aggregates may be multiple inter-adherent monomeric units which can optionally be linked by disulfide bridges or —O— linkages, for example. Additionally, devices which have been substituted or coated with one or more functionalized anti-connexin agent polypeptides or polynucleotides may be dried and stored.

In another aspect, the invention relates to a method of preventing and/or treating damage, including inflammation, associated with the use or implantation of a medical device in a subject comprising introducing into said subject a medical device of which at least a portion comprises an anti-connexin agent, wherein said damage and/or inflammation is prevented, reduce, ameliorated and/or delayed.

In another aspect, the invention related to a method of preventing and/or treating damage and/or inflammation associated with the use or implantation of a medical device in a subject comprising use or implantation of a medical device which comprises an anti-connexin agent that is releasable at its point of contact, wherein the damage and/or inflammation is prevented, amerliorated and/or delayed.

In yet another aspect, the invention relates to a method of preventing and/or treating adverse effects associated with the use or insertion of a medical device in a subject, wherein an anti-connexin agent is locally administered at the site of contact of said medical device, before, during and/or after said use or insertion, wherein said adverse effects are prevented, ameliorated, reduced or delayed. Such adverse effects include inflammation, swelling, hyperplasia, neutrophil migration, and macrophage migration, as well as blood vessel disturbance and/or leakage.

In another aspect, the invention relates to a method of treating a damaged vessel in a subject in need thereof which comprises introducing into said vessel at the site of damage a catheter, a balloon, a graft, a mesh, a stent or a shunt comprising an anti-connexin agent, e.g., an anti-connexin 43 agent.

In another aspect, the invention comprises a method of ameliorating tissue damage and/or enhancing tissue repair by locally administering one or more anti-connexin agents, e.g., an anti-connexin 43 agent, to the site of tissue in need thereof. Such tissue may be damaged, or have been damaged, for example, as a result of the use of a medical device in an invasive procedure. Thus, for example, in treating blocked vasculature, by, for example, angioplasty, damage to the blood vessel can result. Additionally, tissue damage can result when medical devices are left within a subject for an extended period of time. Such damage may be treated by use of an anti-connexin agent. In addition to ameliorating tissue damage and/or enhancing repair of the damaged tissue, such treatment can also be used to prevent and/or alleviate and/or delay occlusions, including for example, acute occlusion and reocclusions. Treatment may also be used to prevent and/or ameliorate and/or delay thrombosis and restenosis. Treatment may also be used to prevent and/or ameliorate and/or delay inflammation. Treatment may also be used to prevent and/or ameliorate and/or delay hyperplasia. Treatment may also be used to prevent and/or ameliorate and/or delay oxidative damage, including, for example oxidative damage by free radicals, including superoxide damage. In other aspect, the invention, treatment may also be used to treat and/or prevent and/or alleviate and/or delay atherosclerotic lesions, and undesired cell proliferation and migration.

In one embodiment the invention comprises a method of ameliorating tissue damage and/or enhancing tissue repair wherein the subject is a mammal. In another embodiment the invention comprises a method of ameliorating tissue damage and/or enhancing tissue repair wherein the subject is human. In another embodiment the invention comprises a method of ameliorating tissue damage and/or enhancing tissue repair wherein the subject is selected from the group consisting of domestic and pet animals (for example, horses, dogs and cats), sports animals (for example, horses and dogs), farm animals, and zoo animals, as well as birds.

In one embodiment the medical device comprising an anti-connexin agent can include one or more other therapeutic agents and/or wound healing agents. In one embodiment, the therapeutic agents may be applied or included directly with the anti-connexin agent, e.g., an anti-connexin 43 agent. In another embodiment, the therapeutic agent may be applied or included in the same coating or coating layer with the anti-connexin agent. In yet another embodiment, the therapeutic agent may be applied or included in separate coating or coating layer or a separate portion of the device.

In one embodiment, the anti-connexin agent is an anti-connexin 43 compound. In another embodiment, the anti-connexin agent downregulates or inhibits connexin 43 mRNA. In another embodiment, the anti-connexin agent suppresses the formation of connexin 43 gap junctions. In another embodiment, the anti-connexin agent suppresses the joining of connexin 43 hemichannels to form gap junctions. In another embodiment, the anti-connexin agent suppresses connexin 43 hemichannel opening.

In another embodiment, the anti-connexin agent targets connexin 31, connexin 31.1, or connexin 43. Preferably, the anti-connexin agent targets connexin 43.

There are various techniques known in the art for the localized delivery of therapeutic agents, for example, but not limited to, by means of a small catheter which extends from the exterior of the subject to the internal tissue site, with a mechanical delivery system being provided to administer a therapeutic agent in a continuous or periodic controlled dosage. This method can be utilized for subjects in need of therapeutic treatment by repeat application. Anti-connexin agents, e.g., an anti-connexin 43 agents, can also be delivered arthoscopically using devices known in the art, which may themselves be coated or impregnated, for example, with an anti-connexin agent, e.g., an anti-connexin 43 agent.

Any catheter, however, is within the scope of the invention, including those for the delivery of therapeutic agents or otherwise. These include, for example, urological catheters (including intermittent catheters, external catheters, and Foley catheters), pancreatic catheters, hepatic catheters, infusion catheters, cardiovascular catheters, renal catheters, hemodynamic monitoring catheters, neurological catheters, and so on. Cannulae, as noted above, are also included.

The method of applying one or more anti-connexin agents, e.g., an anti-connexin 43 agent, to an internal tissue site of a subject comprises, for example, advancing an elongate member, such as a catheter (which may itself be coated or impregnated with one or more anti-connexin agents), internally into the subject to cause a portion of the elongated member to occupy the internal tissue site. A portion of the elongated member comprises a lateral wall section which carries the anti-connexin agent in a manner permitting release thereof from the lateral wall section at the internal tissue site once the site has been reached. This can be determined by the usual methods, such as for example, fiber optic television, x-ray, etc.

The release of the anti-connexin agent at the internal tissue site can occur for example by the use of a catheter balloon, which when inflated causes the anti-connexin agent to be pressed into and/or onto the tissue at the internal tissue site. This allows at least some of the anti-connexin agent to be retained at the tissue site once the catheter balloon is deflated.

The anti-connexin agent can also be mixed with a controlled release carrier and administered in the manner discussed above, for example. Such controlled release carriers can be biodegradable over a period of time, for example, over a period of hours or days, so that as the controlled release carriers are brought into contact with the tissues and/or fluids the controlled release carriers degrade over time to allow for a relatively slow, controlled diffusion of the anti-connexin agent to the tissue and/or fluids. The carrier over time will be removed by natural bodily processes.

The catheter or balloon catheter or other device used to apply a stent to the coronary artery or elsewhere may also be provided with a coating of heparin or other anti-thrombogenic agent, for example, in conjunction with one or more anti-connexin agents, e.g., an anti-connexin 43 agent, that may be combined with a carrier or a controlled release carrier for the anti-connexin agent. Thus, simultaneously with the application of the anti-connexin agent, the heparin or other anti-thrombogenic agent, for example, is applied to the internal tissue site for the long term suppression of thrombogenic activity in the vicinity of the stent in addition to therapeutic effects from the anti-connexin agent.

In addition, while the catheter or other elongate member, for example, is being used to position the stent and is being advanced to the internal tissue site, the portion of the catheter carrying the anti-connexin agent may be enclosed in a protective sheath. The sheath is used to prevent removal of substantial amounts of the anti-connexin agent from the catheter before reaching the desired internal site. When the site is reached, the protective sheath may be withdrawn to expose the catheter portion carrying the anti-connexin agent. The anti-connexin agent, e.g., an anti-connexin 43 agent, can then be applied to the internal site, for example, by expansion of a catheter balloon upon which the anti-connexin agent resides, or by other processes such as spontaneous dispersion off the catheter into the tissues. If desired, the protective sheath may be a conventional introducer catheter, or it may be a split introducer sheath to facilitate removal of the sheath from the catheter after its withdrawal, for example.

One example of a method of coating a medical device having more than one surface or requiring only a portion of a surface of the medical device to be treated is to treat the device with gas plasma that may, for example, be composed of a molecular species containing the anti-connexin agent. In the case of stents, it is particularly desirable to treat the entire surface. In the case of balloons mounted on catheters, it is desirable to coat at least the outer cylindrical surface of the balloon that will be in contact with a blood vessel or other tissue when the balloon is inflated.

Alternatively, the anti-connexin agent can be mixed with polymers (both degradable and non degradable), for example, to hold a anti-connexin agent(s) to a stent or graft or other device, or the anti-connexin agent can be entrapped into the material of, for example, a stent or graft body, or other device.

Alternatively the anti-connexin agent can be covalently bound to, for example, a stent or other device via solution chemistry techniques or dry chemistry techniques (for example, vapour deposition methods such as rf-plasma polymerization) and combinations thereof.

Another method of coating a surface of a medical device with one or more anti-connexin agents, e.g., an anti-connexin 43 agent, comprises contacting the surface with an anti-connexin agent(s) so as to cause the surface to be coated with the particular anti-connexin agent. Coating of the artificial surface may be accomplished using the methods described in the Examples, or other methods known in the art.

For example, coating a surface with an anti-connexin agent, e.g., an anti-connexin 43 agent, can be achieved by bathing the artificial surface, either by itself or within a device, in a solution containing the anti-connexin agent. In addition, synthetic anti-connexin agents may be coated onto an artificial surface by a variety of chemical techniques which are well known in the art. Such techniques include attaching the anti-connexin agent, for example, a functionalized compound, by means of a linking group, or to a nucleophilic center, epoxide, lactone, an alpha- or beta-saturated carbon chain, alkyl halide, carbonyl group, or Schiff base, by way of a reactive group, for example, a free thiol.

A medical device may be coated using a variety of different techniques. The coating may be applied as a mixture, solution or suspension of polymeric material, for example, and one or more finely divided anti-connexin agents dispersed in an organic vehicle or a solution or partial solution of such anti-connexin agent(s) or binding compound(s) in a solvent or vehicle for the polymer and/or anti-connexin agent(s) or binding compound(s). For the purposes of this patent, the term "finely divided" means any type or size of included material from dissolved molecules through suspensions, colloids and particulate mixtures, or that otherwise serve the intended purpose. One or more anti-connexin agents can be disbursed in the carrier material, which may be the polymer, a solvent, or both, for example. The coating may be applied as a single layer or as a plurality of layers, typically relatively thin layers, sequentially applied, for example, in relatively rapid sequence. In some applications, the coating may further be characterized as a composite initial tie coat, or undercoat, and a composite topcoat. The coating thickness ratio of the topcoat to the undercoat may vary with the desired effect and/or the elution system. Typically, the topcoat and undercoat are of different formulations, but need not be. Providing an anti-connexin agent(s) and/or binding compound(s) as a plurality of layers on the medical device enables both an initial burst effect of drug elution and the drug release kinetic profile associated with long term therapeutic effect to be controlled.

Various combinations of coating materials, such as polymer coating materials, for example, can be coordinated with biologically or chemically active species of interest to produce desired effects when coated on stents or other medical devices to be implanted, or inserted, in accordance with the invention. Loadings of therapeutic materials may vary, as well as the types of therapeutic material. The mechanism of incorporation of the biologically or chemically active species into the surface coating, as well as the egress mechanism, depends both on the nature of the surface coating polymer and the therapeutic material to be incorporated. The mechanism of release also depends on the mode of incorporation. The therapeutic material may elute via interparticle paths or be administered via transport or diffusion through the encapsulating material itself.

Suitable polymers for use in the coating include, for example, a polymer that is biocompatible and minimizes irritation to the vessel wall when a medical device is implanted. It is advantageous that such polymer exhibit high elasticity/ductility, resistance to erosion, elasticity, and controlled drug release. Such polymer may be either a biostable or a bioabsorbable polymer depending on the desired rate of release or the desired degree of polymer stability. Bioabsorbable polymers that may be used include poly(L-lactic acid), polycaprolactone, poly(lactide-co-glycolide), poly(ethylene-vinyl acetate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) (e.g. PEO/PLA), polyalkylene oxalates, polyphosphazenes and biomolecules such as fibrin, fibrinogen, cellulose, starch, collagen and hyaluronic acid.

Also, biostable polymers with a relatively low chronic tissue response such as polyurethanes, silicones, and polyesters could be used and other polymers may also be used if they can be dissolved and cured or polymerized on the medical device such as polyolefins, polyisobutylene and ethylene-alphaolefin copolymers; acrylic polymers and copolymers, ethylene-co-vinylacetate, polybutylmethacrylate, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Accordingly, the coating comprising an anti-connexin agent, e.g., an anti-connexin 43 agent, may be formed, at least in part, for example, from a biodegradable or bioresorbable polymer material. Polymer materials can include, for example, but are not limited to, nylon, polyethylene perthalate, polytetrafluoroethylene, etc. Other polymers may also include, for example, hexafluoropropylene (HFP), tetrafluoroethylene (TFE), vinylidenefluoride, 1-hydropentafluoropropylene, perfluoro(methyl vinyl ether), chlorotrifluoroethylene (CTFE), pentafluoropropene, trifluoroethylene, hexafluoroacetone and hexafluoroisobutylene.

The desired release rate profile can be tailored by, for example, varying the coating thickness, the radial distribution (layer to layer) of bioactive materials, the number of layers, the mixing method, and the amount of bioactive material(s), the combination of different materials, for example, matrix polymer materials, at different layers, and the crosslink density of a polymeric material. The crosslink density is related to the amount of crosslinking which takes place and also the relative tightness of the matrix created by the particular crosslinking agent used. Thus, the curing process of such a coating typically determines the amount of crosslinking and also the crosslink density of the polymer material. For bioactive materials released from a crosslinked matrix, a crosslink structure of greater density will increase release time and reduce burst effect. By applying at least one therapeutically active anti-connexin agent at the outer layer of the medical device, a burst effect may be made to occur where a large amount of the anti-connexin agent is immediately or promptly released when it comes into contact with the tissue. Subsequently, longer term release of the anti-connexin agent will occur as it diffuses through the material, for example, a polymeric material.

The elution kinetics of an anti-connexin agent, e.g., an anti-connexin 43 agent, can be modified to meet the needs of the particular medical device application. For example, medical devices can be coated using a combination of an anti-connexin agent with one, two or more other medicaments, where the release sequence can be rate controlled. For example, one or more anti-connexin agents may be combined in the undercoat layer, and anti-thrombotic drugs, for example, heparin, may be provided in the topcoat layer. In this manner, the anti-thrombotic drugs will elute first, followed by the anti-connexin agent(s). In the case where the medical device is an implanted stent, this combination of drugs may better enable safe encapsulation of the implanted stent. Any desired drug may be included in this manner.

Alternately, the drug coating may include a base coat layer applied directly to the surfaces of the medical device, a second layer which includes a pharmacological agent, for example, an anti-connexin agent, e.g., an anti-connexin 43 agent, and a third layer in the form of a continuous membrane encapsulating the entire device. The base coat serves as a primer by readily adhering to the surface of the medical device and then readily accepting and retaining the anti-connexin agent(s) applied thereto. The base coat may include materials such as vitronectin, fibronectin, gelatin, collagen, and/or other similar materials, for example, which are relatively inexpensive and dry to form a sticky coating. An anti-connexin agent may be supplied in the form of dry, micronized particles, for example, that readily adhere to the sticky base layer surface. It is preferred that the anti-connexin agent may have a particle size of about 0.005 to about 3.0 micro meters, or such size may be different, if desired. Other particle sizes are contemplated depending on the particular medical application and device to which the anti-connexin agent(s) is/are being applied. The outer membrane or layer may encapsulate the entire medical device to cover all of its surfaces, including any bare device structure, any exposed base coating or the layer of micronized anti-connexin agent(s) or other medicament particles.

The material selected to form the membrane is dependent on its membrane forming characteristics and its biocompatibility, as well as its permeability to an anti-connexin agent, e.g., an anti-connexin 43 agent. The chemical composition of the membrane forming polymer, for example, and that of an anti-connexin agent, in combination with the thickness of the applied outer layer, will determine the diffusion rate of the anti-connexin agent.

The overall coating should be thin enough so that it will not significantly increase the profile of the medical device when inserted into a mammal. In the case of implantable stents, the coating is, for example, from between 0.005 microns to about 400 microns thick. However, other thicknesses may be utilized without departing from the spirit and scope of the present invention. The adhesion of the coating and the rate at which the drug is delivered can be controlled by the selection of an appropriate bioabsorbable or biostable material, such as a polymer, and by the ratio of the drug-to-polymer in the solution. In the case where multiple layers are utilized to coat the medical device, the release rate can be further controlled by varying the ratio of, for example, anti-connexin agent-to-polymer, in the multiple layers. For example, a higher anti-connexin agent-to-polymer ratio in the outer layers than in the inner layers would result in a higher early dose which would decrease over time.

In an alternate form, the medical device can include reservoirs, or channels, which may be loaded with one or more anti-connexin agents, e.g., an anti-connexin 43 agent. Such reservoirs can aid in decreasing the profile of the coated device, since the anti-connexin agent or a portion of the anti-connexin agent would be provided within the reservoir or channel. In such an embodiment, the anti-connexin agent is provided in the reservoirs, and a coating or membrane of biocompatible material is applied over the reservoir which controls the diffusion of the anti-connexin agent from the reservoirs to the tissue. Further layers of anti-connexin agent and/or materials, for example, polymeric materials, may be applied to the device in accordance with the teachings herein without departing from the spirit and scope of the present invention.

The amount of anti-connexin agent included in the layer(s) will vary depending on the dosage required for effective therapeutic treatment. A therapeutically effective amount of a anti-connexin agent may be determined from the doses of such compounds administered topically that typically will vary from about 0.1 micrograms to about 1 milligram or more per square millimeter or per square centimeter of device surface, in amounts ranging from about 1 micrograms to about 750 micrograms, in amounts ranging from about 5 micrograms to about 600 micrograms, in amounts ranging from about 10 micrograms to about 500 micrograms, in amounts ranging from about 20 micrograms to about 400 micrograms, in amounts ranging from about 30 micrograms to about 300 micrograms, in amounts ranging from about 50 micrograms to about 200 micrograms, and in amounts ranging from about 50 micrograms to about 100 micrograms, for example, although other amounts are contemplated and may be used, including ranges that include only the lower amounts (or the upper amounts) from the above ranges, for example, amounts ranging from about 1-10 micrograms, about 1-5 micrograms, about 10-50 micrograms, and so on (and amounts ranging from about 100-200 micrograms, about 500-600 micrograms, about 300-400 micrograms, and so on). The amounts of the anti-connexin agent will be adjusted as appropriate, in view of considerations that include, but are not limited to, the following: the dose of anti-connexin agent to be delivered locally, the rate of release of anti-connexin agent from the coating and the time period for delivery of anti-connexin agent, the size and nature of the injury, the extent of anticipated tissue damage, inflammation, and so on.

The amount of anti-connexin agent in the coating or layer is adjusted so that the desired dose of anti-connexin agent, e.g., an anti-connexin 43 agent, is delivered at the desired delivery rate for the desired time of delivery. The time of delivery will depend on factors which include the time period for which the device is intended to be implanted in the subject.

In one embodiment the coating may contain anti-connexin agent in a weight percentage of from about 0.0001% to about 30%. As noted above, depending on dose, rate of delivery, period of delivery and other factors, other amounts are contemplated and may be used. Thus, according to one option, the coating may contain anti-connexin agent in a weight percentage range of about 0.001% to about 25%, alternatively in a range of about 0.01% to about 20%, about 0.1% to about 15%, about 0.5% to about 12%, about 1% to about 10%, about 2% to about 10%, about 5% to about 10%, about 0.01% to about 5%, about 0.1% to about 5% or about 0.5% to about 5%. The weight percentage for the anti-connexin agent will be adjusted as appropriate, in view of considerations which include, but are not limited to, the following: the dose of anti-connexin agent to be delivered locally, the rate of release of anti-connexin agent from the coating and the time period for delivery of anti-connexin agent.

Other therapeutically effective dosage ranges may be useful. One skilled in the art can customize the desired rate and/or dosage of anti-connexin agent delivery by evaluation and/or selection of an appropriate bioabsorbable or biostable polymer and by the ratio of anti-connexin agent-to-polymer in the coating, for example.

The particular surface or surfaces on which the anti-connexin agent is deposited determines where the anti-connexin agent will be delivered upon implantation. For example, in the case of a stent, anti-connexin agent deposited on the outer exterior surfaces of the stent will cause the anti-connexin agent to pass directly into the lumen wall, while deposition of the anti-connexin agent on the outer interior surfaces of the stent will cause the anti-connexin agent to be released directly into the blood stream. Alternately, coating only the upstream edge or only the downstream edge of the stent may be desirable to achieve a desired effect. By selectively coating the stent, or other medical device, surfaces with the anti-connexin agent or other medicaments, the distribution of the anti-connexin agent may be precisely controlled.

It is also contemplated that artificial surfaces will vary depending on the nature of the surface, and such characteristics as contour, crystallinity, hydrophobicity, hydrophilicity, capacity for hydrogen bonding, and flexibility of the molecular backbone and polymers. Therefore, using routine methods, one of ordinary skill will be able to customize the coating technique by adjusting such parameters as the amount of anti-connexin agent, length of treatment, temperature, diluents, and storage conditions, in order to provide optimal coating of each particular type of surface.

After the device or artificial material has been coated or impregnated with one or more anti-connexin agents, it will be suitable for its intended use, for example, implantation as a heart valve, insertion as a catheter, or insertion as a stent, and so on. The coated device or artificial surface will be suitable for use in conjunction with an animal, generally mammals, including humans.

Another embodiment of an anti-connexin agent pertains to the derivatization of synthetically derived polymeric materials by attachment of a functionalized anti-connexin agent such as, for example, a functionalized compound as described herein.

Dosage Forms and Formulations

A therapeutically effective amount of each of the combination partners (e.g. an anti-connexin agent and a wound healing agent) may be administered simultaneously, separately or sequentially and in any order. The agents may be administered separately or as a fixed combination. When not administered as a fixed combination, preferred methods include the sequential administration of one or more anti-connexin agents and one or more agents useful for wound healing, either or both of which are provided in amounts or doses that are less that those used when the agent or agents are administered alone, i.e., when they are not administered in combination, either physically or in the course of treatment of a wound. Such lesser amounts of agents administered are typically from about one-twentieth to about onetenth the amount or amounts of the agent when administered alone, and may be about one-eighth the amount, about one-sixth the amount, about one-fifth the amount, about one-fourth the amount, about one-third the amount, and about one-half the amount when administered alone. Preferably, the agents are administered sequentially within at least about one-half hour of each other. The agents may also be administered with about one hour of each other, with about one day to about one week of each other, or as otherwise deemed appropriate. Preferably, the anti-connexin agent is administered first. Preferably, where one or more anti-connexin agents are used, an anti-connexin peptide or anti-connexin peptidomimetic, e.g., an anti-connexin agent that can block or reduce hemichannel opening, is administered prior to the administration of an anti-connexin agent that blocks or reduce connexin expression or the formation of hemichannels or gap junctions, e.g., by downregulation of connexin protein expression. Preferably, the anti-connexin agent or agents is/are anti-connexin 43 agent(s).

The agents of the invention of the may be administered via a medical device to a subject in need of treatment, such as a subject with any of the diseases or conditions mentioned herein. The condition of the subject can thus be improved. The anti-connexin agent and combinational partner may thus be used in the treatment of the subject's body by therapy using the device. They may be used in the manufacture of a medical device as mentioned herein. Thus, in accordance with the invention, there are provided formulations by which cell-cell communication can be downregulated in a transient and site-specific manner.

The anti-connexin agent may be present in a substantially isolated form. It will be understood that the product may be mixed with carriers or diluents which will not interfere with the intended purpose of the product and still be regarded as substantially isolated. A product of the invention may also be in a substantially purified form, in which case it will generally comprise about 90%, e.g. at least about 95%, at least about 98% or at least about 99% of the polynucleotide (or other anti-connexin agent) or dry mass of the preparation.

Depending on the intended route of application, the products of the invention may, for example, take the form of solutions, suspensions, instillations, salves, creams, gels, foams, ointments, emulsions, lotions, paints, sustained release formulations, or powders, and typically contain about 0.1%-95% of active ingredient(s), preferably about 0.2%-70% as applied to medical devices. Other suitable formulations include pluronic gel-based formulations, carboxymethylcellulose(CMC)-based formulations, and hyroxypropylmethylcellulose(HPMC)-based formulations. Other useful formulations include slow or delayed release preparations.

Gels or jellies may be produced using a suitable gelling agent including, but not limited to, gelatin, tragacanth, or a cellulose derivative and may include glycerol as a humectant, emollient, and preservative. Ointments are semi-solid preparations that consist of the active ingredient incorporated into a fatty, waxy, or synthetic base. Examples of suitable creams include, but are not limited to, water-in-oil and oil-in-water emulsions. Water-in-oil creams may be formulated by using a suitable emulsifying agent with properties similar, but not limited, to those of the fatty alcohols such as cetyl alcohol or cetostearyl alcohol and to emulsifying wax. Oil-in-water creams may be formulated using an emulsifying agent such as cetomacrogol emulsifying wax. Suitable properties include the ability to modify the viscosity of the emulsion and both physical and chemical stability over a wide range of pH. The water soluble or miscible cream base may contain a preservative system and may also be buffered to maintain an acceptable physiological pH.

Foam preparations may be formulated to be delivered from a pressurized aerosol canister, via a suitable applicator, using inert propellants. Suitable excipients for the formulation of the foam base include, but are not limited to, propylene glycol, emulsifying wax, cetyl alcohol, and glyceryl stearate. Potential preservatives include methylparaben and propylparaben.

Preferably the agents of the invention are combined with a pharmaceutically acceptable carrier or diluent to produce a pharmaceutical composition for use in or on a medical device. Suitable carriers and diluents include isotonic saline solutions, for example phosphate-buffered saline. Suitable diluents and excipients also include, for example, water, saline, dextrose, glycerol, or the like, and combinations thereof. In addition, if desired substances such as wetting or emulsifying agents, stabilizing or ph buffering agents may also be present.

The term "pharmaceutically acceptable carrier" refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, and amino acid copolymers.

Pharmaceutically acceptable salts can also be present, e.g., mineral acid salts such as hydrochlorides, hydrobromides, phosphates, sulfates, and the like; and the salts of organic acids such as acetates, propionates, malonates, benzoates, and the like.

Suitable carrier materials include any carrier or vehicle commonly used as a base for creams, lotions, gels, emulsions, lotions or paints for topical administration. Examples include emulsifying agents, inert carriers including hydrocarbon bases, emulsifying bases, non-toxic solvents or water-soluble bases. Particularly suitable examples include pluronics, HPMC, CMC and other cellulose-based ingredients, lanolin, hard paraffin, liquid paraffin, soft yellow paraffin or soft white paraffin, white beeswax, yellow beeswax, cetostearyl alcohol, cetyl alcohol, dimethicones, emulsifying waxes, isopropyl myristate, microcrystalline wax, oleyl alcohol and stearyl alcohol.

The pharmaceutically acceptable carrier or vehicle may a gel, for example a nonionic polyoxyethylene-polyoxypropylene copolymer gel, for example, a Pluronic gel, preferably Pluronic F-127 (BASF Corp.). This gel is a liquid at low temperatures but rapidly sets at physiological temperatures, which confines the release of the agent to the site of application or immediately adjacent that site.

An auxiliary agent such as casein, gelatin, albumin, glue, sodium alginate, carboxymethylcellulose, methylcellulose, hydroxyethylcellulose or polyvinyl alcohol may also be included in the formulation of the invention.

Other suitable formulations for coating or imprenating devices include pluronic gel-based formulations, carboxymethylcellulose(CMC)-based formulations, and hyroxypropylmethylcellulose(HPMC)-based formulations. The composition may be formulated for any desired form of delivery. Other useful formulations include slow or delayed release preparations.

Where the anti-connexin agent is a nucleic acid, such as a polynucleotide, uptake of nucleic acids by mammalian cells is enhanced by several known transfection techniques for example those including the use of transfection agents. Such techniques may be used with certain anti-connexin agents, including polynucleotides. The formulation which is used may contain such transfection agents. Examples of these agents include cationic agents (for example calcium phosphate and DEAE-dextran) and lipofectants (for example Lipofectam™ and Transfectam™), and surfactants.

Where the anti-connexin agent comprises a polynucleotide, the formulation may also includes a surfactant to assist with polynucleotide cell penetration or the formulation may contain any suitable loading agent. Any suitable non-toxic surfactant may be included, such as DMSO. Alternatively a transdermal penetration agent such as urea may be included.

The effective dose for a given device can be determined by routine experimentation or other methods known in the art or later developed. For example, in order to formulate a range of dosage values, cell culture assays and animal studies can be used. The dosage of such compounds preferably lies within the dose that is therapeutically effective for at least 50% of the population, and that exhibits little or no toxicity at this level.

The effective dosage of each of the anti-connexin agents employed in the devices of the invention may vary depending on a number of factors including the particular anti-connexin agent or agents employed, the combinational partner, the mode of administration, the frequency of use of the device or whether it is implanted, the condition being treated using the device, etc.

A suitable amount may be from about 0.001 to about 1 mg/kg body weight such as about 0.01 to about 0.4 mg/kg body weight. A suitable dose may however be from about 0.001 to about 0.1 mg/kg body weight such as about 0.01 to about 0.050 mg/kg body weight. Doses from about 1 to 100, 100-200, 200-300, 300-400, and 400-500 micrograms as well as 500-750 and 750-1000 micrograms are appropriate.

For example, in certain embodiments, the anti-connexin agent composition may be delivered using about 0.01 micromolar (µM) or 0.05 µM to about 200 µM final concentration at the treatment site and/or adjacent to the treatment site. Preferably, the antisense polynucleotide composition is applied at about 0.05 µM to about 100 µM final concentration, more preferably, the anti-connexin agent composition is applied at about 1.0 µM to about 50 µM final concentration, and more preferably, the anti-connexin agent composition is applied at about 5-10 µM to about 30-50 µM final concentration. Additionally, the combined anti-connexin agent composition is applied at about 8 µM to about 20 µM final concentration, and alternatively the anti-connexin agent composition is applied at about 10 µM to about 20 µM final concentration, or at about 10 to about 15 µM final concentration. In certain other embodiments, the anti-connexin agent is applied at about 10 µM final concentration. In yet another embodiment, the anti-connexin agent composition is applied at about 1-15 µM final concentration. Anti-connexin agent dose amounts include, for example, about 0.1-1, 1-2, 2-3, 3-4, or 4-5 micrograms (µg), from about 5 to about 10 µg, from about 10 to about 15 µg, from about 15 to about 20 µg, from about 20 to about 30 µg, from about 30 to about 40 µg, from about 40 to about 50 µg, from about 50 to about 75 µg, from about 75 to about 100 µg, from about 100 µg to about 250 µg, and from 250 µg to about 500 µg. Dose amounts from 0.5 to about 1.0 milligrams or more or also provided, as noted above. Dose volumes will depend on the size of the site to be treated, and may range, for example, from about 25-100 µL to about 100-200 µL, from about 200-500 µL to about 500-1000 µL. Milliliter doses are also appropriate for larger treatment sites.

Still other dosage levels between about 1 nanogram (ng)/kg and about 1 mg/kg body weight per day of each of the agents described herein. In certain embodiments, the dosage of each of the subject compounds will generally be in the range of about 1 ng to about 1 microgram per kg body weight, about 1 ng to about 0.1 microgram per kg body weight, about 1 ng to about 10 ng per kg body weight, about 10 ng to about 0.1 microgram per kg body weight, about 0.1 microgram to about 1 microgram per kg body weight, about 20 ng to about 100 ng per kg body weight, about 0.001 mg to about 100 mg per kg body weight, about 0.01 mg to about 0.1 mg per kg body weight, or about 0.1 mg to about 1 mg per kg body weight. In certain embodiments, the dosage of each of the subject compounds will generally be in the range of about 0.001 mg to about 0.01 mg per kg body weight, about 0.01 mg to about 0.2 mg per kg body weight, about 0.1 mg to about 1 mg per kg body weight. If more than one anti-connexin agent is used, the dosage of each anti-connexin agent need not be in the same range as the other. For example, the dosage of one anti-connexin agent may be between about 0.01 mg to about 1 mg per kg body weight, and the dosage of another anti-connexin agent may be between about 0.1 mg to about 0.5 mg per kg body weight.

Conveniently, the anti-connexin agent is administered in a sufficient amount to downregulate or inhibit expression of a connexin protein, or modulate gap junction formation or connexon opening for at least about 0.5 to 1 hour, at least about 1-2 hours, at least about 2-4 hours, at least about 4-6 hours, at least about 6-8 hours, at least about 8-10 hours, at least about 12 hours, or at least about 24 hours post-administration.

The dosage of each of the anti-connexin agents in the compositions and methods of the subject invention may also be determined by reference to the concentration of the composition relative to the size, length, depth, area or volume of the area to which it will be applied. For example, in certain dosing of the pharmaceutical compositions may be calculated based on mass (e.g. micrograms) of or the concentration in a pharmaceutical composition (e.g. µg/µl) per length, depth, area, or volume of the area of application.

Agents useful for wound healing suitable for the preparation of the pharmaceutical compositions described herein may be prepared and administered using methods as known in the art (see, for example, U.S. Pat. Nos. 7,098,190, 6,319,907, 6,331,298, 6,387,364, 6,455,569, 6,566,339, 6,696,433, 6,855,505, 6,900,181, 7,052,684 and EP1100529 B1. The concentration of each anti-connexin agent and agents useful for wound healing need not be in the same range as the other. Other amounts will be known to those of skill in the art and readily determined. For example, suitable combination dosages and formulations in accordance with various aspects and embodiments as described herein may be administered according to the dosing regimen as described in U.S. Pat. No. 6,903,078 to Lewis entitled "Combination PDGF, KGF, IGF, and IGFBP for wound healing."

The wound healing agent may be used in conjunction with a medical device directed towards any tissue. An effective dose of PDGF has been reported to be 5 $ng/mm^2$ or higher when applied topically as described in U.S. Pat. No. 4,861, 757, and at least 1 ng/ml local concentration of an isoform of PDGF (for example, PDGF-AA, PDGF-BB, or PDGF-AB), up to about 30 ng/ml local concentration applied to a population of fibroblasts as described in Lepisto et al., *Biochem Biophys Res. Comm* 209: 393-399 (1995). PDGF can be administered in a carboxymethylcellulose gel formulation at concentrations of about 10 µg/gm to about 500

µg/gm of gel, about 20 µg/gm to about 200 µg/gm, and about 30 µg/gm to about 100 µg/gm of gel, optimally about 100 µg/gm of gel. Efficacy of PDGF has been achieved within the range of about 3 µg/ml solution to about 300 µg/ml of solution administered.

About 50 µl of KGF of a concentration of about 5 µg/ml may be effective for wound healing by topical application to epithelial tissue as described in Sotozono et al, *Invest. Opthal. Vis. Science* 36: 1524-29 (1995). As described in U.S. Pat. No. 4,861,757, an effective amount of IGF when co-administered with PDGF is in the range of at least 2.5 ng/mm$^2$ to about 5 ng/mm$^2$, with a ratio of PDGF to IGF in the range of about 1:10 to about 25:1 weight to weight, with the most effective ratios being PDGF to IGF of about 1:1 to about 2:1 weight to weight. IGFBP administered in combination with IGF has been shown to increase wound healing at dose levels of about 5 µg of IGF with about 1.5 µg of phosphorylated IGFBP in a molar ration of about 11:1 IGF:IGFBP, as described in Jyung et al, *Surgery* 115:233-239 (1994).

For administration of polypeptide therapeutics, for example, PDGF, KGF, IGF and IGFBP polypeptides, the dosage can be in the range of about 5 µg to about 50 µg/kg of tissue to which the application is directed, also about 50 µg to about 5 mg/kg, also about 100 µg to about 500 µg/kg of tissue, and about 200 to about 250 µg/kg. For polynucleotide therapeutics, for example in a gene therapy administration protocol, depending on the expression strength the polynucleotide in the patient, for tissue targeted administration, vectors containing expressible constructs including PDGF, KGF, IGF, and IGFBP coding sequences can be administered in a range of about 100 ng to about 200 mg of DNA for local administration in a gene therapy protocol, also about 500 ng to about 50 mg, also about 1 µg to about 2 mg of DNA, about 5 µg of DNA to about 500 µg of DNA, and about 20 µg to about 100 µg during a local administration in a gene therapy protocol, and about 250 µg, per injection or administration. Factors such as method of action and efficacy of transformation and expression are therefore considerations that will effect the dosage required for ultimate efficacy for administration of DNA therapeutics. Where greater expression is desired, over a larger area of tissue, larger amounts of DNA or the same amounts re-administered in a successive protocol of administrations, or several administrations to different adjacent or close tissue portions of for example, a wound site may be required to effect a positive therapeutic outcome.

Therapeutic agents and gap junction modifying agents suitable for the preparation of the medical devices described herein may be formulated using methods as known in the art.

As noted herein, the doses of either an anti-connexin agent or another agent administered in combination can be adjusted down from the doses administered when given alone.

The combined use of several agents may reduce the required dosage for any individual agent because the onset and duration of effect of the different agents may be complementary. In a preferred embodiment, the combined use of one or more anti-connexin agents and one or more therapeutic agents, agents useful for wound healing, and/or gap junction modifying agents has an additive, synergistic or super-additive effect.

In some cases, the combination of one or more anti-connexin agents and one or more therapeutic agents and/or one or more agents useful for wound healing, and/or one or more gap junction modifying agents have an additive effect. In other cases, the combination can have greater-than-additive effect. Such an effect is referred to herein as a "supra-additive" effect, and may be due to synergistic or potentiated interaction.

The term "supra-additive promotion of wound healing" refers to a mean wound healing produced by administration of a combination of an anti-connexin agent and one or more therapeutic agents, agents useful for wound healing and/or gap junction modifying agents, is statistically significantly higher than the sum of the wound healing produced by the individual administration of either any of the agents alone. Whether produced by combination administration of an anti-connexin agent and one or more therapeutic agents, agents useful for wound healing and/or gap junction modifying agents is "statistically significantly higher" than the expected additive value of the individual compounds may be determined by a variety of statistical methods as described herein and/or known by one of ordinary skill in the art. The term "synergistic" refers to a type of supra-additive inhibition in which both the anti-connexin agent and one or more therapeutic agents, agents useful for wound healing and/or gap junction modifying agents individually have the ability to promote wound healing or reduce fibrosis and scarring. The term "potentiated" refers to type of supra-additive effect in which one of the anti-connexin agent or one or more therapeutic agents, agents useful for wound healing and/or gap junction modifying agents individually has the increased ability to promote wound healing.

In general, potentiation may be assessed by determining whether the combination treatment produces a mean wound healing increase in a treatment group that is statistically significantly supra-additive when compared to the sum of the mean wound healing increases produced by the individual treatments in their treatment groups respectively. The mean wound healing increase may be calculated as the difference between control group and treatment group mean wound healing. The fractional increase in wound healing, "fraction affected" (Fa), may be calculated by dividing the treatment group mean wound healing increase by control group mean wound healing. Testing for statistically significant potentiation requires the calculation of Fa for each treatment group. The expected additive Fa for a combination treatment may be taken to be the sum of mean Fas from groups receiving either element of the combination. The Two-Tailed One-Sample T-Test, for example, may be used to evaluate how likely it is that the result obtained by the experiment is due to chance alone, as measured by the p-value. A p-value of less than 0.05 is considered statistically significant, that is, not likely to be due to chance alone. Thus, Fa for the combination treatment group must be statistically significantly higher than the expected additive Fa for the single element treatment groups to deem the combination as resulting in a potentiated supra-additive effect.

Whether a synergistic effect results from a combination treatment may be evaluated by the median-effect/combination-index isobologram method (Chou, T., and Talalay, P. (1984) Ad. Enzyme Reg. 22:27-55). In this method, combination index (CI) values are calculated for different dose-effect levels based on parameters derived from median-effect plots of the anti-connexin agent alone, the one or more agents useful for wound healing alone, and the combination of the two at fixed molar ratios. CI values of & 1t; 1 indicate synergy, CI-1 indicates an additive effect, and CP1 indicates an antagonistic effect. This analysis may be performed using computer software tools, such as CalcuSyn, Windows Software for Dose Effect Analysis (Biosoft(D, Cambridge UK).

Any method known or later developed in the art for analyzing whether a supra-additive effect exists for a combination therapy is contemplated for use in screening for suitable anti-connexin agents for use in combination with one or more therapeutic agents, agents useful for wound healing and/or gap junction modifying agents.

In another preferred embodiment, the combined use of one or more anti-connexin agents and one or more therapeutic agents, agents useful for wound healing, and/or gap junction modifying agents reduces the effective dose of any such agent compared to the effective dose when said agent administered alone. In certain embodiments, the effective dose of the agent when used in combination with one or more anti-connexin agents is about 1/15 to about 1/2, about 1/10 to about 1/3, about 1/8 to about 1/6, about 1/5, about 1/4, about 1/3 or about 1/2 the dose of the agent when used alone.

In another preferred embodiment, the combined use of one or more anti-connexin agents and one or more therapeutic agents, agents useful for wound healing, and/or gap junction modifying agents reduces the frequency in which said agent is administered compared to the frequency when said agent is administered alone. Thus, these combinations allow the use of lower and/or fewer doses of each agent than previously required to achieve desired therapeutic goals.

In one aspect of the invention the anti-connexin agent is administered in one composition and the therapeutic agent, wound healing agent and/or gap junction modifying agent is administered in a second composition. In one embodiment the first composition comprising one or more anti-connexin agents is administered before the second composition comprising one or more therapeutic agents, agents useful for wound healing and/or gap junction modifying agents. In one embodiment the first composition comprising one or more anti-connexin agents is administered after the second composition comprising one or more therapeutic agents, agents useful for wound healing and/or gap junction modifying agents. In one embodiment the first composition comprising one or more anti-connexin agents is administered via the medical device before and after the second composition comprising one or more therapeutic agents, agents useful for wound healing and/or gap junction modifying agents. In one embodiment the first composition comprising one or more anti-connexin agents is administered via the medical device about the same time as the second composition comprising one or more therapeutic agents, agents useful for wound healing and/or gap junction modifying agents.

Preferably one or more anti-connexin agents and one or more therapeutic agents, agents useful for wound healing and/or gap junction modifying agents are delivered by topical application via the medical device, including but not limited to application using solid supports (such as matrices) and medicinal layers or coatings as described herein or otherwise known in the art. In one embodiment, the solid support comprises a biocompatible membrane. In another embodiment, the solid support comprises a matrix. In one embodiment of the invention, the solid support composition may be a slow release solid support composition, in which the one or more anti-connexin agents and one or more therapeutic agents, agents useful for wound healing and/or gap junction modifying agents is dispersed in a slow release solid matrix such as a matrix of alginate, collagen, or a synthetic bioabsorbable polymer. Preferably, the solid support composition is sterile or low bio-burden.

The delivery of one or more anti-connexin agents and one or more therapeutic agents, agents useful for wound healing and/or gap junction modifying agents of the formulation over a period of time via the medical device, in some instances for about 1-2 hours, about 2-4 hours, about 4-6 hours, about 6-8, or about 24 hours or longer, may be a particular advantage in implanted devices. In some instances, cell loss may extend well beyond the site of a procedure to surrounding cells. Such loss may occur within 24 hours of the original procedure and is mediated by gap junction cell-cell communication. Administration of anti-connexin agent(s), e.g., for downregulation or inhibition of connexin expression, or blockade of connexon opening, therefore will modulate communication between the cells, or loss into the extracellular space in the case of connexon regulation, and minimize additional cell loss or injury or consequences of injury.

While the delivery period will be dependent upon both the site at which the downregulation is to be induced and the therapeutic effect which is desired, continuous or slow-release delivery via the medical device for about 1-2 hours, about 2-4 hours, about 4-6 hours, about 6-8, or about 24 hours or longer is provided. In accordance with the present invention, this is achieved by inclusion of the anti-connexin agents and/or one or more therapeutic agents, agents useful for wound healing and/or gap junction modifying agents in a medical device together with a pharmaceutically acceptable carrier, coating, layer or other vehicle, particularly in a form for continuous or slow-release administration.

Various aspects of the invention will now be described with reference to the following experimental section which will be understood to be provided by way of illustration only and not to constitute a limitation on the scope of the invention.

EXAMPLES

Example 1

Determination of Effects from Use of an Anti-Connexin Agent-Treated Device in an Animal Model The following experiment is directed to coating artificial surfaces with an anti-connexin agent for amelioration of tissue damage and/or enhanced tissue repair and their testing in an animal model.

Materials:

Sodium bicarbonate, sodium chloride, sodium phosphate, sodium nitrite, potassium phosphate-monobasic, 40% formaldehyde solution and sucrose are available from Fischer Scientific, Fairlawn, N.J. Sephadex G25 is available from Pharmacia, Piscataway, N.J. Monoclonal mouse anti-proliferating cell nuclear antigen is available from Dako A/S, Denmark. All other chemicals are available from Sigma Chemical Co., St. Louis, Mo.

Tris-buffered saline consisted of 10 mM tris[hydroxymethyl]aminoethane, pH 7.4, and 150 mM NaCl. Phosphate-buffered saline contained 10 mM sodium phosphate and 150 mM NaCl, pH 7.4.

Anti-Connexin Agent Species:

Anti-connexin agent-BSA is synthesized as follows: Fatty acid-free bovine serum albumin (200 mg/ml) is exposed to a 1.4 molar-fold excess of anti-connexin agent in PBS for 30 minutes at room temperature.

Thiolated bovine serum albumin (pS-BSA) is prepared after Benesch and Benesch (Benesch R & Benesch R E, "Preparation and properties of hemoglobin modified with derivatives of pyridoxal". Methods Enzymol., 76:147-159 (1981)). Briefly, essential fatty acid-free bovine serum albumin (50 mg/ml) is dissolved in water with N-acetyl-homocysteine thiolactone (35 mM) and 0.05% polyethylenesorbitan monolaurate. Equimolar Silver nitrate is slowly added at room temperature over 90 minutes at pH 8.5. Excess thiourea (70 mM) is added and the pH lowered to 2.5. Excess silver nitrate is removed by Dowex 50 chromatography with the mobile phase consisting of 1M thiourea, pH 2.5, and excess thiourea is removed by Sephadex G-25 chromatography. The pS-BSA is prepared within two days of subsequent derivitization and stored at 4° C. Derivitization of pS-BSA is accomplished with 1.4 fold molar excess S-triethylenetetramine in 0.5 N HCl for 30 minutes at room temperature. The solution is adjusted to pH 4.0 with 0.5 N NACH after derivitization. Protein content is determined using the method of Lowry and colleagues (Marcus Salier, FASEB. J., 7:516-522, 1993).

Animal Preparation:

All animal preparations are performed within institutional guidelines of the host institution. New Zealand white rabbits (3.5-4.2 kg) of either sex are premedicated with 5 mg/kg intramuscular (IM) xylazine hydrochlolide (Miles Pharmaceuticals, Shawnee Mission, Kans.), and 0.1 mg/kg subcutaneous (SC) atropine sulfate (Lyphomed, Deerfield, Ill.) fifteen minutes prior to the induction of anesthesia. Anaesthesia is induced with 40 mg/kg IM ketamine hydrochloride (Fort Dodge Laboratories, Fort Dodge, Iowa) and 5 mg/kg IM acepromazine maleate (Aveco Company, Inc., Fort Dodge, Iowa). Additional doses of ketamine hydrochloride are administered as necessary to maintain anesthesia. For survival studies, 100,000 U penicillin G (Apothecon of Bristol-Myers Squibb, Princeton, N.J.), is administered IM perioperatively. The skin over the femoral arteries is infiltrated with 1% lidocaine (Astra Pharmaceuticals, Inc., Westborough, Mass.), and the common femoral arteries are exposed from the inguinal ligament to the superficial femoral artery. Arteries are cleared of connective tissue, side branches are ligated, and the superficial femoral artery is suspended with silk ties. A 1.5-to-2.0 cm length of femoral artery is isolated from the circulation proximally and distally with neurosurgical microaneurysm clips. The superficial femoral artery is cannulated with a S-triethylenetetramine-BSA coated 2F Fogarty balloon catheter (American Edwards Laboratories, Santa Ana, Calif.), that is passed into the isolated segment of femoral artery. The balloon is inflated with sufficient air to generate slight resistance and withdrawn three times. The contralateral femoral artery is prepared identically as an appropriate control, i.e., using a balloon catheter coated with underivatized BSA. Following removal of the balloon catheter, the superficial femoral artery is ligated and flow re-established. The area of balloon injury is marked by surgical staples in the adjacent muscle fascia. The incision is closed with subcuticular absorbable suture and the animals allowed to recover. In some experiments, a distant control vessel, the right carotid artery, is isolated and harvested without any other manipulation.

Tissue Processing and Analysis:

On the 14th postoperative day, animals are euthanized with 120 mg/kg intravenous sodium pentobarbital (Anpro Pharmaceuticals, Arcadia, Calif.), and the abdominal aorta and inferior vena cava interrupted by silk ties. A 7F plastic cannula is inserted into the abdominal aorta and the vessels perfused clear with saline followed by fixation at 100 mm Hg pressure with 10% buffered formalin. The vessels are stored in 10% buffered formalin and the samples paraffin-embedded and microtome-sectioned. Six sections are made along the length of each injured segment of vessel and stained with Verhoeff's stain for elastic tissue. The areas within the lumen, internal elastic membrane, and external elastic membrane are measured by a blinded observer using computerized digital planimetry (Zeiss, West Germany). The areas within the lumen, internal elastic membrane and external elastic membrane are analyzed. Sections with obstructive thrombus impairing analysis are discarded.

In a separate set of animals, vessels are perfusion-fixed with 10% buffered formalin seven days after injury and processed for analysis of proliferating cells within 12 hours. Sections are stained for proliferating cell nuclear antigen (PCNA) and adjacent sections are stained with hematoxylin and eosin. Five representative sections from each segment are examined. Total nuclei are counted from the hematoxylin and eosin slides and percent PCNA positive cells are defined as the number of PCNA-positive nuclei divided by the total number of nuclei multiplied by 100.

Statistics:

Treatments are administered in a paired fashion with one femoral artery cannulated with an anti-connexin agent-BSA coated balloon catheter while the other femoral artery is cannulated with an underivatized BSA coated balloon catheter. Data is tested for normality using appropriate statistical methods, for example, the Kolmogorov-Smirnov algorithm and for equal variance with the Levene Median test. Normally distributed variables are compared using, for example, the paired t-test and non-normally distributed variables using, for example, the Wilcoxon sign-ranks test or the Mann-Whitney rank-sum test. Non-paired data are compared using, for example, an independent t-test. Statistical significance is accepted if the null hypothesis is rejected with $P<0.05$.

Anti-Connexin Agent-BSA Effect on Platelet Binding to Injured Vessel:

Platelet adhesion to the injured arterial surface has been reported to be important in the proliferative response to injury. Accordingly the effects of anti-connexin agent-BSA on platelet deposition after balloon injury are investigated. Platelet deposition is assessed at the site of cannulation with anti-connexin agent-BSA coated balloon catheter, and compared to that at the site of cannulation with an underivatized BSA coated balloon catheter. Decreased platelet deposition at the site of cannulation with anti-connexin agent-BSA coated balloon catheter is indicative of ameliorated tissue damage and/or enhanced tissue repair.

Anti-Connexin Agent-BSA Effects on Neointimal Proliferation:

Neointimal proliferation after local delivery of anti-connexin agent-BSA and appropriate controls are evaluated by comparing absolute neointimal area and neointima/media ratios. The absolute neointimal area and neointima/media ratio at the site of cannulation with an anti-connexin agent-BSA coated balloon catheter is assessed and compared to a neointimal area and neointima/media ratio at the site of cannulation with an underivatized BSA coated balloon catheter. A decrease in neointimal area or reduction in the neointima/media ratio is indicative of an inhibition of neointimal proliferation and of amelioration of tissue damage and/or enhanced tissue repair.

Anti-Connexin Agent-BSA Effects on Cellular Proliferation:

Mouse monoclonal antibody staining against PCNA is used to assay the degree of S1-phase activity at 7 days after injury. At this time, the percent of proliferating cells is assessed in vessels cannulated with an anti-connexin agent-BSA coated balloon catheter and in vessels cannulated with an underivatized BSA coated balloon catheter. Histological assessment determines the cellular populations undergoing proliferation.

These experiments are directed to the effect on neointimal proliferation and amelioration of tissue damage and/or enhanced tissue repair by localised delivery of an anti-connexin agent by, for example, the coating of a balloon catheter with anti-connexin agent-BSA.

The endothelium is reported to be essential for vascular integrity, control of thrombosis, (Clowes et al., Lab. Invest. 49:327-333, 1983); (Rees et al., Proc. Natl. Acad. Sci. USA. 86:3375-3378, 1989) and the regulation of intimal growth (Kubes et al., Proc. Natl. Acad. Sci. USA, 88:4651-4655, 1991), and has been proposed to be important in the local control of vascular smooth muscle growth. Balloon angioplasty reportedly removes the endothelium from arterial smooth muscle, and these endothelial functions can often be lost during the procedure. In particular, removal of the endothelium and damage to the smooth muscle cells have been reported to be associated with intimal proliferation (McNamara et al., Biochem. Biophys. Res. Commun., 193: 291-296, 1993). The mechanism for this response is complex and reportedly involves platelet deposition and activation, cytokine elaboration, smooth muscle cell migration and proliferation, and extra-cellular matrix production. It has been reported that after balloon injury, the endothelium regenerates rapidly but is often dysfunctional, (Saville, Analyst 83:670-672, 1958).

A limitation of neointimal proliferation after a single, local administration of an anti-connexin agent is indicative of amelioration of tissue damage and/or enhanced tissue repair. Antiplatelet activity may explain such findings. Inhibition of platelet binding has been said to result in many effects that are likely to reduce the proliferative response after injury. For example, platelet adhesion and aggregation is said to be associated with the release of PDGF, basic fibroblast growth factor, epidermal growth factor, and transforming growth factor-β, potent stimuli for smooth muscle cell proliferation and matrix production.

There may additionally or alternatively be a direct effect on vascular smooth muscle gene expression, migration, proliferation or synthesis of extracellular matrix. Such an effect may be in addition to an amelioration of tissue damage and/or enhancement in tissue repair by, for example, restoration of normal tissue stem cell responses.

It has been reported that the mechanical removal of the endothelium abolishes the vasodilator responses to endothelium-dependent vasoactive stimuli, while leaving the vasoconstrictor effects of agonists to smooth muscle unopposed (Furchgott Zawadzki, Nature 288:373-376 (1980). This process reportedly occurs with balloon angioplasty especially at sites where platelet thrombus is noted (Uchida et al., Am. Heart. J., 117:769-776 (1989); Steele et al., Circ. Res., 57:105-112 (1985). The strategy of administration of an anti-connexin agent as therapy for, for example, acute thrombotic phenomena and restenosis following angioplasty is supported by results indicating an amelioration of tissue damage and/or enhancement in tissue repair.

Example 2

Preparation and Use of an Anti-Connexin Agent Coated Medical Device for Ameliorating Tissue Damage and/or Enhancing Tissue Repair The following experiment is directed to application of anti-connexin agents to coated artificial surfaces, such as, for example, synthetic vascular graft material, or stents, for use in ameliorating tissue damage and/or enhancing tissue repair.

First, dacron grafts and cardiac catheters are coated with a functionalized anti-connexin agent, such as for example, anti-connexin agent-bovine serum albumin (BSA). In three separate experiments, an identical pair of 6 mm (internal diameter) knitted dacron grafts, 5 cm in length, are prepared for surgical placement in the transected carotid arteries of six anesthetized dogs. For each experiment, three control dogs receive grafts coated in underivatized BSA, while for each of the three trial dogs, one graft is soaked in 5% BSA and the other graft is soaked in 5% BSA combined with 0.5 mM anti-connexin agent producing, anti-connexin agent-BSA, an example of a functionalized anti-connexin agent protein, for one hour prior to insertion, and then rinsed in saline. The grafts are sutured in place with a continuous 6-0 proline suture.

Following graft insertion, the dogs are observed for two months.

Histological examination of the site of insertion is performed at the end of the two month period. Amelioration of tissue damage or enhanced tissue repair is evidenced by, for example, the appearance of normal vascular epithelial cells at the site of graft insertion. Tissue repair at the site of anti-connexin agent-BSA-coated graft insertion is compared to that at the site of underivatized, BSA-coated graft insertion.

Evidence of amelioration of tissue damage and/or enhanced tissue repair at the site of anti-connexin agent-BSA coated graft insertion compared to that at the site of underivatized BSA-coated graft insertion is shown by amelioration of tissue damage and/or enhanced tissue repair at the site of insertion of the synthetic grafts treated with anti-connexin agent-BSA during exposure of the graft to circulating blood over a period of two months.

Example 3

Application of Anti-Connexin Agents to Damaged Vascular Surfaces to Ameliorate Tissue Damage and/or Enhance Tissue Repair The following experiment is directed to application of anti-connexin agents to damaged vascular surfaces, for example, arterial surfaces, to ameliorate tissue damage and/or enhance tissue repair.

In five anesthetized dogs, both carotid arteries are exposed. Two 3 FR USC1 catheters are prepared for arterial implantation. One catheter is soaked in a 5% BSA solution for 12 hours, while the other is soaked in a 5% BSA solution which also contains 1 mg/ml of test anti-connexin agent. One each of the two coated catheters is placed randomly in the right or left carotid artery of the dog through a small incision sealed with a 6-0 proline suture. The catheters are advanced for 5 cm into the arterial lumen. Following catheter insertion, the dogs are observed for two weeks.

Histological examination of the site of insertion is performed at the end of the two week period. Lessened tissue damage, and/or tissue repair, is evidenced by, for example, the appearance of normal vascular epithelial cells at the site of catheter insertion. Tissue at the site of anti-connexin agent-BSA coated catheter insertion is compared to that at the site of underivatized BSA-coated catheter insertion.

Evidence of enhanced tissue repair and/or amelioration of tissue damage at the site of anti-connexin-BSA coated catheter insertion compared to that at the site of underivatized BSA-coated catheter insertion is shown by enhanced tissue repair and/or amelioration of tissue damage at the site of insertion of the catheter treated with anti-connexin agent-BSA during exposure of the catheter to circulating blood over a period of two weeks.

Example 4

Determination of Tissue Damage Using an Anti-Connexin Agent Treated Medical Device in a Pig Model The following experiment is directed to determining the tissue damage using a treated medical device in a pig model.

Pigs are subjected to coronary balloon-injury using standard methods. Prior to balloon injury, an angiogram is performed. Thereafter, in trial pigs, a test anti-connexin agent-BSA coated balloon catheter, for example, is used for balloon injury, whereas in control pigs, an underivatized BSA coated balloon catheter is used. The balloon of the catheter is inflated for 15 min, then deflated and the catheter is removed. Another angiogram is performed 30 minutes after injury to determine the degree of spasm. Coronary catheters are placed in the coronary ostea, radiocontrast is infused into the coronary arteries and measurements are made of the degree of so-called "recoil spasm" that exists at the point of angioplasty. The degree of spasm or recoil is defined quantitatively, again using the computer-driven quantitative coronary angiography algorithm that compares the segment at the site of balloon injury with a proximal segment that is uninjured as a reference standard. All catheters are then removed and incision sites repaired. The animals are awakened and maintained with normal chow diets over the next four weeks. At the end of that period of time, the animals are again sedated, undergo coronary angiography to determine coronary stenoses at the site of angioplasty. Catheters are placed in the coronary ostea and radiocontrast fluid is infused. The angiograms are recorded and subsequently processed by a computer-driven quantitative coronary angiography algorithm to determine lumen diameter. The degree of stenosis represents the percentage reduction in the lumen diameter compared with a reference segment proximal to the area of stenosis using standard methods. The animals are euthanized by an overdose of pentobarbital. Their coronary arteries are perfusion fixed with formalin at 100 mm Hg of perfusion pressure, harvested and sectioned for quantitative morphometric assessment of the lumen diameter, the neointimal dimension and cross-section, as well as the neointimal area. The arteries are stained with hematoxylin and eosin. The neointima to lumen diameter ratio is determined and is compared between trial and control animals.

Example 5

Determination of Effect on Tissue Damage and/or Tissue Repair Using an Anti-Connexin Agent Coated Medical Device This experiment is directed to coating a Palmaz-Schatz stent with an anti-connexin agent to reduce the degree and severity of neointimal hyperplasia leading to restenosis. Palmaz-Schatz stents are dip-coated in 800-1000 µM test anti-connexin agent-BSA, for example, or underivatized BSA three times for 10 minutes followed by 10 minutes of air drying time. One test anti-connexin agent-BSA coated and one underivatized BSA-coated stent is placed under sterile conditions in the carotid arteries of 10 pigs, one in each carotid artery. They are followed for 28 days and then the carotid arteries are removed. They are examined histologically for the degree of neointimal hyperplasia, and tissue damage/repair. Tissue repair is evidenced by, for example, the appearance of normal vascular epithelial cells at the site of insertion of the stent. Tissue damage/repair at the site of test anti-connexin agent-BSA coated stent insertion is compared to that at the site of underivatized BSA-coated stent insertion.

Evidence of amelioration of tissue damage and/or enhanced tissue repair at the site of test anti-connexin agent-BSA coated stent insertion compared to that at the site of underivatized BSA-coated stent insertion shows that during exposure of the stent to circulating blood, there is amelioration of tissue damage and/or enhanced tissue repair at the site of insertion of the stent coated with anti-connexin agent, and that delivery of an anti-connexin agent is able to ameliorate tissue damage enhance tissue repair.

Example 6

Method of Coating Pharmaceutical Agents onto Sutures

A 4-0 VICRYL (Polyglactin 910) Suture (Ethicon, Somerville, N.J.) is coated with suitable anti-connexin agent and gelatin. The coating solution comprises of 4 ml gelatin solution and 2 ml of anti-connexin agent solution. The gelatin component is prepared by heating a 10 wt % solution of medical grade soluble bovine collagen (Semed-S, Kensey-Nash, Exton, Pa.) to 80° C. for 10 minutes followed by incubation at 37° C. The anti-connexin agent, e.g., an anti-connexin 43 agent (for example, a connexin 43 antisense ODN, or an anti-connexin 43 peptide or peptidomimetic, such as one that blocks or inhibits hemichannel opening), is prepared at suitable concentrations, such as, for example, 10, 3, 0.6, and 0 µg/ml. The resulting concentrations in the coating solutions can then be determined. The coating solutions are kept at 37° C. until use. Prior to coating, the sutures are pretreated with a bath of 70% ethanol solution for 10 minutes, followed by a wash with saline. The suture is then placed in the coating solution and incubated at 37° C. for 30 minutes with gentle agitation. The suture is then removed from the solution and is then air-dried overnight.

The concentration of the anti-connexin agent on the suture is quantified by an ELISA method. The anti-connexin agent is first eluted from a 4 cm segment of suture in 2 ml of 6M Urea solution (75 mM NaH2PO 4, pH 2.7) at 37° C. for 1 hour. The elution solutions are analyzed by a sandwich ELISA assay that detects the presence of the anti-connexin agent. The concentration of the anti-connexin agent on the suture is measured in µg/cm.

Example 7

A 0 ETHIBOND EXCEL Polyester Suture (Ethicon, Somerville, N.J.) is coated with anti-connexin agent and gelatin in a similar manner as described in Example 6. An anti-connexin agent solution is concentrated to appropriate concentration (in mg/ml) with a centrifugal filter device (e.g. Centriplus YM-10, Regenerated Cellulose 10,000 MWCO, Amicon Bioseparations). The coating solution comprises of 0.5 ml concentrated anti-connexin solution and 1 ml 10 wt % gelatin solution. The concentration of anti-connexin solution on the coated suture, as quantified by ELISA, is then measured.

Sutures are pulled through a sample of goat ACL tissue to evaluate if any of the anti-connexin agent coating is sheared off during its use. The concentration of anti-connexin agent post-surgery is measured. If appropriate concentration is obtained, it is an indication that the gelatin is effective in maintaining the anti-connexin agent on the suture even while passing through tissue.

Preferred anti-connexin agents for sutures areanti-connexin 43 agent, particularly connexin 43 antisense (e.g., ODN) molecules, or an anti-connexin 43 peptide or peptidomimetic, such as one that blocks or inhibits hemichannel opening), or both together, Example 8

A 0 Plain Surgical Gut Suture (Ethicon, Somerville, N.J.) is coated with anti-connexin agent. The coating solution comprises of 1 ml anti-connexin agent solution concentrated to the appropriate concentration (in mg/ml) with a centrifugal filter device (e.g. Centriplus YM-10, Regenerated Cellulose 10,000 MWCO, Amicon Biosepartions). The gut suture is pretreated in a bath of 200 mM NaH 2PO4 (pH 11.2) for 10 minutes followed by a wash in PBS prior to coating. The concentration of the anti-connexin coating on the coated gut suture is then quantified by ELISA assay.

Example 9

A partially resorbable composite suture (e.g., 2 ORTHO-CORD Orthopaedic Suture, DePuy Mitek, Raynham, Mass.) is coated with anti-connexin agent and gelatin in a similar manner as described in Example 6. The coating solution comprises of suitable volume of anti-connexin agent solution at a desired concentration (e.g. 3.5 mg/ml and 1.4 ml 10 wt % gelatin solution). The concentration of the anti-connexin agent on the coated partially resorbable composite suture is then quantified by ELISA (e.g. µg/cm).

All patents, publications, scientific articles, web sites, and other documents and materials referenced or mentioned herein are indicative of the level of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, not specifically disclosed herein as essential. Thus, for example, in each instance herein, in embodiments or examples of the present invention, the terms "comprising", "including", "containing", etc. are to be read expansively and without limitation. In particular, the phrase "for example" shall be interpreted to mean "for example, and including but not limited to." The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

Other embodiments are within the following claims. Under no circumstances may the patent be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention claimed is:

1. A method of preventing and/or treating inflammation, blood vessel leakage, and/or fibrosis associated with the use or implantation of medical device selected from an ophthalmic implant in a subject comprising introducing into the subject the medical device of which at least a portion comprises an anticonnexin 43 antisense compound releasable upon insertion of the medical device to or within a subject, wherein the inflammation, blood vessel leakage, and/or fibrosis is prevented, ameliorated and/or delayed.

2. The method of claim 1, wherein the ophthalmic implant is a glaucoma shunt.

3. The method of claim 1, wherein the subject is a mammal.

4. The method of claim 1, wherein the mammal is a human.

5. The method of claim 1, wherein the anti-connexin 43 antisense compound decreases connexin 43 protein expression.

6. The method of claim 1, wherein the anti-connexin 43 antisense compound is an oligodeoxynucleotide.

7. The method of claim 1, wherein the anti-connexin 43 antisense compound is a siRNA or RNAi oligonucleotide.

8. The method of claim 1, wherein the anti-connexin 43 antisense compound binds to connexin 43 mRNA.

9. The method of claim 1, wherein the anti-connexin antisense compound binds to a connexin 43 hemichannel.

10. The method of claim 1, wherein the anti-connexin antisense compound binds to a hemichannel extracellular loop.

11. The method of claim 1, wherein the anti-connexin antisense compound is a polynucleotide having a sequence according to SEQ ID NO:1 or a pharmaceutically acceptable salt thereof.

12. The method of claim 1, wherein the anti-connexin antisense compound is a polynucleotide having a sequence according to SEQ ID NO:2 or a pharmaceutically acceptable salt thereof.

13. The method of claim 1, wherein the surface of the medical device comprises an anti-connexin antisense compound.

14. The method of claim 13, wherein the anti-connexin antisense compound is present at a weight percentage of about 0.0001% to about 30%.

15. The method of claim 13, wherein the surface of the medical device contacts a target tissue within the subject upon use.

16. The method of claim 1, wherein the release rate of the anti-connexin antisense compound is controlled.

17. The method of claim 1, wherein the medical device provides for surface contact release of the anti-connexin antisense compound.

18. The method of claim 1, wherein the medical device provides for the sustained release of the anti-connexin antisense compound.

19. The method of claim 1, wherein the medical device provides for the slow release of the anti-connexin antisense compound.

20. The method of claim 1, wherein the device comprises a coating containing an anti-connexin antisense compound.

21. The method of claim 20, wherein the coating comprises a polymer.

22. The method of claim 21, wherein the coating comprises a plurality of layers of a polymer/anti-connexin antisense compound mixture.

23. The method of claim 1, wherein the medical device comprises at least one channel formed in an outer surface thereof, and wherein the anti-connexin antisense compound is included on and/or within at least one channel.

24. The method of claim 1, wherein at least a portion of the medical device is formed, in whole or in part, of a substance that includes the anti-connexin antisense compound.

25. The method of claim 1, wherein the device further comprises one or more therapeutic agents.

26. The method of claim 1 or 2, wherein inflammation is prevented or ameliorated.

27. The method of claim 1 or 2, wherein blood vessel leakage is prevented or ameliorated.

28. The method of claim 1 or 2, wherein fibrosis is prevented or ameliorated.

29. The method of claim 6, wherein the anti-connexin 43 antisense oligodeoxynucleotide is chemically unmodified.

30. The method of claim 6, wherein the anti-connexin 43 antisense oligodeoxynucleotide is chemically modified.

* * * * *

SEQUENCE LISTING

<160> NUMBER OF SEQ ID NOS: 135

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gtaattgcgg caagaagaat tgtttctgtc                                        30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtaattgcgg caggaggaat tgtttctgtc                                        30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggcaagagac accaaagaca ctaccagcat                                        30

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tcctgagcaa tacctaacga acaaata                                           27

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
catctccttg gtgctcaacc                                                   20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ctgaagtcga cttggcttgg                                                   20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ctcagatagt ggccagaatg c                                             21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ttgtccaggt gactccaagg                                               20

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cgtccgagcc cagaaagatg aggtc                                         25

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
agaggcgcac gtgagacac                                                19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tgaagacaat gaagatgtt                                                19

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tttcttttct atgtgctgtt ggtga                                         25

<210> SEQ ID NO 13
<211> LENGTH: 396
<212> TYPE: PRT
<213> ORGANISM: Homo sapiens

<400> SEQUENCE: 13

```
Met Ser Trp Ser Phe Leu Thr Arg Leu Leu Glu Glu Ile His Asn His
  1               5                  10                  15

Ser Thr Phe Val Gly Lys Ile Trp Leu Thr Val Leu Ile Val Phe Arg
             20                  25                  30

Ile Val Leu Thr Ala Val Gly Gly Glu Ser Ile Tyr Tyr Asp Glu Gln
         35                  40                  45

Ser Lys Phe Val Cys Asn Thr Glu Gln Pro Gly Cys Glu Asn Val Cys
 50                  55                  60

Tyr Asp Ala Phe Ala Pro Leu Ser His Val Arg Phe Trp Val Phe Gln
 65                  70                  75                  80

Ile Ile Leu Val Ala Thr Pro Ser Val Met Tyr Leu Gly Tyr Ala Ile
                 85                  90                  95

His Lys Ile Ala Lys Met Glu His Gly Glu Ala Asp Lys Lys Ala Ala
            100                 105                 110

Arg Ser Lys Pro Tyr Ala Met Arg Trp Lys Gln His Arg Ala Leu Glu
        115                 120                 125

Glu Thr Glu Glu Asp Asn Glu Glu Asp Pro Met Met Tyr Pro Glu Met
130                 135                 140

Glu Leu Glu Ser Asp Lys Glu Asn Lys Glu Gln Ser Gln Pro Lys Pro
145                 150                 155                 160

Lys His Asp Gly Arg Arg Ile Arg Glu Asp Gly Leu Met Lys Ile
                165                 170                 175

Tyr Val Leu Gln Leu Leu Ala Arg Thr Val Phe Glu Val Gly Phe Leu
                180                 185                 190

Ile Gly Gln Tyr Phe Leu Tyr Gly Phe Gln Val His Pro Phe Tyr Val
        195                 200                 205

Cys Ser Arg Leu Pro Cys Pro His Lys Ile Asp Cys Phe Ile Ser Arg
    210                 215                 220

Pro Thr Glu Lys Thr Ile Phe Leu Leu Ile Met Tyr Gly Val Thr Gly
225                 230                 235                 240

Leu Cys Leu Leu Leu Asn Ile Trp Glu Met Leu His Leu Gly Phe Gly
                245                 250                 255

Thr Ile Arg Asp Ser Leu Asn Ser Lys Arg Arg Glu Leu Glu Asp Pro
            260                 265                 270

Gly Ala Tyr Asn Tyr Pro Phe Thr Trp Asn Thr Pro Ser Ala Pro Pro
        275                 280                 285

Gly Tyr Asn Ile Ala Val Lys Pro Asp Gln Ile Gln Tyr Thr Glu Leu
    290                 295                 300

Ser Asn Ala Lys Ile Ala Tyr Lys Gln Asn Lys Ala Asn Thr Ala Gln
305                 310                 315                 320

Glu Gln Gln Tyr Gly Ser His Glu Glu Asn Leu Pro Ala Asp Leu Glu
                325                 330                 335

Ala Leu Gln Arg Glu Ile Arg Met Ala Gln Glu Arg Leu Asp Leu Ala
            340                 345                 350

Val Gln Ala Tyr Ser His Gln Asn Asn Pro His Gly Pro Arg Glu Lys
        355                 360                 365

Lys Ala Lys Val Gly Ser Lys Ala Gly Ser Asn Lys Ser Thr Ala Ser
    370                 375                 380
```

Ser Lys Ser Gly Asp Gly Lys Asn Ser Val Trp Ile
385                 390                 395

<210> SEQ ID NO 14
<211> LENGTH: 382
<212> TYPE: PRT
<213> ORGANISM: Homo sapiens

<400> SEQUENCE: 14

Met Gly Asp Trp Ser Ala Leu Gly Lys Leu Leu Asp Lys Val Gln Ala
1               5                   10                  15

Tyr Ser Thr Ala Gly Gly Lys Val Trp Leu Ser Val Leu Phe Ile Phe
                20                  25                  30

Arg Ile Leu Leu Leu Gly Thr Ala Val Glu Ser Ala Trp Gly Asp Glu
            35                  40                  45

Gln Ser Ala Phe Arg Cys Asn Thr Gln Gln Pro Gly Cys Glu Asn Val
        50                  55                  60

Cys Tyr Asp Lys Ser Phe Pro Ile Ser His Val Arg Phe Trp Val Leu
65                  70                  75                  80

Gln Ile Ile Phe Val Ser Val Pro Thr Leu Leu Tyr Leu Ala His Val
                85                  90                  95

Phe Tyr Val Met Arg Lys Glu Glu Lys Leu Asn Lys Lys Glu Glu Glu
                100                 105                 110

Leu Lys Val Ala Gln Thr Asp Gly Val Asn Val Asp Met His Leu Lys
            115                 120                 125

Gln Ile Glu Ile Lys Lys Phe Lys Tyr Gly Ile Glu Glu His Gly Lys
        130                 135                 140

Val Lys Met Arg Gly Gly Leu Leu Arg Thr Tyr Ile Ile Ser Ile Leu
145                 150                 155                 160

Phe Lys Ser Ile Phe Glu Val Ala Phe Leu Leu Ile Gln Trp Tyr Ile
                165                 170                 175

Tyr Gly Phe Ser Leu Ser Ala Val Tyr Thr Cys Lys Arg Asp Pro Cys
                180                 185                 190

Pro His Gln Val Asp Cys Phe Leu Ser Arg Pro Thr Glu Lys Thr Ile
            195                 200                 205

Phe Ile Ile Phe Met Leu Val Val Ser Leu Val Ser Leu Ala Leu Asn
        210                 215                 220

Ile Ile Glu Leu Phe Tyr Val Phe Phe Lys Gly Val Lys Asp Arg Val
225                 230                 235                 240

Lys Gly Lys Ser Asp Pro Tyr His Ala Thr Ser Gly Ala Leu Ser Pro
                245                 250                 255

Ala Lys Asp Cys Gly Ser Gln Lys Tyr Ala Tyr Phe Asn Gly Cys Ser
                260                 265                 270

Ser Pro Thr Ala Pro Leu Ser Pro Met Ser Pro Pro Gly Tyr Lys Leu
            275                 280                 285

Val Thr Gly Asp Arg Asn Asn Ser Ser Cys Arg Asn Tyr Asn Lys Gln
        290                 295                 300

Ala Ser Glu Gln Asn Trp Ala Asn Tyr Ser Ala Glu Gln Asn Arg Met
305                 310                 315                 320

Gly Gln Ala Gly Ser Thr Ile Ser Asn Ser His Ala Gln Pro Phe Asp
                325                 330                 335

Phe Pro Asp Asp Asn Gln Asn Ser Lys Lys Leu Ala Ala Gly His Glu
            340                 345                 350

Leu Gln Pro Leu Ala Ile Val Asp Gln Arg Pro Ser Ser Arg Ala Ser

```
                   355                 360                 365
Ser Arg Ala Ser Ser Pro Arg Pro Asp Leu Glu Ile
        370                 375                 380

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Phe Glu Val Ala Phe Leu Leu Ile Gln Trp Ile
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Leu Ile Gln Trp Tyr Ile Gly Phe Ser Leu
1               5                   10

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Leu Ser Ala Val Tyr Thr Cys Lys Arg Asp Pro Cys Pro His Gln
1               5                   10                  15

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Val Asp Cys Phe Leu Ser Arg Pro Thr Glu Lys Thr
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Arg Pro Thr Glu Lys Thr Ile Phe Ile Ile
1               5                   10

<210> SEQ ID NO 20
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 20

Leu Gly Thr Ala Val Glu Ser Ala Trp Gly Asp Glu Gln
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Ser Ala Phe Arg Cys Asn Thr Gln Gln Pro Gly
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Gln Pro Gly Cys Glu Asn Val Cys Tyr Asp Lys
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Val Cys Tyr Asp Lys Ser Phe Pro Ile Ser His Val Arg
1               5                   10

<210> SEQ ID NO 24
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ala Ala Glu Ser Val Trp Gly Asp Glu Ile Lys Ser Ser Phe Ile Cys
1               5                   10                  15

Asn Thr Leu Gln Pro Gly Cys Asn Ser Val Cys Tyr Asp His Phe Phe
            20                  25                  30

Pro Ile Ser His Val Arg
35

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 25

Glu Ser Val Trp Gly Asp Glu Lys Ser Ser Phe Ile
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Cys Asn Thr Leu Gln Pro Gly Cys Asn Ser Val
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Val Cys Tyr Asp His Phe Phe Pro Ile Ser His
1               5                   10

<210> SEQ ID NO 28
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Leu Val Lys Cys Glu Ala Phe Pro Cys Pro Asn Thr Val Asp Cys
1               5                   10                  15

Phe Val Ser Arg Pro Thr Glu Lys Thr
            20                  25

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Val Lys Cys Glu Ala Phe Pro Cys Pro Asn Thr Val
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Val Asp Cys Phe Val Ser Arg Pro Thr Glu Lys Thr
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Val Cys Tyr Asp His Phe Phe Pro Ile Ser His Val Arg
1               5                   10

<210> SEQ ID NO 32
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Val Trp Gly Asp Glu Lys Ser Ser Phe Ile Cys Asn Thr Leu Gln Pro
1               5                   10                  15

Gly Tyr

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asp Glu Lys Ser Ser Phe Ile Cys Asn Thr Leu Gln Pro Gly Tyr
1               5                   10                  15

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ser Arg Pro Thr Glu Lys Thr Val Phe Thr Val
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Arg Pro Thr Glu Lys Thr
1               5

<210> SEQ ID NO 36
<211> LENGTH: 12
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 36

Ile Cys Asn Thr Leu Gln Pro Gly Cys Asn Ser Val
1               5                   10

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Phe Leu Asp Thr Leu His Val Cys Arg Arg Ser Pro Cys Pro His Pro
1               5                   10                  15

<210> SEQ ID NO 38
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Arg Asp Pro Cys His Gln Val Asp Cys Phe Leu Ser Arg Pro Thr
1               5                   10                  15

Glu Lys

<210> SEQ ID NO 39
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Lys Glu Val Trp Gly Asp Glu Gln Ala Asp Phe Val Cys Asn Thr Leu
1               5                   10                  15

Gln Pro Gly Cys Lys Asn Val Cys Tyr Asp His Tyr Phe Pro Ile Ser
            20                  25                  30

His Ile Arg
        35

<210> SEQ ID NO 40
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Glu Val Trp Gly Asp Glu Gln Glu Asp Phe Val Cys Asn Thr Leu
1               5                   10                  15

Gln Pro Gly Cys Lys Asn Val Cys Tyr Asp His Phe Phe Pro Val Ser
            20                  25                  30

His Ile Arg
        35

```
<210> SEQ ID NO 41
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Glu Val Trp Asp Asp Glu Gln Lys Asp Phe Val Cys Asn Thr Lys
1               5                   10                  15

Gln Pro Gly Cys Pro Asn Val Cys Tyr Asp Glu Phe Phe Pro Val Ser
            20                  25                  30

His Val Arg
        35

<210> SEQ ID NO 42
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Arg Val Trp Gly Asp Glu Gln Lys Asp Phe Asp Cys Asn Thr Lys
1               5                   10                  15

Gln Pro Gly Cys Thr Asn Val Cys Tyr Asp Asn Tyr Phe Pro Ile Ser
            20                  25                  30

Asn Ile Arg
        35

<210> SEQ ID NO 43
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Arg Val Trp Ser Asp Asp His Lys Asp Phe Asp Cys Asn Thr Arg
1               5                   10                  15

Gln Pro Gly Cys Ser Asn Val Cys Phe Asp Glu Phe Phe Pro Val Ser
            20                  25                  30

His Val Arg
        35

<210> SEQ ID NO 44
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Ser Val Trp Gly Asp Glu Lys Ser Ser Phe Ile Cys Asn Thr Leu
1               5                   10                  15

Gln Pro Gly Cys Asn Ser Val Cys Tyr Asp Gln Phe Phe Pro Ile Ser
            20                  25                  30

His Val Arg
        35
```

<210> SEQ ID NO 45
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Ser Val Trp Gly Asp Glu Gln Ser Asp Phe Glu Cys Asn Thr Ala
1               5                   10                  15

Gln Pro Gly Cys Thr Asn Val Cys Tyr Asp Gln Ala Phe Pro Ile Ser
            20                  25                  30

His Ile Arg
        35

<210> SEQ ID NO 46
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Ser Val Trp Gly Asp Glu Gln Ser Asp Phe Glu Cys Asn Thr Ala
1               5                   10                  15

Gln Pro Gly Cys Thr Asn Val Cys Tyr Asp Gln Ala Phe Pro Ile Ser
            20                  25                  30

His Ile Arg
        35

<210> SEQ ID NO 47
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Arg Pro Val Tyr Gln Asp Glu Gln Arg Phe Val Cys Asn Thr Leu
1               5                   10                  15

Gln Pro Gly Cys Ala Asn Val Cys Tyr Asp Val Phe Ser Pro Val Ser
            20                  25                  30

His Leu Arg
        35

<210> SEQ ID NO 48
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Ser Ala Trp Gly Asp Glu Gln Ser Ala Phe Arg Cys Asn Thr Gln
1               5                   10                  15

Gln Pro Gly Cys Glu Asn Val Cys Tyr Asp Lys Ser Phe Pro Ile Ser
            20                  25                  30

His Val Arg
        35

<210> SEQ ID NO 49
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Asp Val Trp Gly Asp Glu Gln Ser Asp Phe Thr Cys Asn Thr Gln
1               5                   10                  15

Gln Pro Gly Cys Asx Asn Val Cys Tyr Asx Arg Ala Phe Pro Ile Ser
            20                  25                  30

His Ile Arg
        35

<210> SEQ ID NO 50
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Ala Ile Tyr Ser Asp Glu Gln Ala Lys Phe Thr Cys Asn Thr Arg
1               5                   10                  15

Gln Pro Gly Cys Asp Asn Val Cys Tyr Asp Ala Phe Ala Pro Leu Ser
            20                  25                  30

His Val Arg
        35

<210> SEQ ID NO 51
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Ser Ser Trp Gly Asp Glu Gln Ala Asp Phe Arg Cys Asp Thr Ile
1               5                   10                  15

Gln Pro Gly Cys Gln Asn Val Cys Thr Asp Gln Ala Phe Pro Ile Ser
            20                  25                  30

His Ile Arg
        35

<210> SEQ ID NO 52
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gly Glu Ser Ile Tyr Tyr Asp Glu Gln Ser Lys Phe Val Cys Asn Thr
1               5                   10                  15

Glu Gln Pro Gly Cys Glu Asn Val Cys Tyr Asp Ala Phe Ala Pro Leu
            20                  25                  30

Ser His Val Arg

```
<210> SEQ ID NO 53
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Tyr Val Phe Tyr Val Met Tyr Asp Gly Phe Ser Met Gln Arg Leu
1               5                   10                  15

Val Lys Cys Asn Ala Trp Pro Cys Pro Asn Thr Val Asp Cys Phe Val
            20                  25                  30

Ser Arg Pro Thr Glu Lys Thr
        35

<210> SEQ ID NO 54
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Tyr Val Phe Tyr Phe Leu Tyr Asn Gly Tyr His Leu Pro Trp Val
1               5                   10                  15

Leu Lys Cys Gly Ile Asp Pro Cys Pro Asn Leu Val Asp Cys Phe Ile
            20                  25                  30

Ser Arg Pro Thr Glu Lys Thr
        35

<210> SEQ ID NO 55
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Leu Tyr Ile Phe His Arg Leu Tyr Lys Asp Tyr Asp Met Pro Arg Val
1               5                   10                  15

Val Ala Cys Ser Val Glu Pro Cys Pro His Thr Val Asp Cys Tyr Ile
            20                  25                  30

Ser Arg Pro Thr Glu Lys Lys
        35

<210> SEQ ID NO 56
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Leu Tyr Leu Leu His Thr Leu Trp His Gly Phe Asn Met Pro Arg Leu
1               5                   10                  15

Val Gln Cys Ala Asn Val Ala Pro Cys Pro Asn Ile Val Asp Cys Tyr
            20                  25                  30
```

Ile Ala Arg Pro Thr Glu Lys Lys
        35                  40

<210> SEQ ID NO 57
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Leu Tyr Val Phe His Ser Phe Tyr Pro Lys Tyr Ile Leu Pro Pro Val
1               5                   10                  15

Val Lys Cys His Ala Asp Pro Cys Pro Asn Ile Val Asp Cys Phe Ile
            20                  25                  30

Ser Lys Pro Ser Glu Lys Asn
        35

<210> SEQ ID NO 58
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Tyr Val Phe Tyr Leu Leu Tyr Pro Gly Tyr Ala Met Val Arg Leu
1               5                   10                  15

Val Lys Cys Asp Val Tyr Pro Cys Pro Asn Thr Val Asp Cys Phe Val
            20                  25                  30

Ser Arg Pro Thr Glu Lys Thr
        35

<210> SEQ ID NO 59
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Leu Tyr Gly Trp Thr Met Glu Pro Val Phe Val Cys Gln Arg Ala Pro
1               5                   10                  15

Cys Pro Tyr Leu Val Asp Cys Phe Val Ser Arg Pro Thr Glu Lys Thr
            20                  25                  30

<210> SEQ ID NO 60
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Leu Tyr Gly Trp Thr Met Glu Pro Val Phe Val Cys Gln Arg Ala Pro
1               5                   10                  15

Cys Pro Tyr Leu Val Asp Cys Phe Val Ser Arg Pro Thr Glu Lys Thr
            20                  25                  30

<210> SEQ ID NO 61

```
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gly Ala Leu His Tyr Phe Leu Phe Gly Phe Leu Ala Pro Lys Lys Phe
1               5                   10                  15

Pro Cys Thr Arg Pro Pro Cys Thr Gly Val Val Asp Cys Tyr Val Ser
            20                  25                  30

Arg Pro Thr Ser Lys Ser
        35

<210> SEQ ID NO 62
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Leu Leu Ile Gln Trp Tyr Ile Tyr Gly Phe Ser Leu Ser Ala Val Tyr
1               5                   10                  15

Thr Cys Lys Arg Asp Pro Cys Pro His Gln Val Asp Cys Phe Leu Ser
            20                  25                  30

Arg Pro Thr Glu Lys Thr
        35

<210> SEQ ID NO 63
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Ile Ala Gly Gln Tyr Phe Leu Tyr Gly Phe Glu Leu Lys Pro Leu Tyr
1               5                   10                  15

Arg Cys Asp Arg Trp Pro Cys Pro Asn Thr Val Asp Cys Phe Ile Ser
            20                  25                  30

Arg Pro Thr Glu Lys Thr
        35

<210> SEQ ID NO 64
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Leu Val Gly Gln Tyr Leu Leu Tyr Gly Phe Glu Val Arg Pro Phe Phe
1               5                   10                  15

Pro Cys Ser Arg Gln Pro Cys Pro His Val Val Asp Cys Phe Val Ser
            20                  25                  30

Arg Pro Thr Glu Lys Thr
        35
```

```
<210> SEQ ID NO 65
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Ile Val Gly Gln Tyr Phe Ile Tyr Gly Ile Phe Leu Thr Thr Leu His
1               5                   10                  15

Val Cys Arg Arg Ser Pro Cys Pro His Pro Val Asn Cys Tyr Val Ser
            20                  25                  30

Arg Pro Thr Glu Lys Asn
        35

<210> SEQ ID NO 66
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Leu Ile Gly Gln Tyr Phe Leu Tyr Gly Phe Gln Val His Pro Phe Tyr
1               5                   10                  15

Val Cys Ser Arg Leu Pro Cys His Pro Lys Ile Asp Cys Phe Ile Ser
            20                  25                  30

Arg Pro Thr Glu Lys Thr
        35

<210> SEQ ID NO 67
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Leu Leu Ile Gln Trp Tyr Ile Tyr Gly Phe Ser Leu Ser Ala Val Tyr
1               5                   10                  15

Thr Cys Lys Arg Asp Pro Cys Pro His Gln Val Asp Cys Phe Leu Ser
            20                  25                  30

Arg Pro Thr Glu Lys Thr Ile Phe Ile Ile
        35                  40

<210> SEQ ID NO 68
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Met Tyr Val Phe Tyr Val Met Tyr Asp Gly Phe Ser Met Gln Arg Leu
1               5                   10                  15

Val Lys Cys Asn Ala Trp Pro Cys Pro Asn Thr Val Asp Cys Phe Val
            20                  25                  30

Ser Arg Pro Thr Glu Lys Thr Val Phe Thr Val
        35                  40
```

<210> SEQ ID NO 69
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Tyr Val Phe Tyr Phe Leu Tyr Asn Gly Tyr His Leu Pro Trp Val Leu
1               5                   10                  15

Lys Cys Gly Ile Asp Pro Cys Pro Asn Leu Val Asp Cys Phe Ile Ser
            20                  25                  30

Arg Pro Thr Glu Lys Thr Val Phe Thr Ile
        35                  40

<210> SEQ ID NO 70
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Leu Tyr Ile Phe His Arg Leu Tyr Lys Asp Tyr Asp Met Pro Arg Val
1               5                   10                  15

Val Ala Cys Ser Val Glu Pro Cys Pro His Thr Val Asp Cys Tyr Ile
            20                  25                  30

Ser Arg Pro Thr Glu Lys Lys Val Phe Thr Tyr
        35                  40

<210> SEQ ID NO 71
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Leu Tyr Leu Leu His Thr Leu Trp His Gly Phe Asn Met Pro Arg Leu
1               5                   10                  15

Val Gln Cys Ala Asn Val Ala Pro Cys Pro Asn Ile Val Asp Cys Tyr
            20                  25                  30

Ile Ala Arg Pro Thr Glu Lys Lys Thr Tyr
        35                  40

<210> SEQ ID NO 72
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Leu Tyr Val Phe His Ser Phe Tyr Pro Lys Tyr Ile Leu Pro Pro Val
1               5                   10                  15

Val Lys Cys His Ala Asp Pro Cys Pro Asn Ile Val Asp Cys Phe Ile
            20                  25                  30

Ser Lys Pro Ser Glu Lys Asn Ile Phe Thr Leu
        35                  40

<210> SEQ ID NO 73
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met Tyr Val Phe Tyr Leu Leu Tyr Pro Gly Tyr Ala Met Val Arg Leu
1               5                   10                  15

Val Lys Cys Asp Val Tyr Pro Cys Pro Asn Thr Val Asp Cys Phe Val
                20                  25                  30

Ser Arg Pro Thr Glu Lys Thr Val Phe Thr Val
            35                  40

<210> SEQ ID NO 74
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Leu Tyr Gly Trp Thr Met Glu Pro Val Phe Val Cys Gln Arg Ala Pro
1               5                   10                  15

Cys Pro Tyr Leu Val Asp Cys Phe Val Ser Arg Pro Thr Glu Lys Thr
                20                  25                  30

Ile Phe Ile Ile
        35

<210> SEQ ID NO 75
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Leu Tyr Gly Trp Thr Met Glu Pro Val Phe Val Cys Gln Arg Ala Pro
1               5                   10                  15

Cys Pro Tyr Leu Val Asp Cys Phe Val Ser Arg Pro Thr Glu Lys Thr
                20                  25                  30

Ile Phe Ile Ile
        35

<210> SEQ ID NO 76
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gly Ala Leu His Tyr Phe Leu Phe Gly Phe Leu Ala Pro Lys Lys Phe
1               5                   10                  15

Pro Cys Thr Arg Pro Cys Thr Gly Val Val Asp Cys Tyr Val Ser
                20                  25                  30

Arg Pro Thr Glu Lys Ser Leu Leu Met Leu

```
                35                  40

<210> SEQ ID NO 77
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Ile Ala Gly Gln Tyr Phe Leu Tyr Gly Phe Glu Leu Lys Pro Leu Tyr
1               5                   10                  15

Arg Cys Asp Arg Trp Pro Cys Pro Asn Thr Val Asp Cys Phe Ile Ser
            20                  25                  30

Arg Pro Thr Glu Lys Thr Ile Phe Ile Ile
        35                  40

<210> SEQ ID NO 78
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Leu Val Gly Gln Tyr Leu Leu Tyr Gly Phe Glu Val Arg Pro Phe Phe
1               5                   10                  15

Pro Cys Ser Arg Gln Pro Cys Pro His Val Val Asp Cys Phe Val Ser
            20                  25                  30

Arg Pro Thr Glu Lys Thr Val Phe Leu Leu
        35                  40

<210> SEQ ID NO 79
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Ile Val Gly Gln Tyr Phe Ile Tyr Gly Ile Phe Leu Thr Thr Leu His
1               5                   10                  15

Val Cys Arg Arg Ser Pro Cys Pro His Pro Val Asn Cys Tyr Ser Arg
            20                  25                  30

Pro Thr Glu Lys Asn Val Phe Ile Val
        35                  40

<210> SEQ ID NO 80
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Leu Ile Gly Gln Tyr Phe Leu Tyr Gly Phe Gln Val His Pro Phe Tyr
1               5                   10                  15

Val Cys Ser Arg Leu Pro Cys His Pro Lys Ile Asp Cys Phe Ile Ser
            20                  25                  30
```

```
Arg Pro Thr Glu Lys Thr Ile Phe Leu Leu
        35                  40
```

<210> SEQ ID NO 81
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

```
Leu Gly Thr Ala Ala Glu Ser Ser Trp Gly Asp Glu Gln Ala Asp Phe
1               5                   10                  15

Arg Cys Asp Thr Ile Gln Pro Gly Cys Gln Asn Val Cys Thr Asp Gln
            20                  25                  30

Ala Phe Pro Ile Ser His Ile Arg Phe Trp Val Leu Gln
        35                  40                  45
```

<210> SEQ ID NO 82
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

```
Leu Gly Thr Ala Ala Glu Ser Ser Trp Gly Asp Glu Gln Ala
1               5                   10
```

<210> SEQ ID NO 83
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

```
Asp Glu Gln Ala Asp Phe Arg Cys Asp Thr Ile Gln Pro
1               5                   10
```

<210> SEQ ID NO 84
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

```
Thr Ile Gln Pro Gly Cys Gln Asn Val Cys Thr Asp Gln
1               5                   10
```

<210> SEQ ID NO 85
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

```
Val Cys Thr Asp Gln Ala Phe Pro Ile Ser His Ile Arg
1               5                   10
```

<210> SEQ ID NO 86
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ala Phe Pro Ile Ser His Ile Arg Phe Trp Val Leu Gln
1               5                   10

<210> SEQ ID NO 87
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Met Glu Val Gly Phe Ile Val Gly Gln Tyr Phe Ile Tyr Gly Ile Phe
1               5                   10                  15

Leu Thr Thr Leu His Val Cys Arg Arg Ser Pro Cys Pro His Pro Val
            20                  25                  30

Asn Cys Tyr Val Ser Arg Pro Thr Glu Lys Asn Val Phe Ile Val
        35                  40                  45

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Met Glu Val Gly Phe Ile Val Gly Gln Tyr Phe
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ile Val Gly Gln Tyr Phe Ile Tyr Gly Ile Phe Leu
1               5                   10

<210> SEQ ID NO 90
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Ile Phe Leu Thr Thr Leu His Val Cys Arg Arg Ser Pro
1               5                   10

<210> SEQ ID NO 91
<211> LENGTH: 12

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Arg Ser Pro Cys Pro His Pro Val Asn Cys Tyr
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Val Asn Cys Tyr Val Ser Arg Pro Thr Glu Lys Asn
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ser Arg Pro Thr Glu Lys Asn Val Phe Ile Val
1               5                   10

<210> SEQ ID NO 94
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Leu Thr Ala Val Gly Gly Glu Ser Ile Tyr Tyr Asp Glu Gln Ser Lys
1               5                   10                  15

Phe Val Cys Asn Thr Glu Gln Pro Gly Cys Glu Asn Val Cys Tyr Asp
            20                  25                  30

Ala Phe Ala Pro Leu Ser His Val Arg Phe Trp Val Phe Gln
        35                  40                  45

<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Leu Thr Ala Val Gly Gly Glu Ser Ile Tyr Tyr Asp Glu Gln Ser
1               5                   10                  15

<210> SEQ ID NO 96
<211> LENGTH: 13
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 96

Asp Glu Gln Ser Lys Phe Val Cys Asn Thr Glu Gln Pro
1               5                   10

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Thr Glu Gln Pro Gly Cys Glu Asn Val Cys Tyr Asp Ala
1               5                   10

<210> SEQ ID NO 98
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Val Cys Tyr Asp Ala Phe Ala Pro Leu Ser His Val Arg
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ala Pro Leu Ser His Val Arg Phe Trp Val Phe Gln
1               5                   10

<210> SEQ ID NO 100
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Phe Glu Val Gly Phe Leu Ile Gly Gln Tyr Phe Leu Tyr Gly Phe Gln
1               5                   10                  15

Val His Pro Phe Tyr Val Cys Ser Arg Leu Pro Cys His Pro Lys Ile
            20                  25                  30

Asp Cys Phe Ile Ser Arg Pro Thr Glu Lys Thr Ile Phe Leu Leu
        35                  40                  45

<210> SEQ ID NO 101
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 101

Phe Glu Val Gly Phe Leu Ile Gly Gln Tyr Phe
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Leu Ile Gly Gln Tyr Phe Leu Tyr Gly Phe Gln Val
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Phe Gln Val His Pro Phe Tyr Val Cys Ser Arg Leu Pro
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ser Arg Leu Pro Cys His Pro Lys Ile Asp Cys Phe
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ile Asp Cys Phe Ile Ser Arg Pro Thr Glu Lys Thr
1               5                   10

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ser Arg Pro Thr Glu Lys Thr Ile Phe Leu Leu
1               5                   10

<210> SEQ ID NO 107
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 107

Ser Arg Gly Gly Glu Lys Asn Val Phe Ile Val
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Tyr Val Cys Ser Arg Leu Pro Cys His Pro
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gln Val His Pro Phe Tyr Val Cys Ser Arg Leu
1               5                   10

<210> SEQ ID NO 110
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Phe Glu Val Gly Phe Leu Ile Gly Gln Tyr Phe Leu Tyr
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Gln Tyr Phe Leu Tyr Gly Phe Gln Val His Pro
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Phe Gln Val His Pro Phe Tyr Val Cys Ser Arg
1               5                   10
```

<210> SEQ ID NO 113
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ala Val Gly Gly Glu Ser Ile Tyr Tyr Asp Glu Gln
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Tyr Asp Glu Gln Ser Lys Phe Val Cys Asn Thr Glu
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Asn Thr Glu Gln Pro Gly Cys Glu Asn Val Cys Tyr
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Cys Tyr Asp Ala Phe Ala Pro Leu Ser His Val Arg
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Phe Ala Pro Leu Ser His Val Arg Phe Trp Val Phe
1               5                   10

<210> SEQ ID NO 118
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 118

Leu Ile Gly Gln Tyr
1               5

<210> SEQ ID NO 119
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gln Val His Pro Phe
1               5

<210> SEQ ID NO 120
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Tyr Val Cys Ser Arg
1               5

<210> SEQ ID NO 121
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ser Arg Leu Pro Cys
1               5

<210> SEQ ID NO 122
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Leu Pro Cys His Pro
1               5

<210> SEQ ID NO 123
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Glu Ser Ile Tyr
1               5

<210> SEQ ID NO 124
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Tyr Asp Glu Gln Ser Lys
1               5

<210> SEQ ID NO 125
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ser Lys Phe Val Cys Asn
1               5

<210> SEQ ID NO 126
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Thr Glu Gln Pro Gly Cys Glu Asn
1               5

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Val Cys Tyr Asp Ala Phe Ala Pro
1               5

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Leu Ser His Val Arg Phe Trp Val Phe Gln
1               5                   10

<210> SEQ ID NO 129
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Leu Ile Gln Tyr Phe Leu Tyr Gly Phe Gln Val His Pro Phe
```

-continued

<210> SEQ ID NO 130
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Val His Pro Phe Tyr Cys Ser Arg Leu Pro Cys His Pro
1               5                   10

<210> SEQ ID NO 131
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Val Gly Gly Glu Ser Ile Tyr Tyr Asp Glu Gln Ser Lys Phe Val Cys
1               5                   10                  15

Asn Thr Glu Gln Pro Gly
            20

<210> SEQ ID NO 132
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Thr Glu Gln Pro Gly Cys Glu Asn Val Cys Tyr Asp Ala Phe Ala Pro
1               5                   10                  15

Leu Ser His Val Arg Phe
            20

<210> SEQ ID NO 133
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ala Phe Ala Pro Leu Ser His Val Arg Phe Trp Val Phe Gln
1               5                   10

<210> SEQ ID NO 134
<211> LENGTH: 1314
<212> TYPE: DNA
<213> ORGANISM: Homo sapiens

<400> SEQUENCE: 134
ggcttttagc gtgaggaaag taccaaacag cagcggagtt ttaaacttta aatagacagg     60
tctgagtgcc tgaacttgcc ttttcatttt acttcatcct ccaaggagtt caatcacttg    120
gcgtgacttc actacttta agcaaaagag tggtgcccag caacatggg tgactggagc     180 gccttaggca aactccttga caaggttcaa gcctactcaa ctgctggagg gaaggtgtgg    240

-continued

| | |
|---|---|
| ctgtcagtac ttttcatttt ccgaatcctg ctgctgggga cagcggttga gtcagcctgg | 300 |
| ggagatgagc agtctgcctt tcgttgtaac actcagcaac ctggttgtga aaatgtctgc | 360 |
| tatgacaagt ctttcccaat ctctcatgtg cgcttctggg tcctgcagat catatttgtg | 420 |
| tctgtaccca cactcttgta cctggctcat gtgttctatg tgatgcgaaa ggaagagaaa | 480 |
| ctgaacaaga aagaggaaga actcaaggtt gcccaaactg atggtgtcaa tgtggacatg | 540 |
| cacttgaagc agattgagat aaagaagttc aagtacggta ttgaagagca tggtaaggtg | 600 |
| aaaatgcgag gggggttgct gcgaacctac atcatcagta tcctcttcaa gtctatcttt | 660 |
| gaggtggcct tcttgctgat ccagtggtac atctatggat tcagcttgag tgctgtttac | 720 |
| acttgcaaaa gagatccctg cccacatcag gtggactgtt tcctctctcg ccccacggag | 780 |
| aaaaccatct tcatcatctt catgctggtg gtgtccttgg tgtccctggc cttgaatatc | 840 |
| attgaactct tctatgtttt cttcaagggc gttaaggatc gggttaaggg aaagagcgac | 900 |
| ccttaccatg cgaccagtgg tgcgctgagc cctgccaaag actgtgggtc tcaaaaatat | 960 |
| gcttatttca atgctgctc ctcaccaacc gctcccctct cgcctatgtc tcctcctggg | 1020 |
| tacaagctgg ttactggcga cagaaacaat tcttcttgcc gcaattacaa caagcaagca | 1080 |
| agtgagcaaa actgggctaa ttacagtgca gaacaaaatc gaatggggca ggcgggaagc | 1140 |
| accatctcta actcccatgc acagccttt gatttccccg atgataacca gaattctaaa | 1200 |
| aaactagctg ctggacatga attacagcca ctagccattg tggaccagcg accttcaagc | 1260 |
| agagccagca gtcgtgccag cagcagacct cggcctgatg acctggagat ctag | 1314 |

<210> SEQ ID NO 135
<211> LENGTH: 1149
<212> TYPE: DNA
<213> ORGANISM: Homo sapiens

<400> SEQUENCE: 135

| | |
|---|---|
| atgggtgact ggagcgcctt aggcaaactc cttgacaagg ttcaagccta ctcaactgct | 60 |
| ggagggaagg tgtggctgtc agtacttttc attttccgaa tcctgctgct ggggacagcg | 120 |
| gttgagtcag cctggggaga tgagcagtct gcctttcgtt gtaacactca gcaacctggt | 180 |
| tgtgaaaatg tctgctatga caagtctttc ccaatctctc atgtgcgctt ctgggtcctg | 240 |
| cagatcatat ttgtgtctgt acccacactc ttgtacctgg ctcatgtgtt ctatgtgatg | 300 |
| cgaaaggaag agaaactgaa caagaaagag gaagaactca aggttgccca aactgatggt | 360 |
| gtcaatgtgg acatgcactt gaagcagatt gagataaaga gttcaagta cggtattgaa | 420 |
| gagcatggta aggtgaaaat gcgagggggg ttgctgcgaa cctacatcat cagtatcctc | 480 |
| ttcaagtcta tctttgaggt ggccttcttg ctgatccagt ggtacatcta tggattcagc | 540 |
| ttgagtgctg tttacacttg caaaagagat ccctgcccac atcaggtgga ctgtttcctc | 600 |
| tctcgcccca ggagaaaac atcttcatc atcttcatgc tggtggtgtc cttggtgtcc | 660 |
| ctggccttga atatcattga actcttctat gttttcttca agggcgttaa ggatcgggtt | 720 |
| aagggaaaga gcgaccctta ccatgcgacc agtggtgcgc tgagccctgc caaagactgt | 780 |
| gggtctcaaa aatatgctta tttcaatggc tgctcctcac caaccgctcc cctctcgcct | 840 |

```
atgtctcctc ctgggtacaa gctggttact ggcgacagaa acaattcttc ttgccgcaat       900
tacaacaagc aagcaagtga gcaaaactgg gctaattaca gtgcagaaca aaatcgaatg       960
gggcaggcgg gaagcaccat ctctaactcc catgcacagc cttttgattt ccccgatgat      1020
aaccagaatt ctaaaaaact agctgctgga catgaattac agccactagc cattgtggac      1080
cagcgacctt caagcagagc cagcagtcgt gccagcagca gacctcggcc tgatgacctg      1140
gagatctag                                                              1149
```